US010500391B2

(12) United States Patent
Takeuchi

(10) Patent No.: US 10,500,391 B2
(45) Date of Patent: Dec. 10, 2019

(54) ADAPTER FOR MALE CONNECTOR AND MALE CONNECTOR WITH ADAPTER

(71) Applicant: JMS CO., LTD., Hiroshima-shi, Hiroshima (JP)

(72) Inventor: Masahiko Takeuchi, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 122 days.

(21) Appl. No.: 15/748,959

(22) PCT Filed: Aug. 2, 2016

(86) PCT No.: PCT/JP2016/072607
§ 371 (c)(1),
(2) Date: Jan. 30, 2018

(87) PCT Pub. No.: WO2017/022741
PCT Pub. Date: Feb. 9, 2017

(65) Prior Publication Data
US 2019/0001112 A1 Jan. 3, 2019

(30) Foreign Application Priority Data

Aug. 3, 2015 (JP) ................................. 2015-153579

(51) Int. Cl.
*A61M 39/10* (2006.01)
*A61M 39/26* (2006.01)
(Continued)

(52) U.S. Cl.
CPC ........ *A61M 39/1011* (2013.01); *A61M 39/16* (2013.01); *A61M 39/26* (2013.01);
(Continued)

(58) Field of Classification Search
CPC .................. A61M 39/00; A61M 39/10; A61M 2039/1027; A61M 2039/1077;
(Continued)

(56) References Cited

U.S. PATENT DOCUMENTS 5,269,771 A 12/1993 Thomas et al.
5,336,192 A * 8/1994 Palestrant ......... A61M 39/0613
128/912
(Continued)

FOREIGN PATENT DOCUMENTS

EP 2 837 403 2/2015
FR 2 931 363 11/2009
(Continued)

OTHER PUBLICATIONS

Extended European Search Report issued in corresponding European Patent Application No. 16833020.7, dated Feb. 12, 2019, 8 pages.

*Primary Examiner* — Jason E Flick
(74) *Attorney, Agent, or Firm* — Hamre, Schumann, Mueller & Larson, P.C.

(57) ABSTRACT

An adapter (100) has a through hole (103). A first end portion (101) of the adapter includes a tubular portion (110) on which a first projection (111) and a second projection (112) are provided. The adapter can be connected to a male connector at a first position where a claw (32) of the male connector is engaged with the first projection (111) and at a second position where the claw (32) is engaged with the second projection (112). When the adapter is connected at the first position, a flow channel (11) of a male member (10) is sealed with a cover (4). When the adapter is connected at the second position, the adapter compressively deforms an outer circumferential wall (45) of the cover so that the flow channel of the male member is in communication with the through hole (103) of the adapter.

12 Claims, 53 Drawing Sheets

(51) Int. Cl.
*F16L 37/098* (2006.01)
*A61M 39/16* (2006.01)

(52) U.S. Cl.
CPC .... *F16L 37/098* (2013.01); *A61M 2039/1027* (2013.01); *A61M 2039/1077* (2013.01); *A61M 2039/261* (2013.01)

(58) Field of Classification Search
CPC ........ A61M 2039/261; A61M 39/1011; A61M 39/16; A61M 39/26; F16L 37/098; F16L 37/00; F16L 37/08
USPC ......................................................... 604/533
See application file for complete search history.

(56) References Cited

U.S. PATENT DOCUMENTS

| | | | |
|---|---|---|---|
| 6,032,926 A * | 3/2000 | Fuchs | ................. A61J 1/10 251/149.1 |
| 2006/0129109 A1 | 6/2006 | Shaw et al. | |
| 2009/0143758 A1 | 6/2009 | Okiyama | |
| 2009/0163939 A1 | 6/2009 | Mabuchi et al. | |
| 2011/0106046 A1 | 5/2011 | Hiranuma et al. | |
| 2014/0114292 A1 | 4/2014 | Tachizaki et al. | |
| 2015/0008664 A1 | 1/2015 | Tachizaki | |
| 2016/0206868 A1 | 7/2016 | Guala | |

FOREIGN PATENT DOCUMENTS

| | | |
|---|---|---|
| JP | 11-244393 | 9/1999 |
| JP | 2004-000483 | 1/2004 |
| JP | 2006-102255 | 4/2006 |
| JP | 2006-223583 | 8/2006 |
| JP | 2009-101093 | 5/2009 |
| JP | 2012-152269 | 8/2012 |
| JP | 2012-217639 | 11/2012 |
| JP | 2012-254142 | 12/2012 |
| JP | 2013-165830 | 8/2013 |
| JP | 2013-252165 | 12/2013 |
| JP | 2015-073664 | 4/2015 |
| JP | 2015-195849 | 11/2015 |
| JP | 2016-165446 | 9/2016 |
| WO | 2007/114157 | 10/2007 |
| WO | 2009/133755 | 11/2009 |
| WO | 2011/029056 | 3/2011 |
| WO | 2013/154050 | 10/2013 |

* cited by examiner

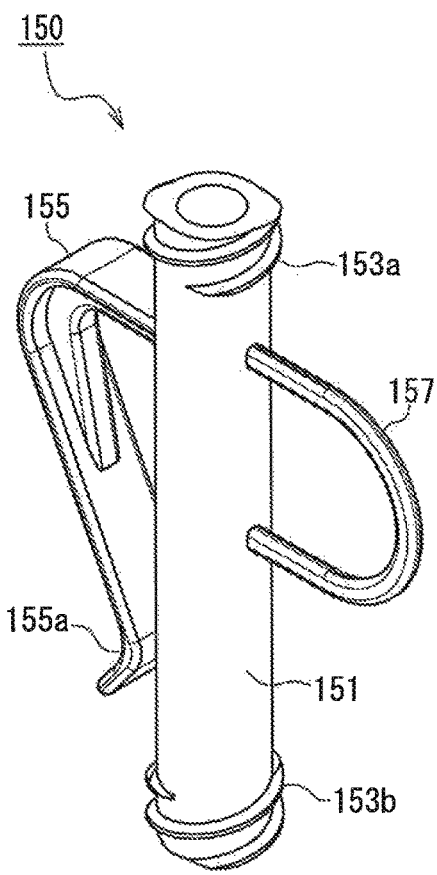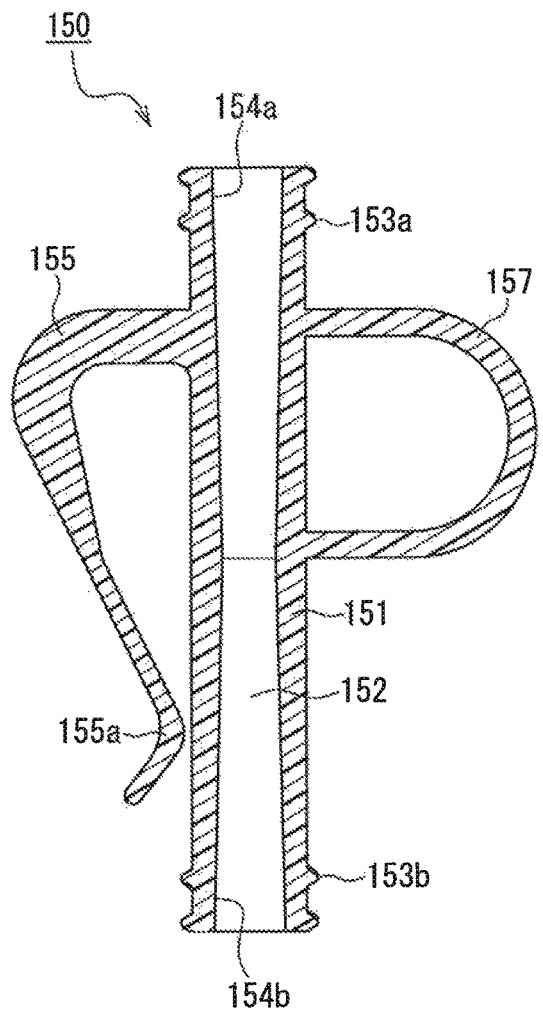
FIG. 17A
FIG. 17B

ADAPTER FOR MALE CONNECTOR AND MALE CONNECTOR WITH ADAPTER

TECHNICAL FIELD

The present invention relates to an adapter that is used by being attached to a male connector. The present invention also relates to a male connector provided with an adapter.

BACKGROUND ART

In hemodialysis, hemofiltration, a cardiac surgery operation, etc., blood drawn from a patient is subjected to a predetermined treatment, and then the processed blood is returned to the patient. For this purpose, an extracorporeal circuit is formed to circulate blood outside the body with the use of a mechanical external force such as a pump. In the extracorporeal circuit, a coupling portion including a male connector and a female connector is used to connect tubes through which blood flows.

If the male connector and the female connector are unintentionally disconnected from each other during blood circulation, the blood that is forced to flow by a pump or the like will leak out and, in the worst case, may result in a serious accident such as patient's death from loss of blood. Therefore, the coupling portion is provided with a lock mechanism for maintaining the connection between the male connector and the female connector to prevent such a serious accident. For example, Patent Documents 1 to 3 disclose a lever lock male connector. This male connector includes a male member and an elastically swingable lock lever. A claw is formed on the leading end of the lock lever and can be engaged with the female connector. The connection between the male connector and the female connector is maintained by engaging (locking) the claw with the female connector while the male member of the male connector is inserted into the female connector.

Moreover, the male connector and the female connector are provided with a mechanism for preventing leakage of blood to the outside even if the male connector and the female connector are unintentionally disconnected from each other. Patent Documents 4, 5 disclose a cover that is attached to the male member of the male connector. The cover is made of an elastic material such as rubber. A straight line-shaped slit (cut portion) is formed in the top of the cover. In the initial state, the male connector is not connected to the female connector, and the male member is housed in the cover. Therefore, the cover covers an opening of a flow channel at the leading end of the male member. When the male connector is connected to the female connector, the cover is compressively deformed in the longitudinal direction of the male member, and the leading end of the male member is inserted into the female connector through the slit of the cover. Thus, the male member and the female connector are in communication with each other, and blood can flow between them. In this state, if the male connector is unintentionally disconnected from the female connector, the cover immediately returns to the initial state, closes the slit, and covers the opening of the male member. Therefore, blood will not leak from the male member to the outside of the cover.

Incidentally, an operation called "priming" is performed before circulating blood in the extracorporeal circuit. The priming operation introduces a fluid (e.g., physiological saline, which is referred to as a "priming fluid" in the following) into a flow channel of the extracorporeal circuit, and discharges air in the flow channel to the outside. This is because if blood circulation is started with air present in the extracorporeal circuit, the air may enter the blood vessels of a patient and create critical health issues.

In order to prevent air in the extracorporeal circuit from flowing into a patient, the priming operation is performed before forming the extracorporeal circuit, i.e., in a state where the male connector and the female connector, which will constitute the coupling portion, are separated from each other. In this state, the flow channel in the male member of the male connector needs to be filled with the priming fluid.

CITATION LIST

Patent Documents

Patent Document 1: JP 2004-000483 A
Patent Document 2: WO 2013/154050
Patent Document 3: JP 2015-073664 A
Patent Document 4: JP 2012-254142 A
Patent Document 5: JP 2013-165830 A
Patent Document 6: JP 2013-252165 A

DISCLOSURE OF INVENTION

Problem to be Solved by the Invention

However, as the male member is provided with the cover, the cover covers the opening at the leading end of the male member in the initial state before the male connector is connected to the female connector. In this state, it is difficult to introduce the priming fluid into the flow channel of the male member. Therefore, it is desirable to make it possible to introduce the priming fluid into the male connector having the cover.

Moreover, the operation of introducing the priming fluid is desired to be simple. Further, it is also desirable to prevent bacteria or the like from entering the flow channel of the male member during the introduction of the priming fluid.

It is an object of the present invention to easily and hygienically introduce a priming fluid into a lever lock male connector having a cover.

Means for Solving Problem

An adapter of the present invention is attachable to and detachable from a male connector. The male connector includes a rod-shaped male member that has a flow channel, a lock lever that is located opposite to the male member, a claw that protrudes from the lock lever toward the male member, and a cover that houses the male member. The lock lever is elastically swingable so that the claw moves away from the male member. The cover includes an outer circumferential wall that is elastically and compressively deformable in a longitudinal direction of the male member, and a head portion that is provided at one end of the outer circumferential wall. The cover is configured such that a leading end of the male member protrudes from the head portion when the outer circumferential wall is compressively deformed. The adapter includes a first end portion and a second end portion. The adapter has a through hole that penetrates the adapter and allows the first end portion to be in communication with the second end portion. The first end portion includes a hollow tubular portion in which the through hole is provided. A first projection and a second projection are provided on an outer circumferential surface of the tubular portion, and the second projection is located on a base end side of the tubular portion with respect to the first projection. The adapter can be connected to the male connector at a first position where the claw of the male connector is engaged with the first projection and at a second position where the claw of the male connector is engaged with the second projection. When the adapter is connected to the male connector at the first position, the flow channel of the male member is sealed with the cover. When the adapter is connected to the male connector at the second position, the adapter compressively deforms the outer circumferential wall of the cover so that the flow channel of the male member is in communication with the through hole of the adapter.

An male connector provided with an adapter of the present invention includes the male connector and the adapter of the present invention.

Effects of the Invention

The adapter of the present invention can be connected to a lever lock male connector having a cover at two positions, i.e., the first position and the second position. Only a simple operation of shifting the adapter from the first position to the second position is required to be able to introduce a priming fluid into the male connector.

The male connector to which the adapter is connected at the first position is stored. Then, the adapter is shifted to the second position immediately before performing the priming operation. This reduces the probability that bacteria or the like will enter the flow channel of the male member during the introduction of the priming fluid. Thus, the priming fluid can be hygienically introduced into the male connector.

BRIEF DESCRIPTION OF DRAWINGS

FIG. 17A is a perspective view of a drain connector that is to be attached to the adapter according to Embodiment 1 of the present invention for priming. FIG. 17B is a cross-sectional view of the drain connector.

DESCRIPTION OF THE INVENTION

Figure 1:
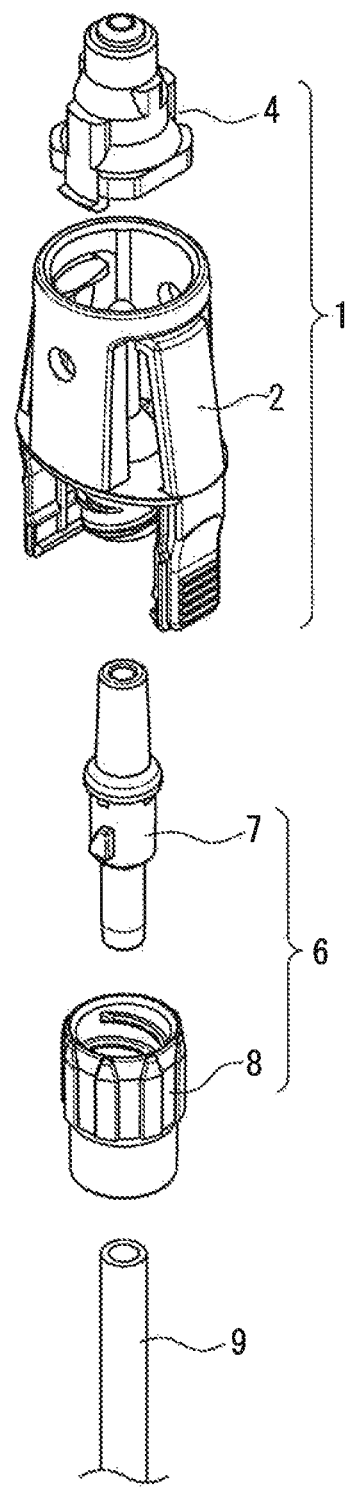
FIG. 1 is an exploded perspective view of an embodiment of a male connector applicable to an adapter of the present invention and a screw lock connector to be connected to the male connector.

As described above, in the initial state of the lever lock male connector having the cover, the cover closes the opening of the flow channel of the male member. As long as the cover closes the opening of the male member, it is difficult to introduce a priming fluid into the flow channel of the male member.

The present inventors conducted studies to examine the priming operation by attaching a dummy member to a male connector. The dummy member was a hollow tubular member with an internal diameter larger than the external diameter of a male member. The dummy member had a projection on its outer circumferential surface. A claw of a lock lever of the male connector was to be engaged with the projection of the dummy member. The male member of the male connector was inserted into the dummy member, and the claw was engaged with the projection of the dummy member. When the dummy member was attached to the male member, the cover was compressively deformed by the dummy member, as in the case where a female connector was connected to the male connector, and the male member penetrated the cover. Thus, the male member and the dummy member were in communication with each other. In this state, a priming fluid was allowed to flow from the male member to the dummy member.

Such a dummy member had previously been prepared separately from the male connector. For the priming operation, first, the dummy member was attached to the male connector. Then, a priming fluid was introduced into the male member. Subsequently, the dummy member was detached from the male connector, and a female connector was connected to the male connector, instead of the dummy member.

However, this method was found to have the following problems: (1) since the dummy member had to be prepared separately from the male connector and attached to the male connector before the priming operation, operations for storage and attachment of the dummy member were complicated; (2) since the dummy member had to be attached to the male connector before the priming operation, there was a possibility that bacteria would enter the flow channel of the male member via the dummy member.

To deal with the above problems, the present inventors conducted studies to examine sterilization and packaging of the male connector and the dummy member in a state in which the dummy member was attached to the male connector (i.e., a state in which the male member and the dummy member were in communication with each other). When extracorporeal blood circulation was carried out in medical institutions such as hospitals, the package was opened to take out the male connector to which the dummy member was attached, and then the priming operation was performed. Thereafter, the dummy member was detached from the male connector, and the female connector was connected to the male connector, instead of the dummy member. This method was able to solve the above two problems because the dummy member had been attached to the male connector and sterilized before they were delivered to medical institutions.

However, the cover was compressively deformed by the dummy member when it was attached to the male connector. In this state, if the cover was allowed to stand for a long time, the cover would be permanently deformed, so that the elastic recovery force for return of the cover to its initial state would be reduced. Thus, the separation of the male connector from the female connector could create a situation where the cover did not return to the initial state and failed to close the opening of the flow channel of the male member. Consequently, the cover could not exhibit the effect of preventing leakage of blood to the outside if the male connector was unintentionally disconnected from the female connector during blood circulation.

The present inventors further conducted intensive studies to find an adapter that is attachable to a lever lock male connector having a cover at two positions, and have completed the present invention.

The adapter of the present invention is attachable to and detachable from a male connector. The male connector includes a rod-shaped male member that has a flow channel, a lock lever that is located opposite to the male member, a claw that protrudes from the lock lever toward the male member, and a cover that houses the male member. The lock lever is elastically swingable so that the claw moves away from the male member. The cover includes an outer circumferential wall that is elastically and compressively deformable in a longitudinal direction of the male member, and a head portion that is provided at one end of the outer circumferential wall. The cover is configured such that a leading end of the male member protrudes from the head portion when the outer circumferential wall is compressively deformed. The adapter includes a first end portion and a second end portion. The adapter has a through hole that penetrates the adapter and allows the first end portion to be in communication with the second end portion. The first end portion includes a hollow tubular portion in which the through hole is provided. A first projection and a second projection are provided on an outer circumferential surface of the tubular portion, and the second projection is located on a base end side of the tubular portion with respect to the first projection. The adapter can be connected to the male connector at a first position where the claw of the male connector is engaged with the first projection and at a second position where the claw of the male connector is engaged with the second projection. When the adapter is connected to the male connector at the first position, the flow channel of the male member is sealed with the cover. When the adapter is connected to the male connector at the second position, the adapter compressively deforms the outer circumferential wall of the cover so that the flow channel of the male member is in communication with the through hole of the adapter.

It is preferable that when the adapter is connected to the male connector at the second position, a liquid-tight seal is formed between the tubular portion and the cover. This can prevent a priming fluid from leaking between the adapter and the cover during the priming operation.

The tubular portion may include an annular rib that surrounds the through hole. In this case, it is preferable that the liquid-tight seal is formed by abutting of a leading end of the annular rib against the head portion of the cover. This allows the annular rib and the head portion to be in contact with each other in a small area. Therefore, the sealing between the adapter and the cover is improved.

It is preferable that when the adapter is connected to the male connector at the first position, the outer circumferential wall of the cover is not substantially compressively deformed. Moreover, it is preferable that when the adapter is in the first position, the adapter is spaced apart from the cover. Thus, even if the male connector to which the adapter is connected at the first position is allowed to stand for a long period of time, the elastic recovery force of the outer circumferential wall of the cover will not be reduced.

The adapter may further include a large diameter portion on a base end of the tubular portion. The large diameter portion may protrude in a radial direction compared to the first projection and the second projection. Thus, the large diameter portion abuts against the male connector (particularly the leading end of a hood of the male connector), and thus can prevent the adapter from being inserted into the male connector (particularly the hood) more than necessary. This is advantageous in preventing damage to the cover due to excessive deformation caused by the adapter.

In the above configuration, the male connector may further include a tubular hood that surrounds the male member. In this case, when the adapter is connected to the male connector at the second position, the large diameter portion may abut against a leading end of the hood. Thus, the adapter cannot be inserted into the hood to a depth deeper than the second position, which can reliably prevent damage to the cover.

The first projection and the second projection may be annular projections that continuously extend in a circumferential direction. Thus, the claw of the male connector can be engaged with the first projection and the second projection regardless of the position of the adapter in the direction of rotation relative to the male connector.

The second projection may have a tapered surface on an end edge thereof facing the first projection, and an external diameter of the tapered surface gradually decreases toward the first projection. Thus, the adapter can easily be shifted from the first position to the second position only by pushing the adapter into the male connector.

The second end portion may include a male luer in which the through hole is provided. An outer circumferential surface of the male luer may be a tapered surface whose external diameter gradually decreases toward a leading end. Thus, a tubular member (e.g., a drain connector) having a female tapered surface that is fitted to the tapered surface of the male lure can be connected to the second end portion in a liquid-tight manner. When the tubular member is fixed to a container, a priming fluid can be stably discharged into the container.

In the above configuration, the second end portion may further include an outer cylinder that surrounds the male luer. A screw structure may be formed on an inner circumferential surface of the outer cylinder. Thus, a tubular member (e.g., a drain connector) having a male thread that is to be screwed into the screw structure, in addition to the female tapered surface that is fitted to the tapered surface of the male luer, can be firmly connected to the second end portion in a liquid-tight manner.

Alternatively, the second end portion of the adapter may be configured symmetrically to the first end portion. This allows two male connectors to be connected at the first position and the second position via the adapter, respectively. Thus, a priming fluid can be simultaneously introduced into the two male connectors.

A male connector provided with an adapter of the present invention includes the above male connector and the above adapter of the present invention.

It is preferable that the male connector provided with the adapter are sterilized and packaged in a state in which the adapter is connected to the male connector at the first position. Thus, the adapter and the male connector can be maintained in good sanitary conditions immediately before performing the priming operation. In medical institutions such as hospitals, it is only necessary to open the package and shift the adapter to the second position so that a priming fluid can be introduced into the male connector. This will reduce the burden of the priming operation on medical institutions. Moreover, the adapter does not have to be stored separately from the male connector. Therefore, this will also reduce the burden of the management of equipment in medical institutions.

Hereinafter, the present invention will be described in detail while showing preferred embodiments thereof. However, it goes without saying that the present invention is not limited to the embodiments below. In the drawings that will be referred to in the following description, only the main members of constituent members of the embodiments of the present invention are shown in a simplified manner for the sake of convenience of description. Accordingly, the present invention may include optional members that are not shown in the drawings below. Moreover, it should be understood that the members shown in the drawings below may be changed or omitted within the scope of the present invention.

An adapter of the present invention is attachable to and detachable from a male connector. The male connector is connected to a tube constituting an extracorporeal circuit.

Before describing the adapter of the present invention, the male connector applicable to the adapter and a connection structure of the male connector and the tube will be described.

FIG. 1 is an exploded perspective view of a male connector 1 and a screw lock connector 6 according to an embodiment of the present invention. The male connector 1 includes a connector main body 2 and a cover 4. The screw lock connector 6 includes a luer main body 7 and a lock nut 8. The screw lock connector 6 is connected to the leading end of a soft tube 9 constituting an extracorporeal circuit. The male connector 1 is removably connected to the screw lock connector 6.

Hereinafter, the various portions will be sequentially described.

1. Male Connector 1.1. Connector Main Body

Figure 2A:
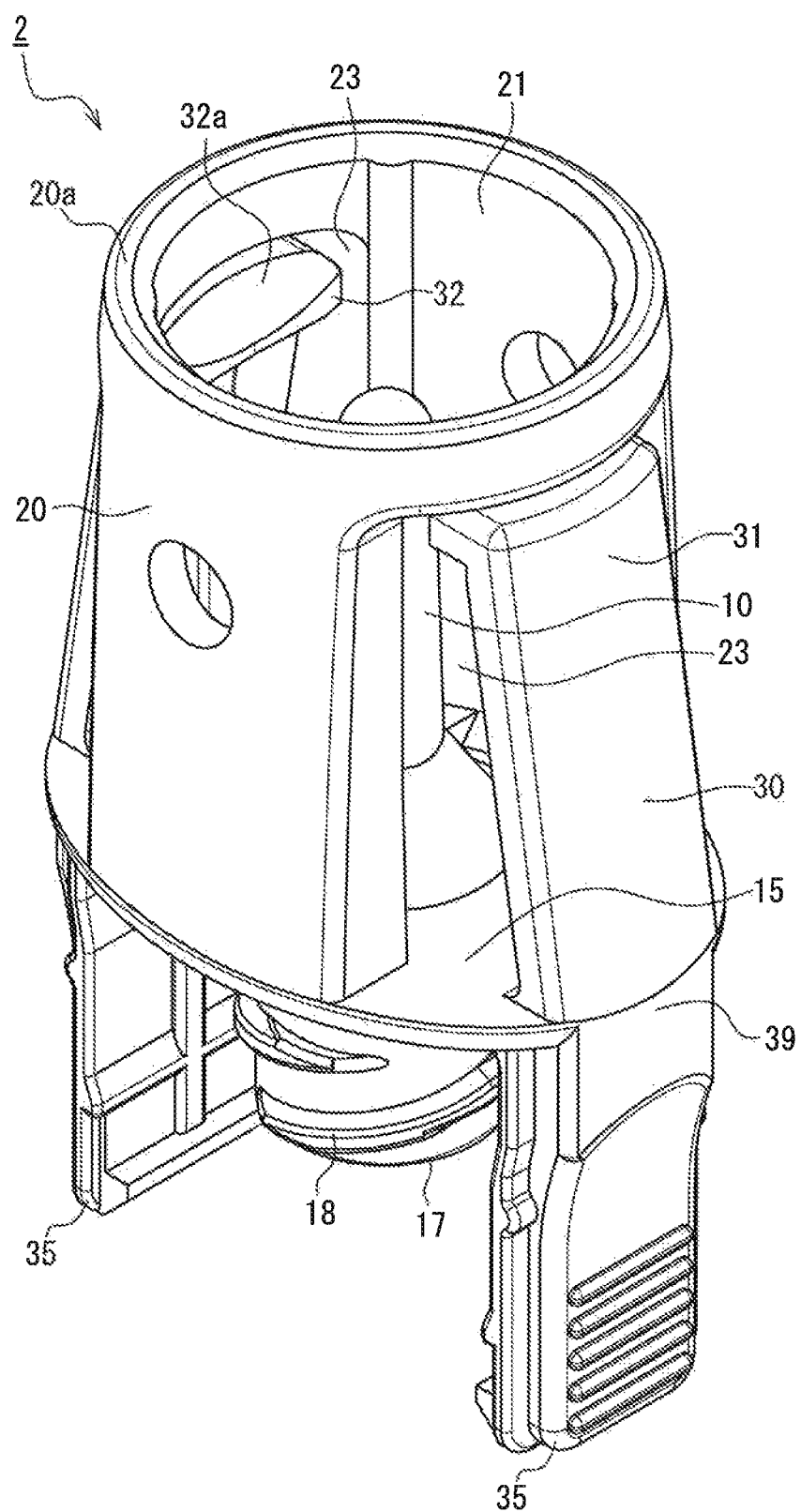
FIG. 2A is a perspective view of a connector main body of the male connector when viewed from above.
Figure 2B:
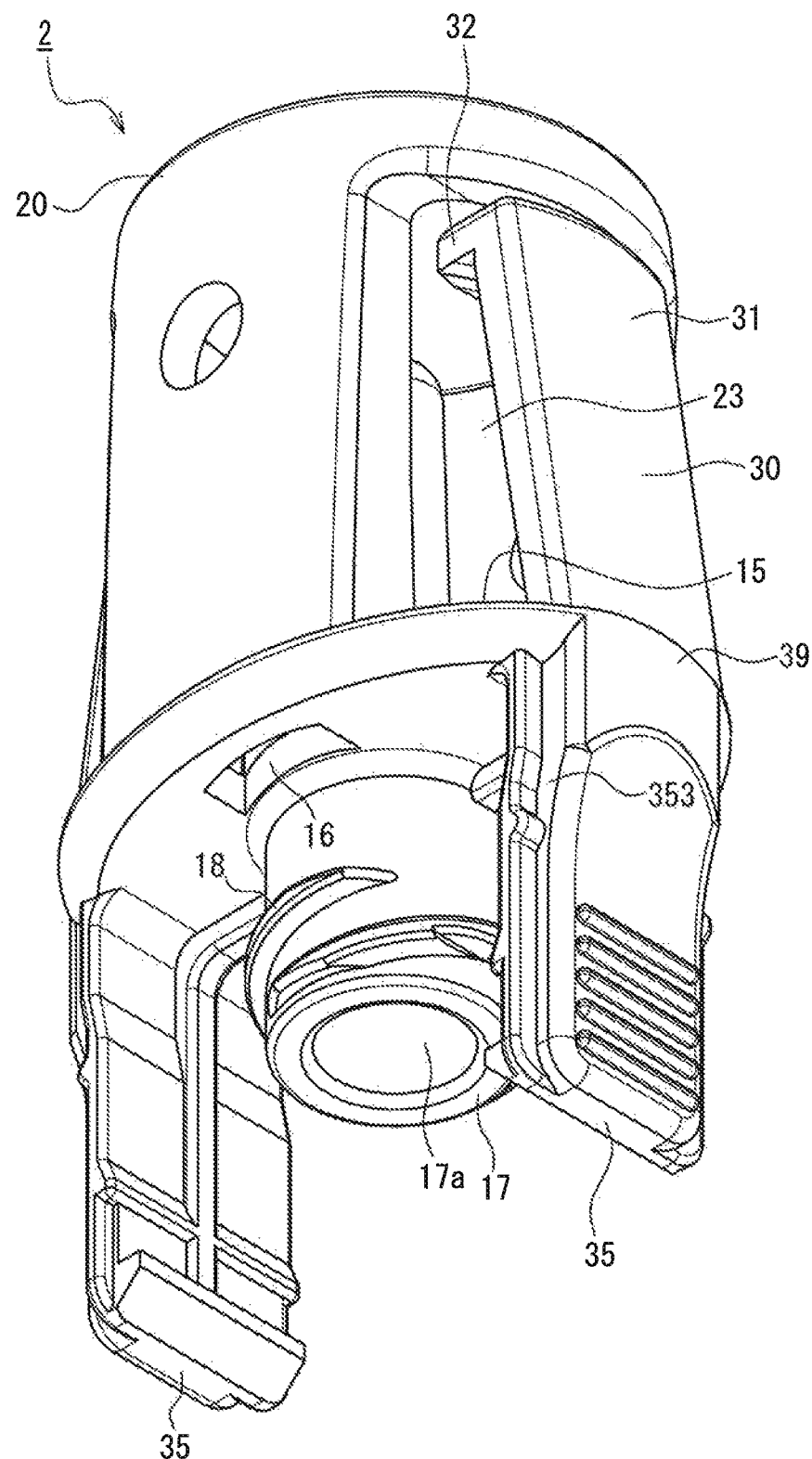
FIG. 2B is a perspective view of the connector main body when viewed from below.
Figure 2C:
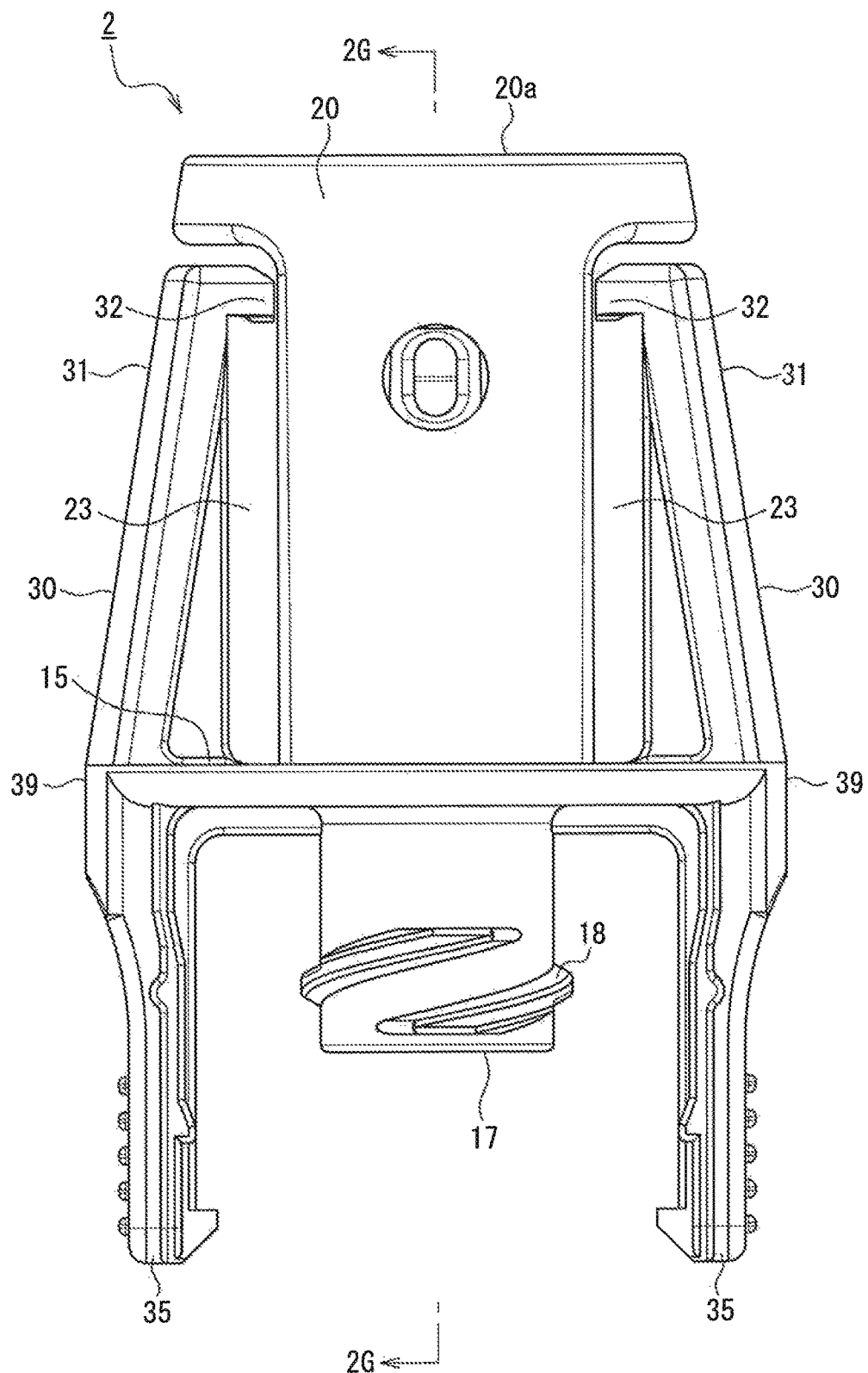
FIG. 2C is a front view of the connector main body.
Figure 2D:
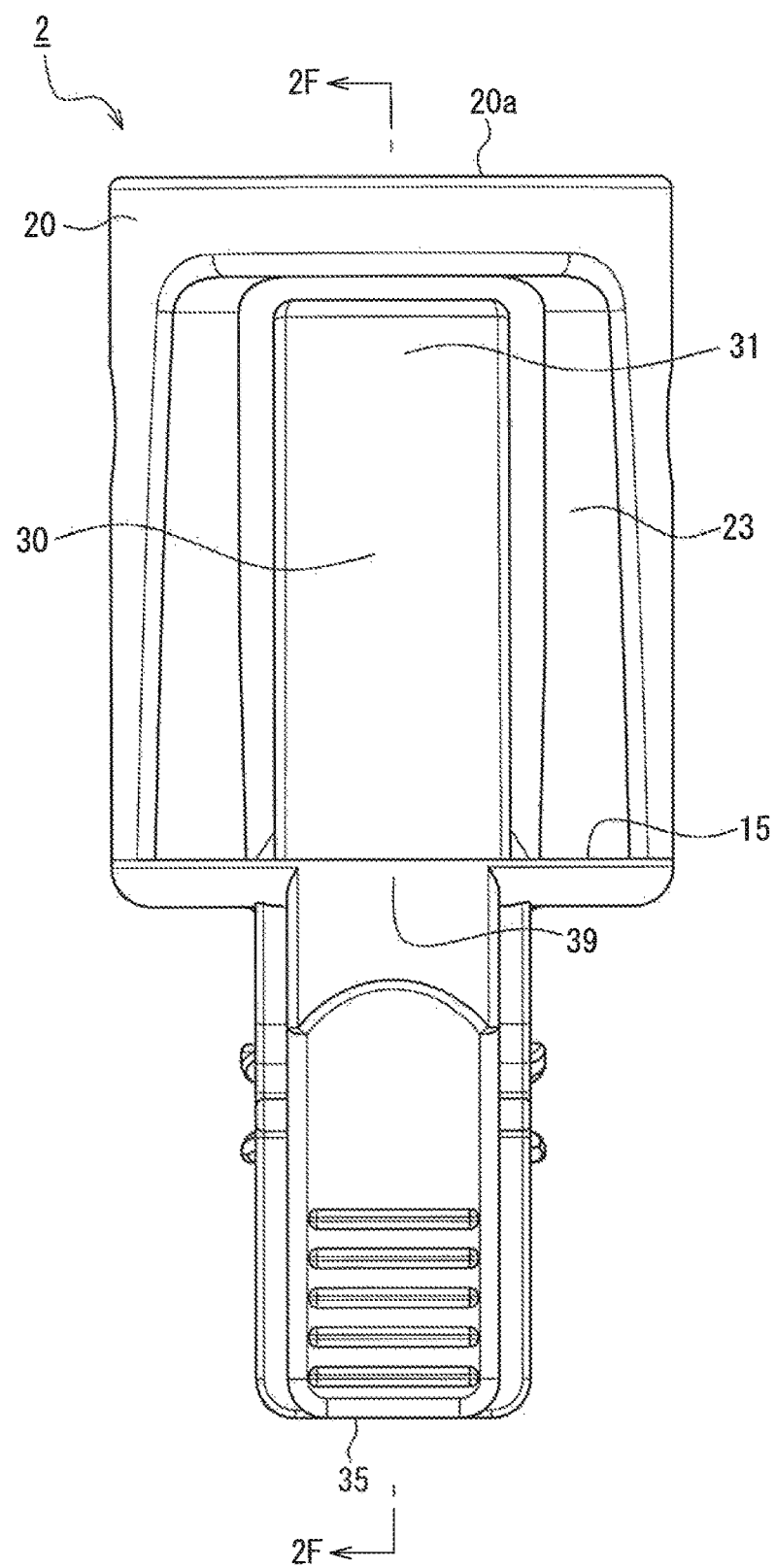
FIG. 2D is a side view of the connector main body.
Figure 2E:
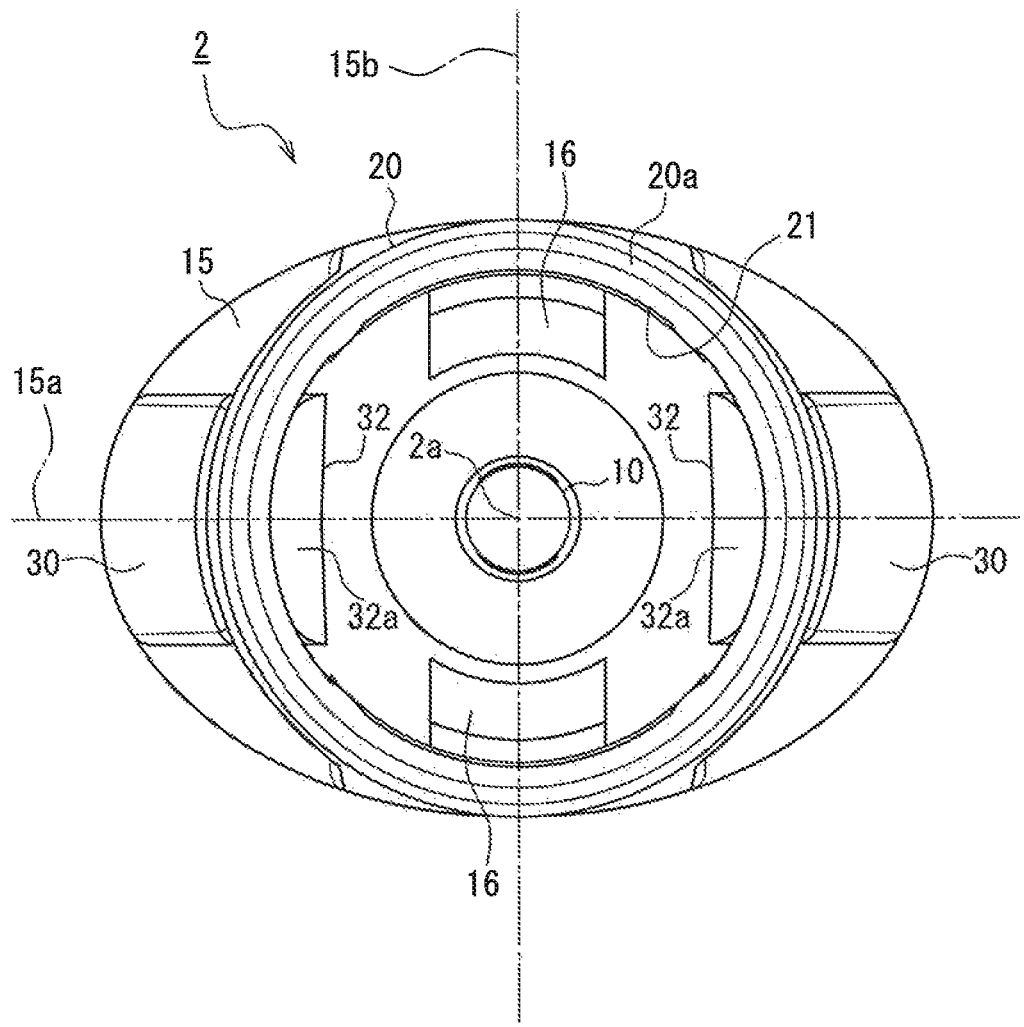
FIG. 2E is a plan view of the connector main body.
Figure 2F:
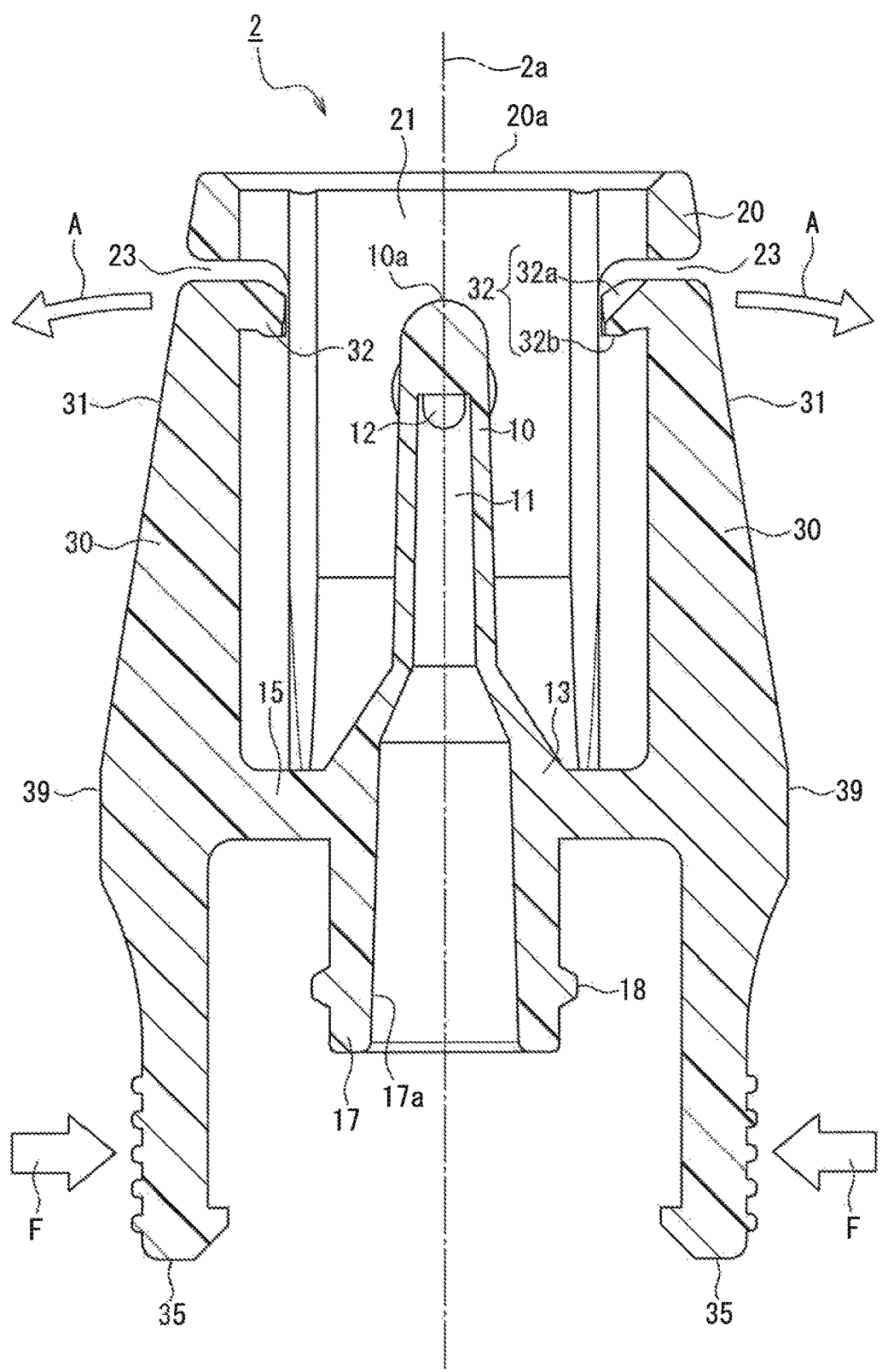
FIG. 2F is a cross-sectional view of the connector main body taken along a vertical plane containing line 2F-2F in FIG. 2D.
Figure 2G:
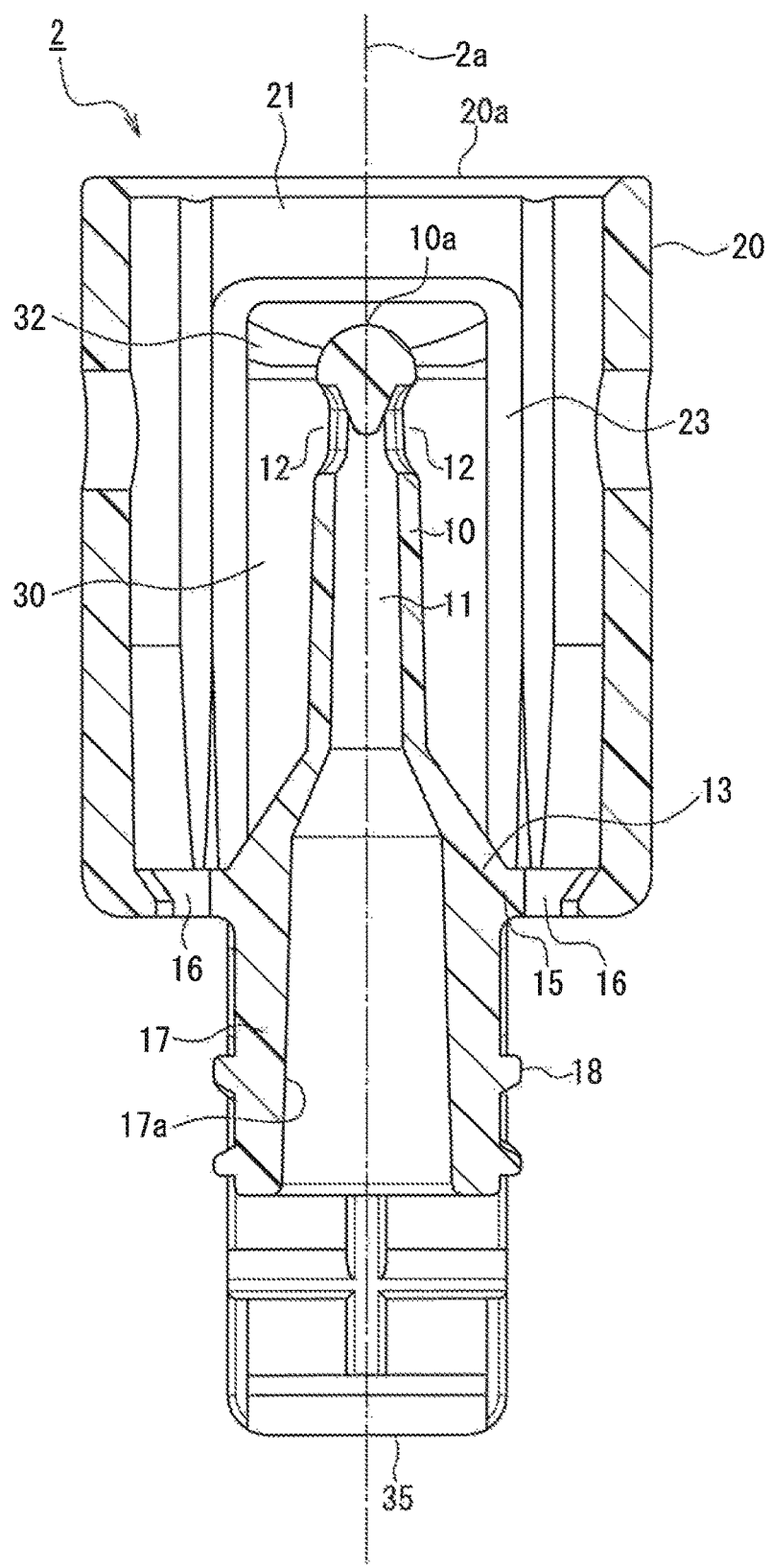
FIG. 2G is a cross-sectional view of the connector main body taken along a vertical plane containing line 2G-2G in FIG. 2C.

A connector main body 2 constituting a male connector 1 will be described. FIG. 2A is a perspective view of the connector main body 2 when viewed from above, and FIG. 2B is a perspective view of the connector main body 2 when viewed from below. FIGS. 2C, 2D, and 2E are a front view, a side view, and a plan view, in that order, of the connector main body 2. FIG. 2F is a cross-sectional view of the connector main body 2 taken along a vertical plane containing line 2F-2F in FIG. 2D. FIG. 2G is a cross-sectional view of the connector main body 2 taken along a vertical plane containing line 2G-2G in FIG. 2C. In FIGS. 2F and 2G, an alternate long and short dash line 2a represents a central axis of the connector main body 2. The central axis 2a also serves as the central axis of the male connector 1 (see FIG. 1).

For the sake of convenience of the following description, the direction that is parallel to the central axis 2a is referred to as a "vertical direction", the direction that is parallel to a plane that is perpendicular to the central axis 2a is referred to as a "horizontal direction", the direction that is orthogonal to the central axis 2a is referred to as a "radial direction" or a "diameter direction", and the direction of rotation about the central axis 2a is referred to as a "circumferential direction". With respect to the radial direction, the side nearer the central axis 2a is referred to as the "inner side", and the side further from the central axis 2a is referred to as the "outer side". "Up" and "down" are defined based on FIGS. 2F and 2G. However, the "vertical direction" and the "horizontal direction" do not mean the actual orientation of the male connector 1 during usage.

As shown in FIGS. 2F and 2G, the connector main body 2 includes a male luer 10 serving as a male member. The male luer 10 is a rod-shaped member extending along and coaxially with the central axis 2a. In this embodiment, a portion of the outer circumferential surface (side surface) of the male luer 10 that is near a leading end 10a and that is to be inserted into a female connector (a septum 810, which will be described later) constitutes a cylindrical surface whose external diameter is constant with respect to the direction of the central axis 2a, and a portion of the outer circumferential surface of the male luer 10 that is near a base end portion 13 constitutes a tapered surface (conical surface) whose external diameter decreases as the distance to the leading end 10a decreases. However, the shape of the outer circumferential surface of the male luer 10 is not limited to the above-described shape, and may be selected as desired. For example, the outer circumferential surface of the male luer 10 may be a cylindrical surface whose external diameter is constant from the base end portion 13 to the leading end 10a. Alternatively, the outer circumferential surface of the male luer 10 may be a smooth curved surface whose external diameter gradually decreases from the base end portion 13 toward the leading end 10a.

A flow channel 11 is formed along the central axis 2a within the male luer 10. The flow channel 11 is not open in the leading end 10a of the male luer 10. Two lateral holes 12 that are in communication with the flow channel 11 are formed in the outer circumferential surface of the male luer 10 at respective positions near the leading end 10a. Each lateral hole 12 penetrates the male luer 10 in the radial direction and is open in the outer circumferential surface of the male luer 10. It should be noted that the number of lateral holes 12 is not necessarily required to be two, and may also be one, or three or more.

A base 15 protrudes outward from the base end portion 13 of the male luer 10. The base 15 is a flat plate-shaped member that is parallel to the horizontal direction. As can be understood from FIG. 2E, when viewed along the central axis 2a, the base 15 has a substantially elliptical shape with a major axis 15a and a minor axis 15b.

A tubular portion 17 protrudes downward from the base 15. The tubular portion 17 has a substantially cylindrical shape that is coaxial with the central axis 2a, and a flow channel that is in communication with the flow channel 11 of the male luer 10 is formed in the tubular portion 17. An inner circumferential surface 17a of the tubular portion 17 is a female tapered surface (e.g., a 6% tapered surface) whose internal diameter increases as the distance from the base 15 increases. A male thread 18 is formed on the outer circumferential surface of the tubular portion 17.

A hood 20 extends upright from the outer end edge of the base 15 toward the same side as the male luer 10. The hood 20 has a hollow tubular shape that surrounds the male luer 10. The hood 20 is open upward. A leading end (upper end) 20a of the hood 20 that surrounds an opening 21 has a circular shape that is coaxial with the central axis 2a. The leading end 20a of the hood 20 is located at a higher position than the leading end 10a of the male luer 10.

A pair of cut-outs 23 are provided in a side wall of the hood 20. The cut-outs 23 are holes (openings) penetrating the hood 20 in the radial direction. The pair of cut-outs 23 are located opposite to each other in the direction of the major axis 15a (see FIG. 2E) with the central axis 2a (or the male luer 10) disposed between them. Each cut-out 23 has an inverted "U" shape (see FIG. 2D), and a lower end thereof reaches the base 15. However, the cut-outs 23 do not reach the leading end 20a of the hood 20.

As is best shown in FIG. 2F, a pair of lock levers (hereinafter simply referred to as "levers") 30 are located opposite to each other in the direction of the major axis 15a (see FIG. 2E) with the central axis 2a disposed between them. The levers 30 are rectangular strip-shaped members that extend substantially parallel to the central axis 2a. The levers 30 are connected to the outer end edge of the base 15. Each lever 30 includes a locking portion 31 that is disposed on the same side (upper side) as the male luer 10 with respect to the base 15 and an operating portion 35 that is disposed on the opposite side (lower side) to the male luer 10 with respect to the base 15. A portion of each lever 30 which is located between the locking portion 31 and the operating portion 35 and to which the base 15 is connected is referred to as a lever base portion 39. The locking portions 31 each faces the male luer 10 and the operating portions 35 each faces the tubular portion 17.

The locking portions 31 are disposed within the respective cut-outs 23 that are formed in the hood 20. In other words, the locking portions 31 are surrounded by the respective inverted "U"-shaped slits 23 that penetrate the hood 20 in the radial direction (see FIG. 2D).

A claw 32 protrudes toward the male luer 10 from a surface (inner surface) of each locking portion 31 that faces the male luer 10. Each claw 32 includes an inclined surface 32a and an engagement surface 32b. The inclined surface 32a is inclined so that the distance from the male luer 10 increases as the distance from the base 15 increases. The engagement surface 32b is a flat surface that is disposed nearer to the base 15 than the inclined surface 32a and that is substantially parallel to a horizontal plane. As shown in FIG. 2E, when viewed from above, the top portion (portion that is nearest to the male luer 10) of each claw 32 protrudes toward the male luer 10 beyond the leading end 20a that surrounds the opening 21 of the hood 20.

As will be described later, when the male connector 1 is connected to a female connector 800, the claws 32 are engaged with the female connector 800 (see FIG. 11B, which will be described later). The levers 30 function as a "lever-type lock mechanism" that maintains the state in which the male connector 1 and the female connector 800 are connected to each other. In other words, the male connector 1 is a lever lock male connector.

Since the two levers 30 are disposed at respective positions that are symmetrical with respect to the central axis 2a (i.e., the male luer 10), the two claws 32 can be engaged with the female connector 800 at respective positions that are symmetrical with respect to the central axis 2a. Accordingly, the female connector 800 can be stably held, and thus the reliability of the lever-type lock mechanism is improved. The state in which the claws 32 are engaged with the female connector 800 is referred to as a "locked state".

Each lever 30 has a mechanical strength that is high enough for the entire lever 30 from the upper end (locking portion 31) to the lower end (operating portion 35) to be regarded as a substantially rigid body. In contrast, the mechanical strength of the base 15 that joins the base end portion 13 of the male luer 10 to each lever 30 is relatively low. Therefore, when a force F acting toward the central axis 2a is applied to the operating portions 35 as shown in FIG. 2F, the base 15 is elastically deformed and bent, thereby allowing the levers 30 to swing (or pivot) so that the locking portions 31 and the claws 32 formed on the respective locking portions 31 move away from the male luer 10 (in the directions of arrows A).

As shown in FIGS. 2B and 2G, a pair of holes 16 penetrating the base 15 in the vertical direction are formed in the base 15. The holes 16 are disposed on the minor axis 15b (see FIG. 2E) of the base 15 having a substantially elliptical shape.

As shown in FIG. 2A, the shape of the outer circumferential surface of the connector main body 2 that is located above the base 15 is a substantially curved surface that smoothly connects the circular shape of the leading end 20a of the hood 20 and the substantially elliptical shape at the position of the base 15. This curved surface is constituted by the outer circumferential surface of the hood 20 and the outer circumferential surfaces of the levers 30.

It is preferable that the connector main body 2 is made of a hard material. Specifically, a resin material such as polyacetal, polycarbonate, polystyrene, polyamide, polypropylene, or rigid polyvinyl chloride may be used. The connector main body 2 can be integrally produced as a single component through injection molding or the like using such a resin material.

1.2. Cover

Figure 3A:
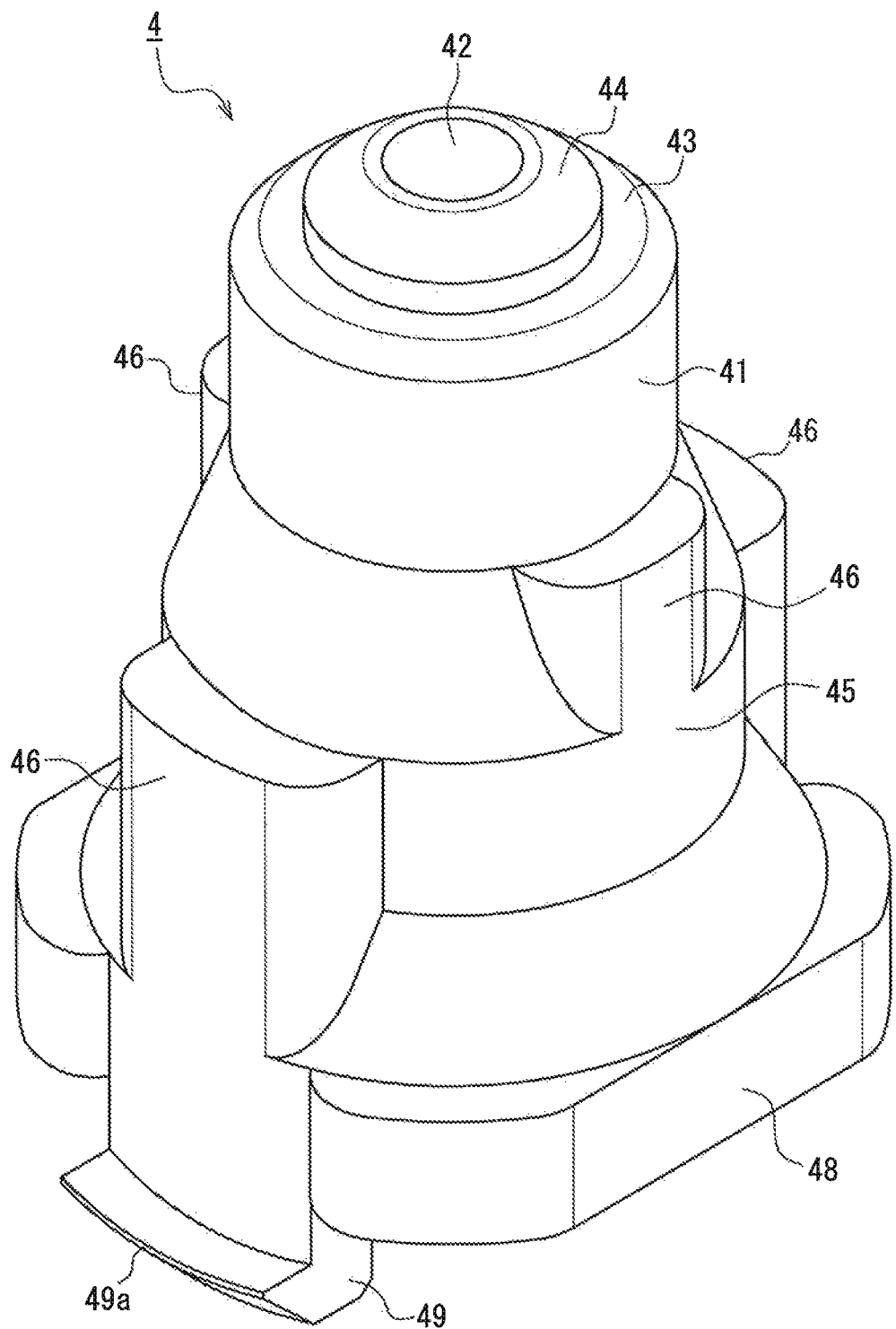
FIG. 3A is a perspective view of a cover of the male connector shown in FIG. 1 when viewed from above.
Figure 3B:
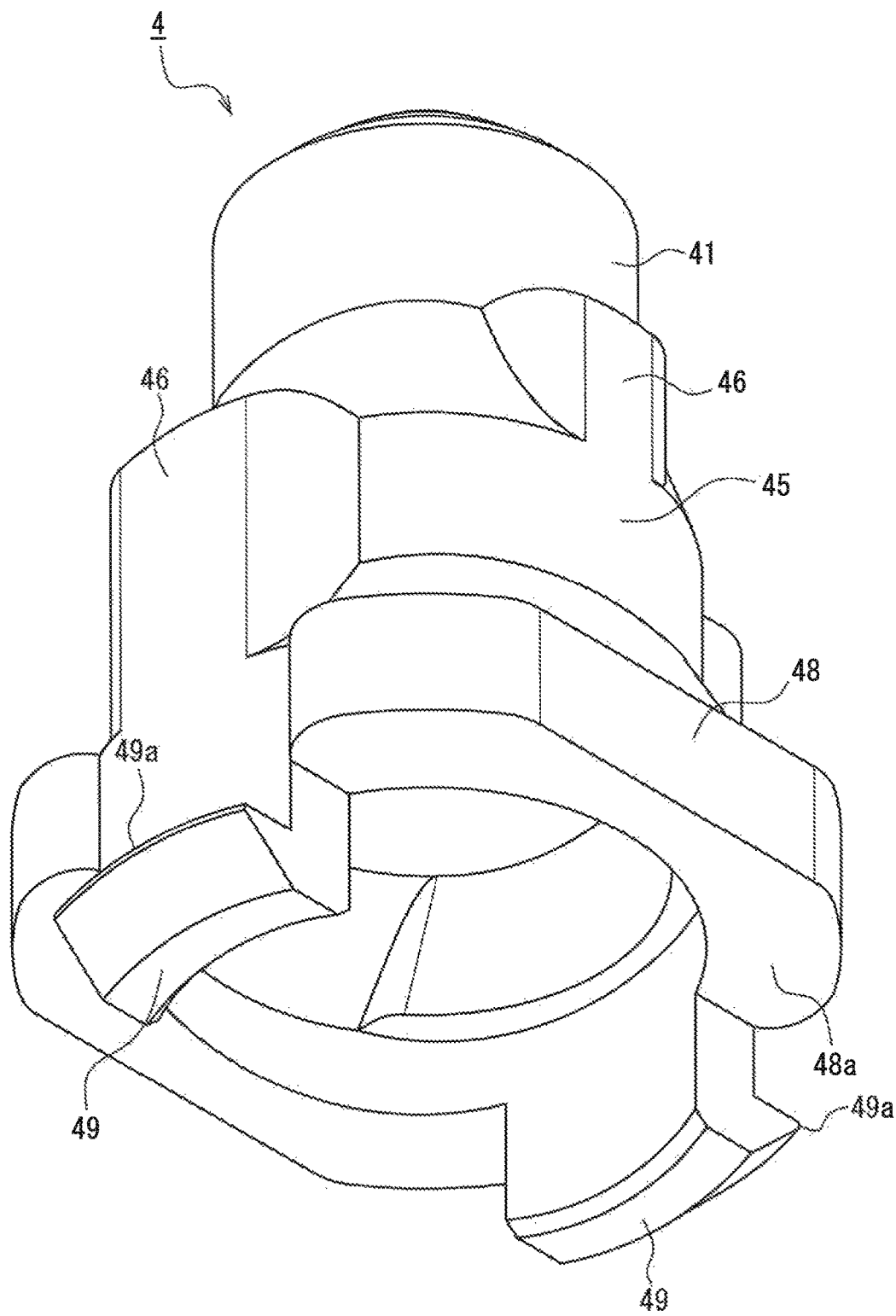
FIG. 3B is a perspective view of the cover when viewed from below.
Figure 3C:
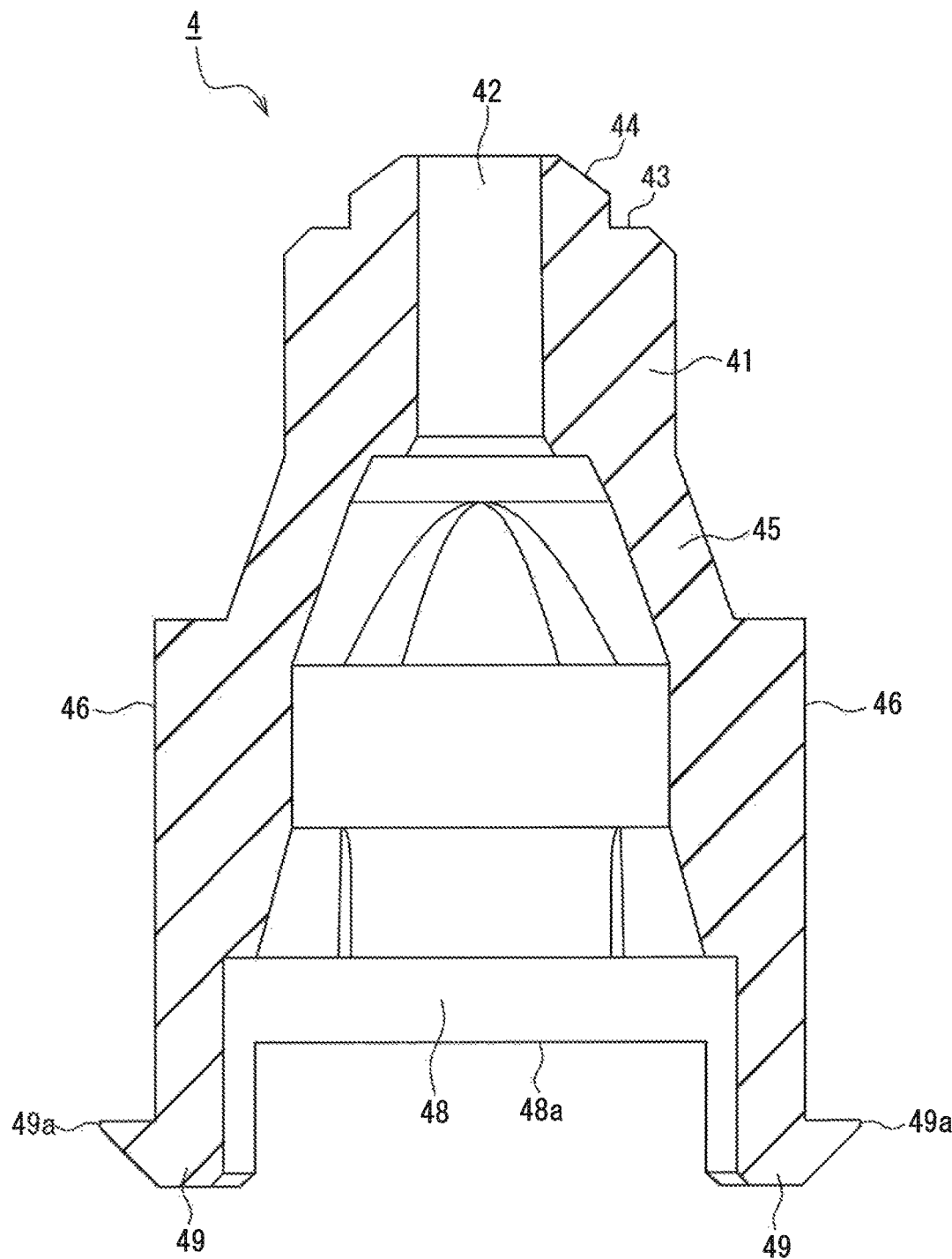
FIG. 3C is a cross-sectional view of the cover.

A cover 4 that constitutes the male connector 1 will be described below. FIG. 3A is a perspective view of the cover 4 when viewed from above, FIG. 3B is a perspective view of the cover 4 when viewed from below, and FIG. 3C is a cross-sectional view of the cover 4. The cover 4 includes a head portion 41, an outer circumferential wall 45, and a base portion 48 in this order from the top to the bottom. As shown in FIG. 3C, the cover 4 has a substantially tubular shape with a space penetrating the cover 4 in the vertical direction.

The cover 4 is integrally formed as a single component using a soft material (so-called elastomer) having rubber elasticity (or flexibility). The material for the cover 4 is not limited, and may be, e.g., isoprene rubber, silicone rubber, butyl rubber, or a thermoplastic elastomer.

As shown in FIG. 3C, a through hole 42 is formed penetrating the head portion 41 in the vertical direction. It is preferable that the inner circumferential surface of the through hole 42 has a shape that conforms to the outer circumferential surface of the male luer 10 so as to come into intimate contact with the outer circumferential surface of the male luer 10 of the connector main body 2. In this embodiment, the inner circumferential surface of the through hole 42 is a cylindrical surface whose internal diameter is constant with respect to the vertical direction. It is preferable that the internal diameter of the through hole 42 is equal to or slightly smaller than the external diameter of the male luer 10 of the connector main body 2.

As shown in FIG. 3A, a dome-shaped protrusion 44 that protrudes upward is provided in a circular area in the middle of an upper surface 43 of the head portion 41. The through hole 42 is open in the center of the protrusion 44. The upper surface 43 of the head portion 41, which surrounds the protrusion 44, constitutes an annular flat surface that is parallel to the horizontal direction.

When a compressive force in the vertical direction is applied to the cover 4, the outer circumferential wall 45 is elastically and compressively deformed so that its vertical dimension is reduced (see FIG. 11B, which will be described later). As shown in FIG. 3C, the outer circumferential wall 45 has a larger internal diameter than the through hole 42 of the head portion 41. When the cover 4 is attached to the connector main body 2, the outer circumferential wall 45 is spaced apart from the male luer 10 in the radial direction (see FIGS. 4B and 4C, which will be described later). Thus, it is less likely that the inner circumferential surface of the outer circumferential wall 45 will collide with the male luer 10 when the outer circumferential wall 45 is compressively deformed in the vertical direction. This is advantageous in increasing the amount of compressive deformation of the outer circumferential wall 45 in the vertical direction.

Moreover, the outer circumferential wall 45 has tapered (conical) portions and cylindrical portions that are alternately arranged in the vertical direction. In the tapered portions, the external and internal diameters of the outer circumferential wall 45 increase as the distance from the head portion 41 increases. In the cylindrical portions, the external and internal diameters of the outer circumferential wall 45 are constant with respect to the vertical direction. Thus, the outer circumferential wall 45 as a whole has a conical shape that becomes gradually narrower toward the head portion 41. When a compressive force in the vertical direction is applied to the cover 4, this shape allows the outer circumferential wall 45 to be deformed so that the tapered portions are depressed into the cylindrical portions directly under the respective tapered portions (see FIG. 11B, which will be described later). This is advantageous in increasing the amount of compressive deformation of the outer circumferential wall 45 in the vertical direction.

Rib-shaped projections 46 are provided on the outer surface of the outer circumferential wall 45 in the vertical direction. The rib-shaped projections 46 protrude outward from the outer circumferential wall 45 and locally increase the thickness (i.e., the radial dimension) of the outer circumferential wall 45. The rib-shaped projections 46 prevent buckling deformation of the outer circumferential wall 45 when a compressive force in the vertical direction is applied to the cover 4.

The base portion 48 has a flat bottom surface 48a. A pair of fixing projections 49 protrude downward from the bottom surface 48a. A fixing claw 49a protrudes outward from the outer surface of each fixing projection 49. The fixing projections 49 and the fixing claws 49a are used to fix the cover 4 to the connector main body 2.

1.3. Assembling of Male Connector

Figure 4A:
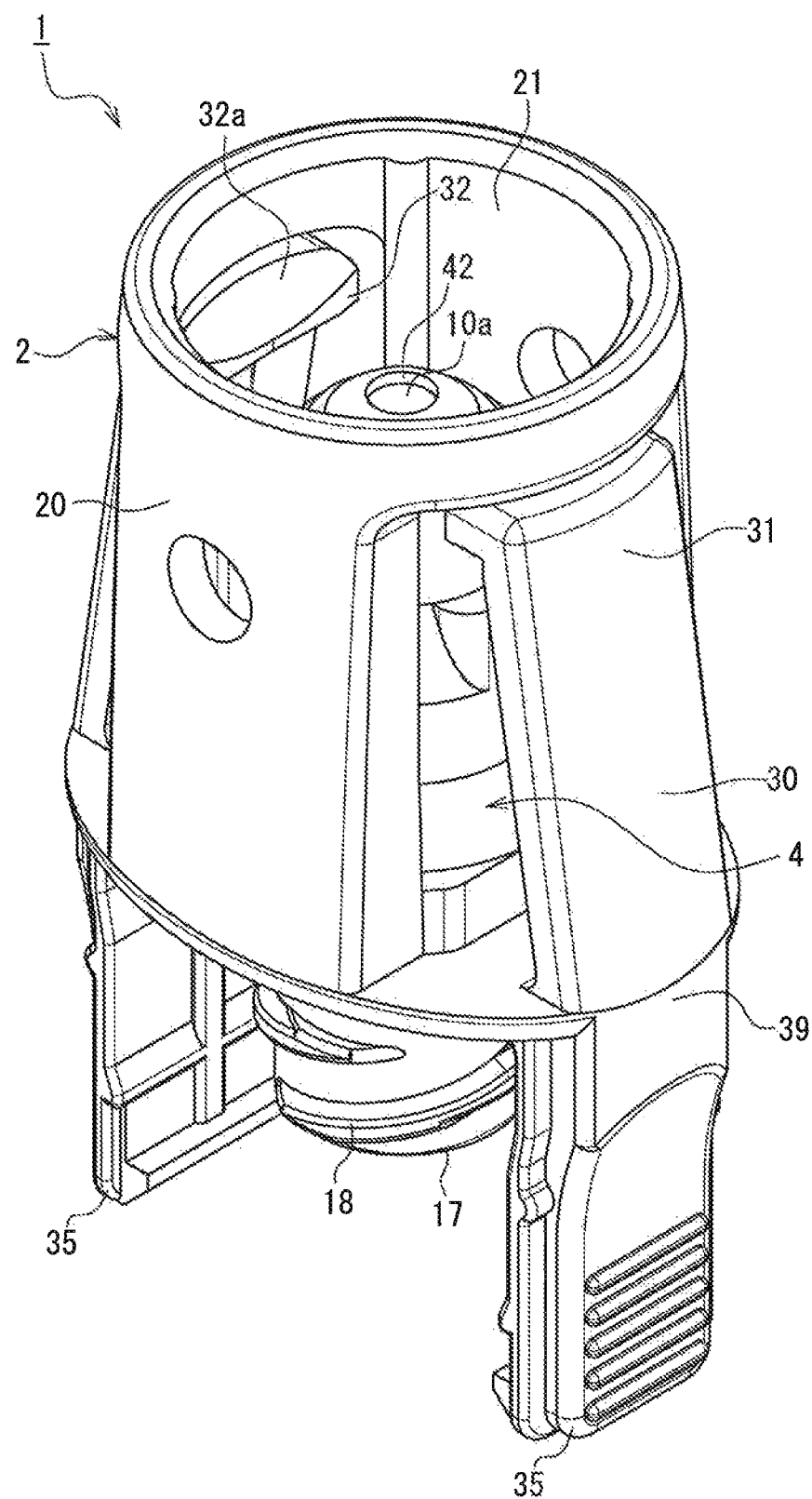
FIG. 4A is a perspective view of the male connector shown in FIG. 1 when viewed from above.
Figure 4B:
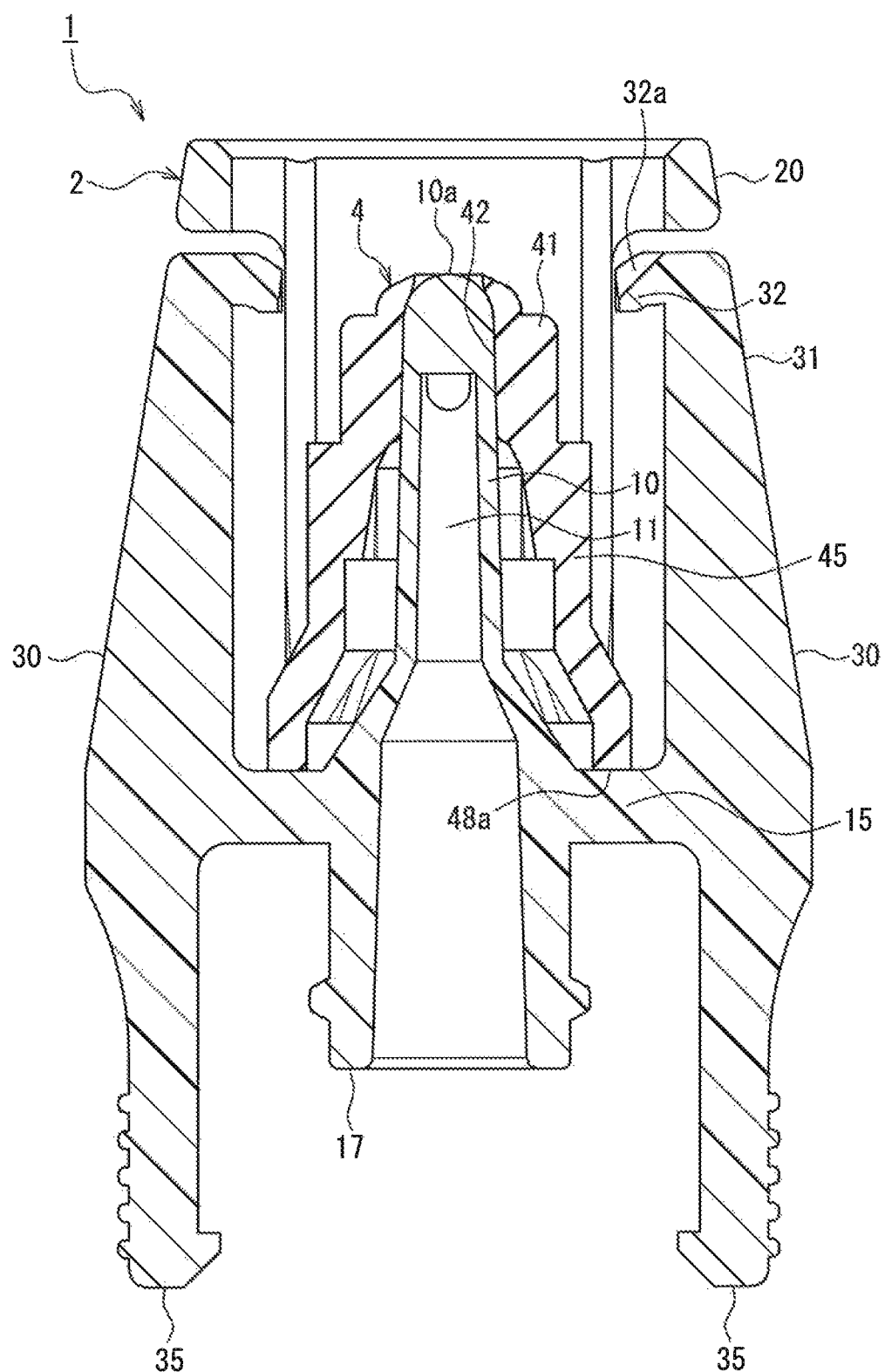
FIG. 4B is a cross-sectional view of the male connector.
Figure 4C:
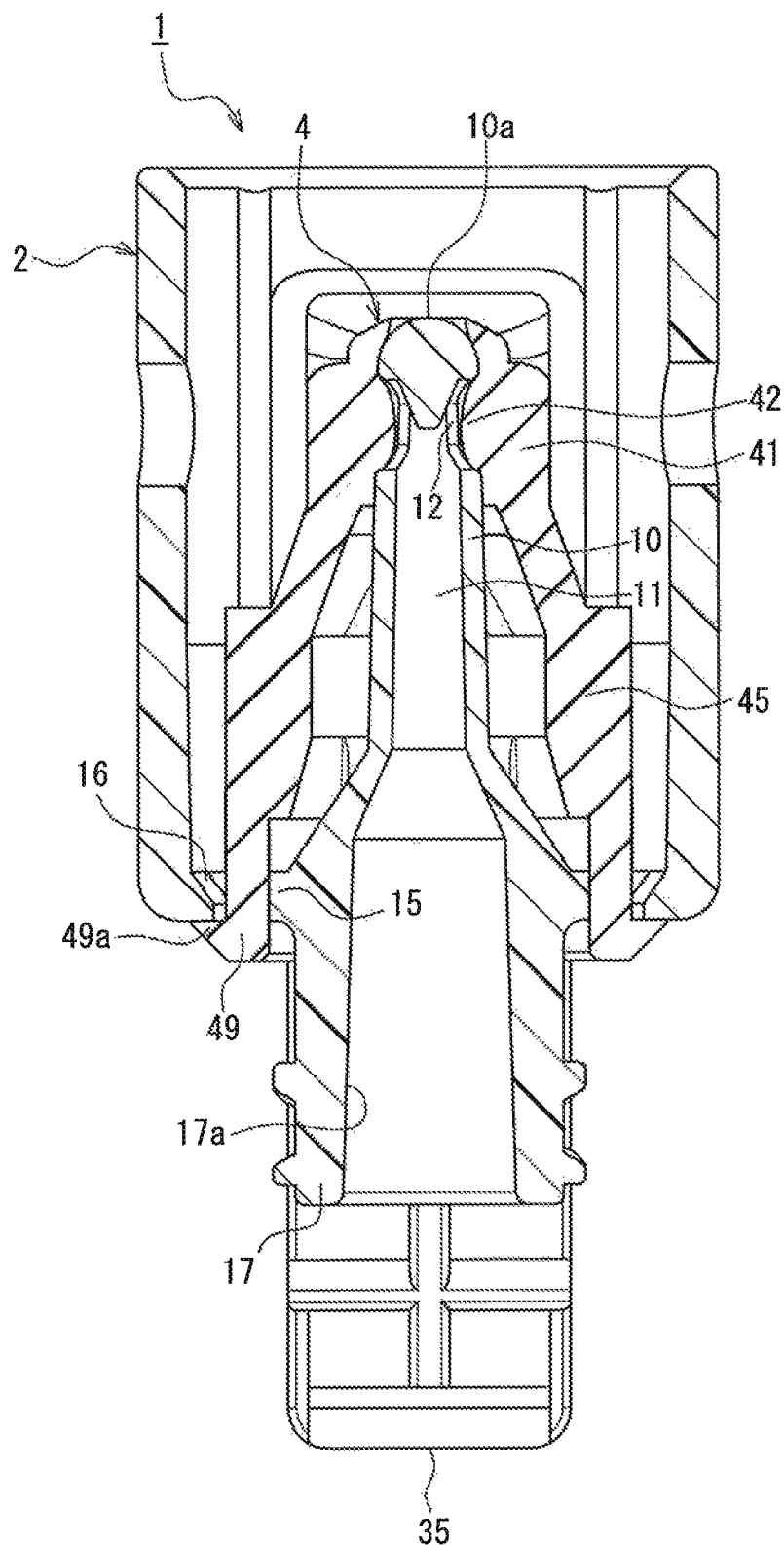
FIG. 4C is another cross-sectional view of the male connector.

As shown in FIG. 1, the cover 4 is inserted into the hood 20 from above the connector main body 2. FIG. 4A is a perspective view of the male connector 1 when viewed from above, with the cover 4 attached to the connector main body 2. FIG. 4B is a cross-sectional view of the male connector 1 taken along a plane containing the central axis 2a and the major axis 15a (see FIG. 2E). FIG. 4C is a cross-sectional view of the male connector 1 taken along a plane containing the central axis 2a and the minor axis 15b (see FIG. 2E).

As shown in FIG. 4C, the fixing projections 49 of the cover 4 are inserted into the respective holes 16 that are provided in the base 15 of the connector main body 2. The fixing claws 49a have passed through the holes 16 and are engaged with the lower surface of the base 15. The bottom surface 48a of the cover 4 is in intimate contact with the upper surface of the base 15 (see FIG. 4B).

The leading end 10a and its neighboring portion of the male luer 10 are inserted into the through hole 42 of the head portion 41 of the cover 4. The leading end 10a of the male luer 10 is exposed in the through hole 42 of the head portion 41. The inner circumferential surface of the through hole 42 is appropriately deformed in accordance with the external shape of the outer circumferential surface of the male luer 10 and is in intimate contact with that outer circumferential surface. The openings of the lateral holes 12 of the male luer 10 are closed off in a liquid-tight manner by the inner circumferential surface of the through hole 42.

The outer circumferential wall 45 of the cover 4 is spaced apart from the male luer 10 in the radial direction. Thus, a liquid-tight space is formed between the cover 4 and the connector main body 2. Moreover, the outer circumferential wall 45 is spaced apart from both the hood 20 and the levers 30 in the radial direction.

In the present invention, as shown in FIGS. 4A to 4C, a state in which substantially no external force acts on the levers 30, and the cover 4 is not compressively deformed in the vertical direction is referred to as the "initial state" of the male connector 1. The shape of the cover 4 in the initial state is referred to as an "initial shape".

2. Screw Lock Connector
2.1. Luer Main Body

Figure 5A:
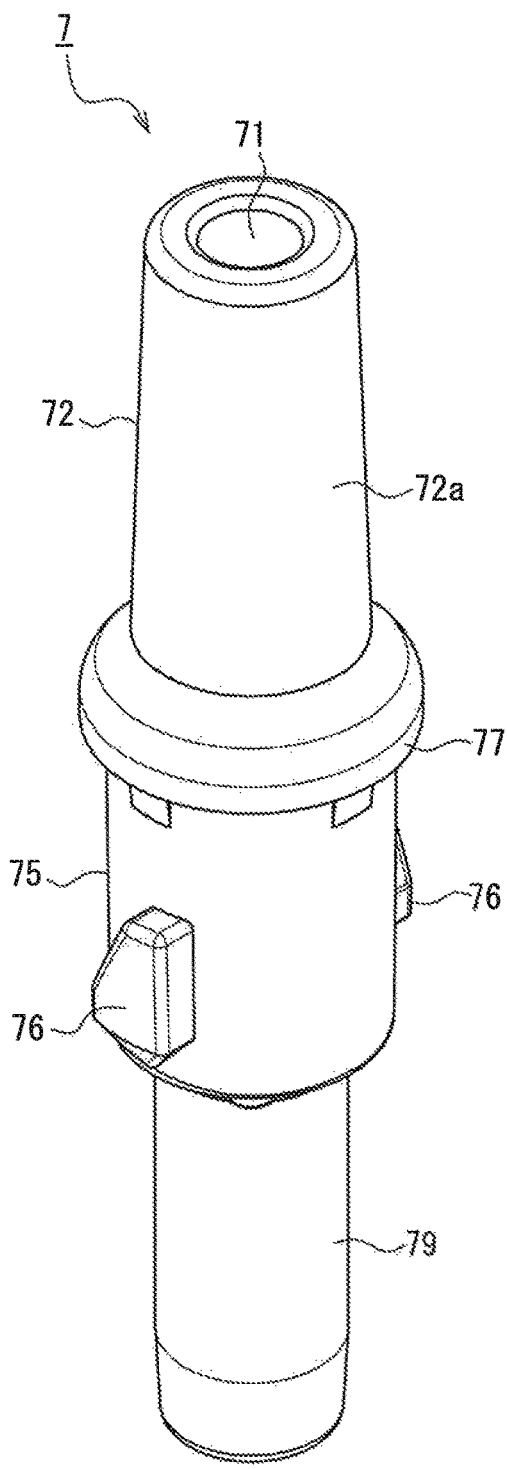
FIG. 5A is a perspective view of a luer main body shown in FIG. 1.
Figure 5B:
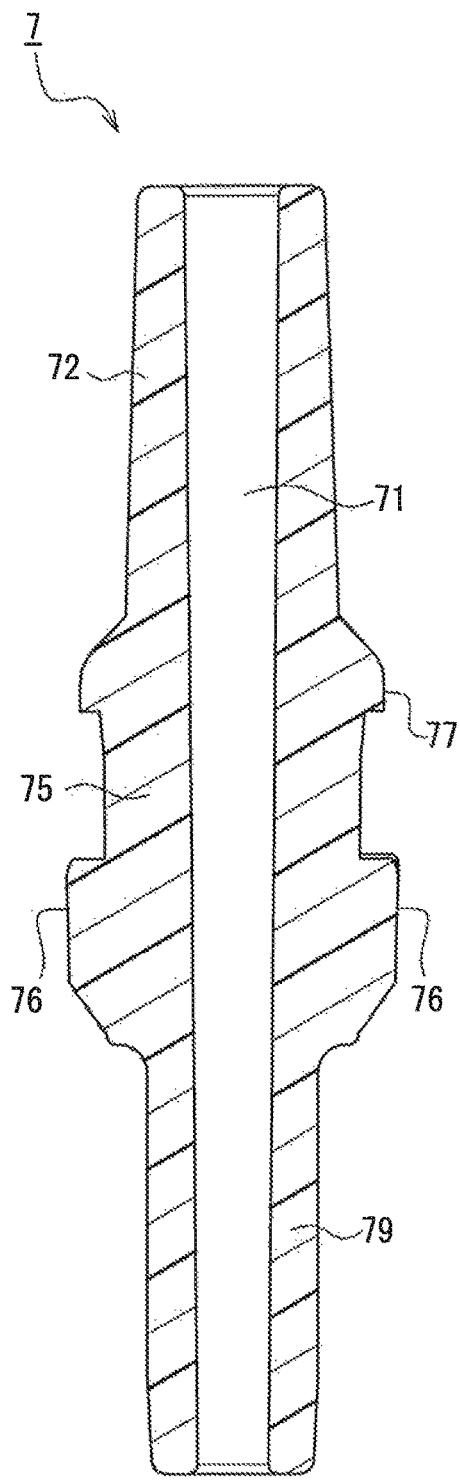
FIG. 5B is a cross-sectional view of the luer main body.

A luer main body 7 that constitutes a screw lock connector 6 will be described below. FIG. 5A is a perspective view of the luer main body 7, and FIG. 5B is a cross-sectional view of the luer main body 7.

The luer main body 7 has a substantially cylindrical shape as a whole, in which a through hole (flow channel) 71 along the longitudinal direction of the luer main body 7 is formed. The luer main body 7 includes a male luer 72, a tubular portion 75, and a connecting portion 79 in this order from the top to the bottom.

An outer circumferential surface 72a of the male luer 72 is a male tapered surface (e.g., a 6% tapered surface) whose external diameter gradually decreases toward the leading end. The outer circumferential surface of the tubular portion 75 is a cylindrical surface whose external diameter is constant with respect to the vertical direction. A pair of protruding portions 76 protrude outward from the outer circumferential surface of the tubular portion 75. An annular projection 77 continuously extending in the circumferential direction is provided at the boundary between the male luer 72 and the tubular portion 75. The annular projection 77 has an external diameter that is larger than those of the male luer 72 and the tubular portion 75.

It is preferable that the luer main body 7 is made of a hard material. Specifically, a resin material such as polyacetal, polycarbonate, polystyrene, polyamide, polypropylene, or rigid polyvinyl chloride may be used. The luer main body 7 can be integrally produced as a single component through injection molding or the like using such a resin material.

2.2 Lock Nut

Figure 6A:
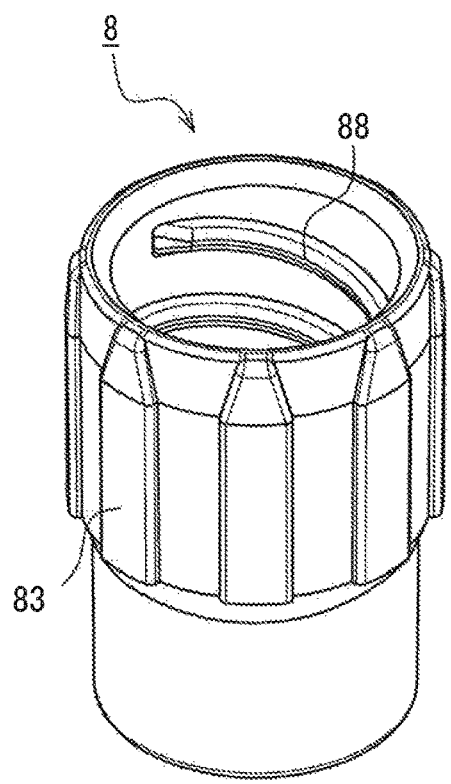
FIG. 6A is a perspective view of a lock nut shown in FIG. 1 when viewed from above.
Figure 6B:
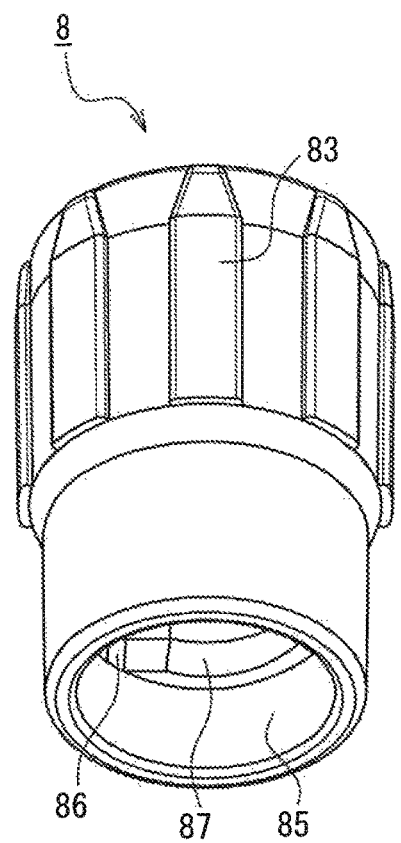
FIG. 6B is a perspective view of the lock nut when viewed from below.
Figure 6C:
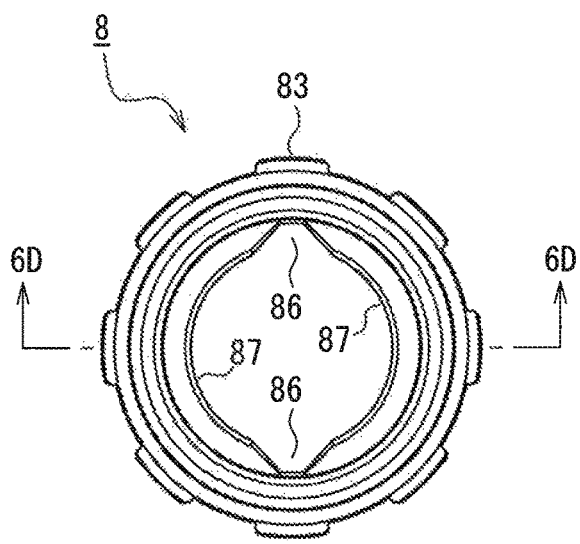
FIG. 6C is a plan view of the lock nut.
Figure 6D:
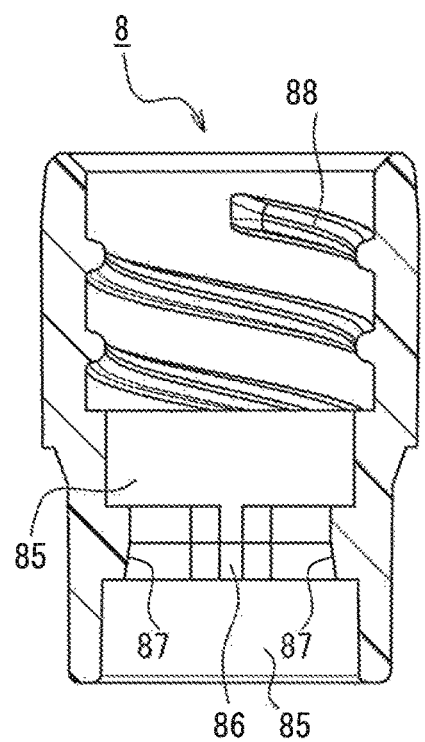
FIG. 6D is a cross-sectional view of the lock nut.

A lock nut 8 that constitutes the screw lock connector 6 will be described below. FIG. 6A is a perspective view of the lock nut 8 when viewed from above, FIG. 6B is a perspective view of the lock nut 8 when viewed from below, FIG. 6C is a plan view of the lock nut 8, and FIG. 6D is a cross-sectional view of the lock nut 8. The lock nut 8 has a hollow, substantially cylindrical shape as a whole.

The outer circumferential surface of the lock nut 8 is constituted by two cylindrical surfaces having different external diameters. A plurality of ribs 83 protrude outward from the upper cylindrical surface having a relatively large external diameter. The ribs 83 extend in the vertical direction. In this embodiment, the outer circumferential surface of the lock nut 8 is constituted by the two cylindrical surfaces; however, the present invention is not limited thereto. For example, the entire outer circumferential surface from the upper end to the lower end may be constituted by a single cylindrical surface. Alternatively, the outer circumferential surface may contain a surface (e.g., a polygonal prism-shaped surface) other than a cylindrical surface. The ribs 83 may be omitted.

A female thread 88 is formed on the inner circumferential surface of the lock nut 8. The female thread 88 extends in a region from the upper end to the substantially middle of the inner circumferential surface of the lock nut 8. A portion of the inner circumferential surface of the lock nut 8 that is located below the female thread 88 constitutes a cylindrical surface 85 having a constant internal diameter. A position-restricting projection 87 extending in the circumferential direction protrudes from the cylindrical surface 85. A pair of guide passages 86 cut across the position-restricting projection 87. The guide passages 86 extend in the vertical direction. The guide passages 86 divide the position-restricting projection 87 in the circumferential direction.

It is preferable that the lock nut 8 is made of a hard material. Specifically, a resin material such as polyacetal, polycarbonate, polystyrene, polyamide, polypropylene, or rigid polyvinyl chloride may be used. The lock nut 120 can be integrally produced as a single component through injection molding or the like using such a resin material.

2.3. Assembling of Screw Lock Connector

Figure 7A:
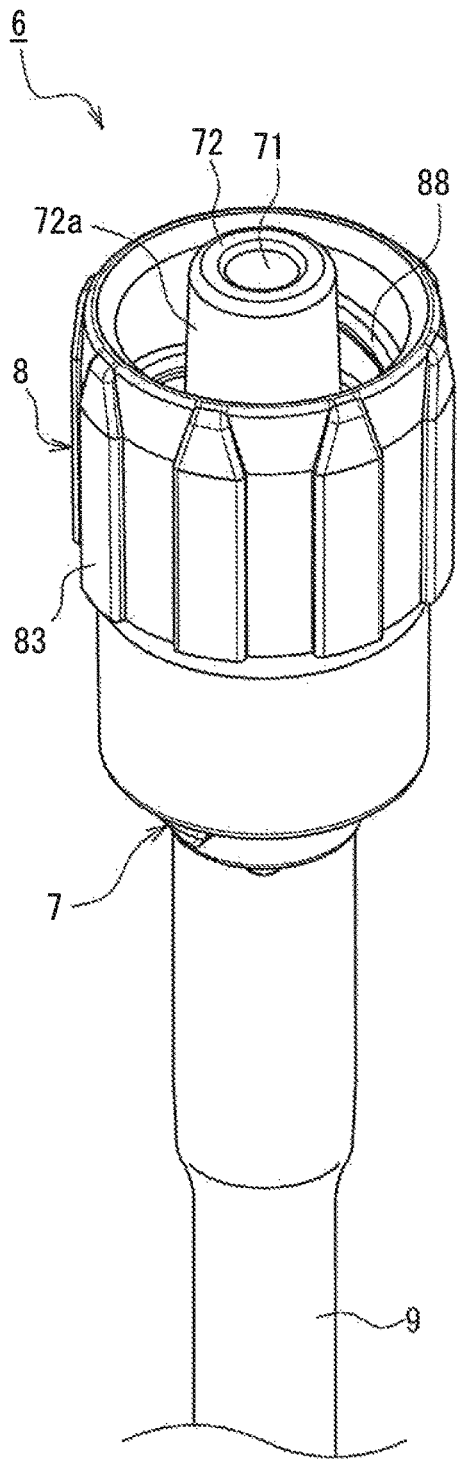
FIG. 7A is a perspective view of a screw lock connector when viewed from above.

As shown in FIG. 1, a flexible tube 9 is passed through the lock nut 8. Then, the connecting portion 79 of the luer main body 7 is inserted into the upper end of the tube 9. Subsequently, the lock nut 8 is moved upward. The luer main body 7 is inserted into the inside of the female thread 88 of the lock nut 8. The protruding portions 76 that protrudes from the outer circumferential surface of the luer main body 7 may possibly collide with the position-restricting projection 87 that protrudes from the inner circumferential surface of the lock nut 8. If this is the case, the lock nut 8 is slightly rotated relative to the luer main body 7. When the positions of the protruding portions 76 of the luer main body 7 with respect to the circumferential direction coincide with the positions of the respective guide passages 86 of the lock nut 8 with respect to the circumferential direction, the protruding portions 76 can pass through the guide passages 86. In this manner, the screw lock connector 6 can be assembled as shown in FIGS. 7A and 7B.

Figure 7B:
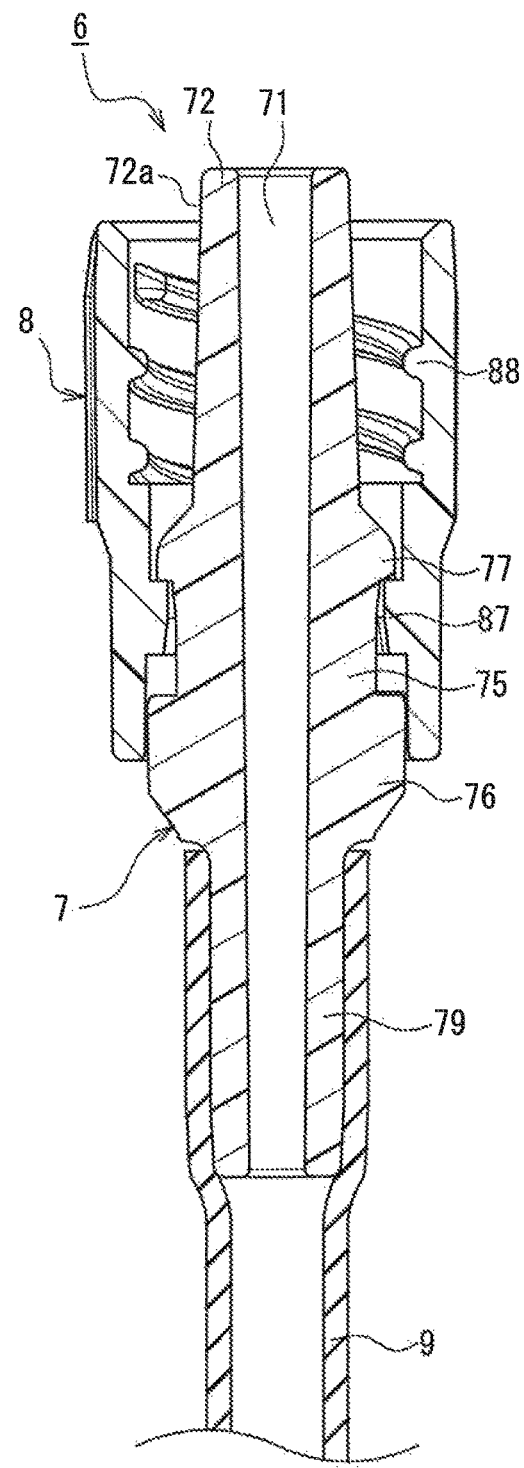
FIG. 7B is a cross-sectional view of the screw lock connector.

As shown in FIG. 7B, the position-restricting projection 87 of the lock nut 8 is located between the annular projection 77 and the protruding portions 76 of the luer main body 7. Due to the position-restricting projection 87 colliding with the annular projection 77 and the protruding portions 76, the lock nut 8 is restricted from moving upward (toward the male luer 72) and downward (toward the connecting portion 79) relative to the luer main body 7. However, the lock nut 8 can freely rotate around the luer main body 7.

3. Connection of Male Connector and Screw Lock Connector

The male connector 1 (FIGS. 4A to 4C) and the screw lock connector 6 (FIGS. 7A and 7B) can be connected to each other by inserting the male luer 72 of the luer main body 7 into the tubular portion 17 of the connector main body 2 and screwing the female thread 88 of the lock nut 8 onto the male thread 18 of the tubular portion 17.

Figure 8A:
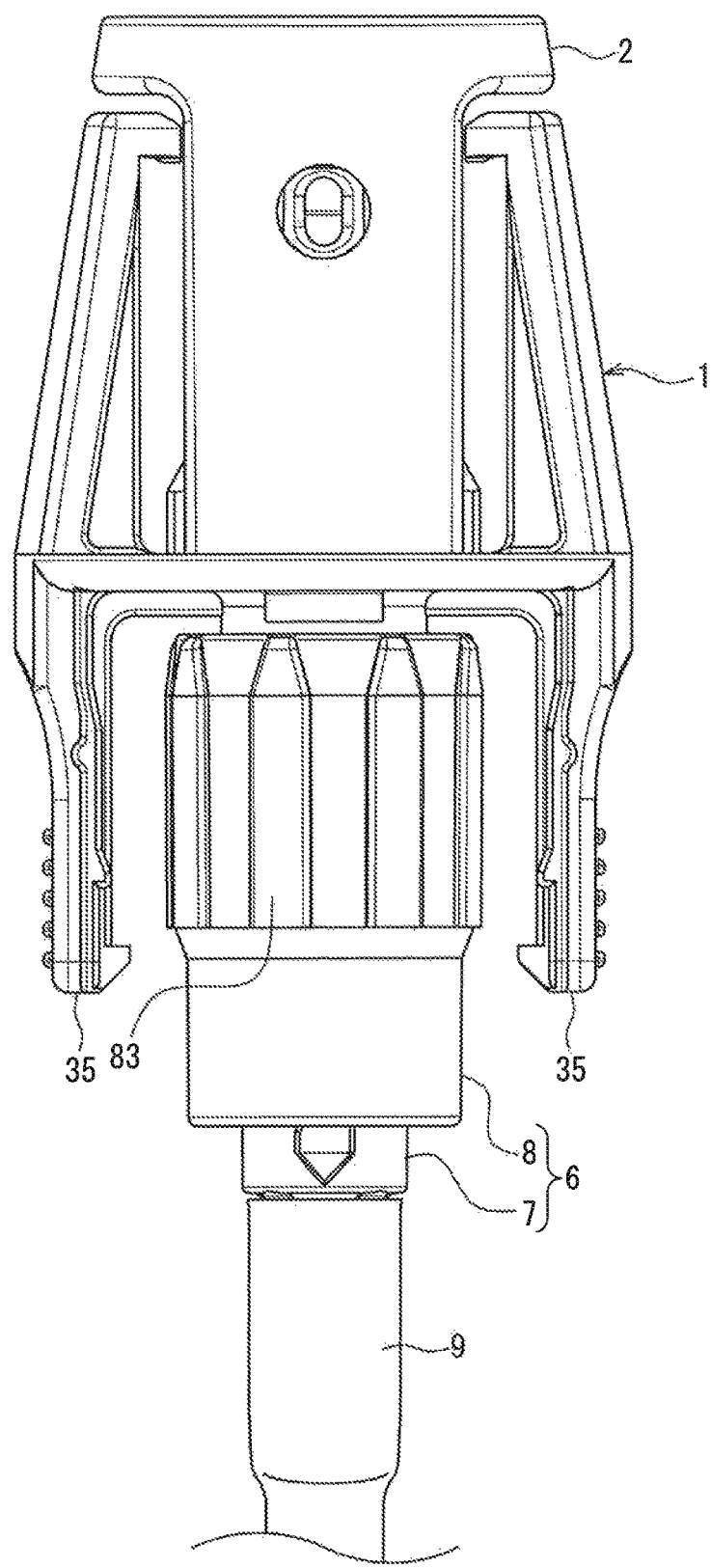
FIG. 8A is a side view showing a state in which the male connector and the screw lock connector are connected to each other.
Figure 8B:
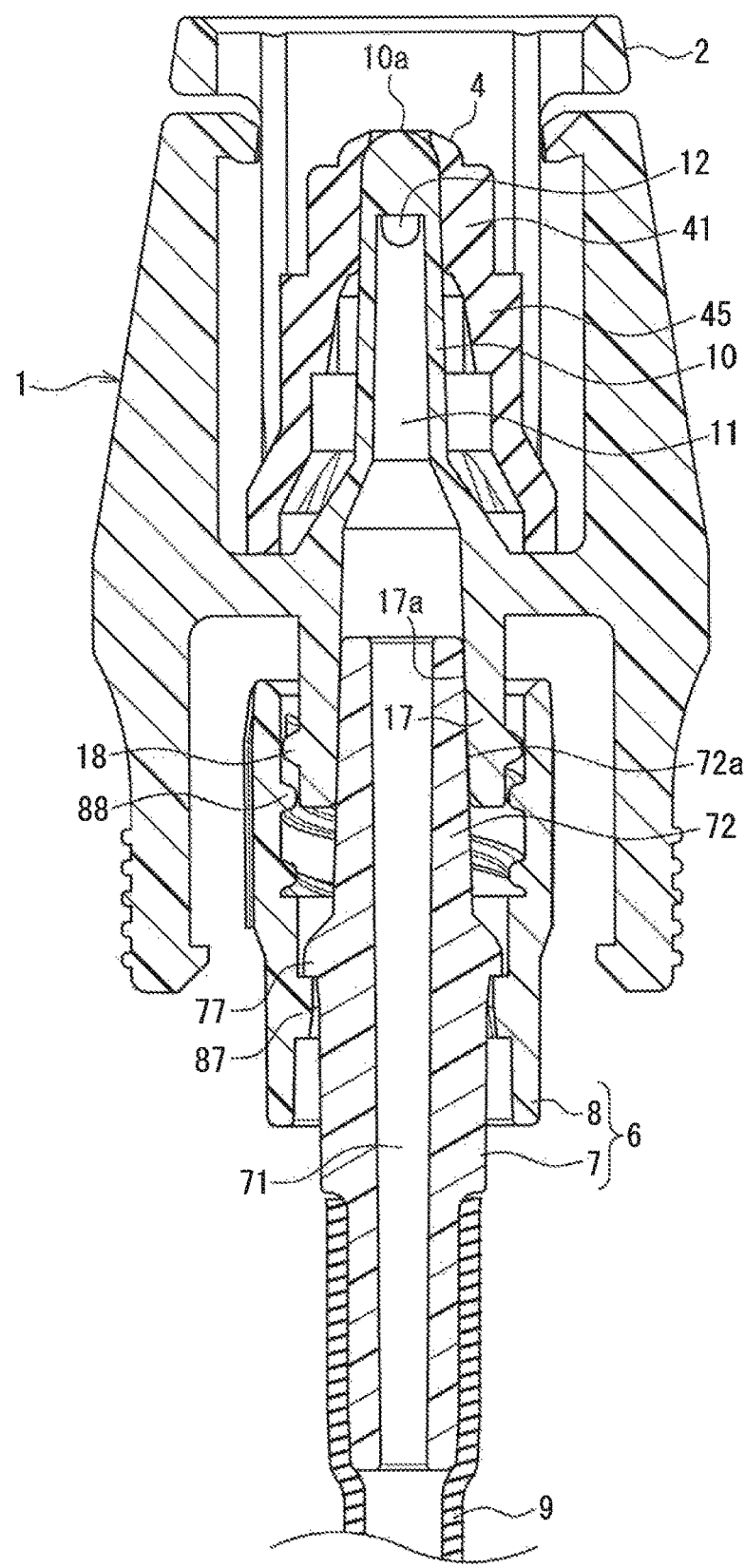
FIG. 8B is a cross-sectional view showing a state in which the male connector and the screw lock connector are connected to each other.

FIG. 8A is a side view showing a state in which the male connector 1 and the screw lock connector 6 are connected to each other, and FIG. 8B is a cross-sectional view showing this state.

The outer circumferential surface 72a of the male luer 72 and the inner circumferential surface 17a of the tubular portion 17 are tapered surfaces having the same diameter and taper angle. Accordingly, as shown in FIG. 8B, the outer circumferential surface 72a and the inner circumferential surface 17a come into intimate contact with each other in a liquid-tight manner. Thus, the tube 9 and the flow channel 11 of the male luer 10 are in communication with each other.

The female thread 88 of the lock nut 8 and the male thread 18 of the tubular portion 17 are screwed together. Moreover, the position-restricting projection 87 of the lock nut 8 and the annular projection 77 of the luer main body 7 are engaged with each other. Thus, the male luer 72 and the tubular portion 17 are securely connected to each other. Even when an unintentional pull force acts between the male connector 1 (or the connector main body 2) and the screw lock connector 6 (or the luer main body 7), the male connector 1 and the screw lock connector 6 will not be disconnected from each other.

As shown in FIG. 8A, the lock nut 8 is disposed between the pair of operating portions 35. It is possible to rotate the lock nut 8 while using the ribs 83, which are formed on the outer circumferential surface of the lock nut 8, as an anti-slipping structure, to screw or unscrew the female thread 88 onto or from the male thread 18.

4. Female Connector

Figure 9A:
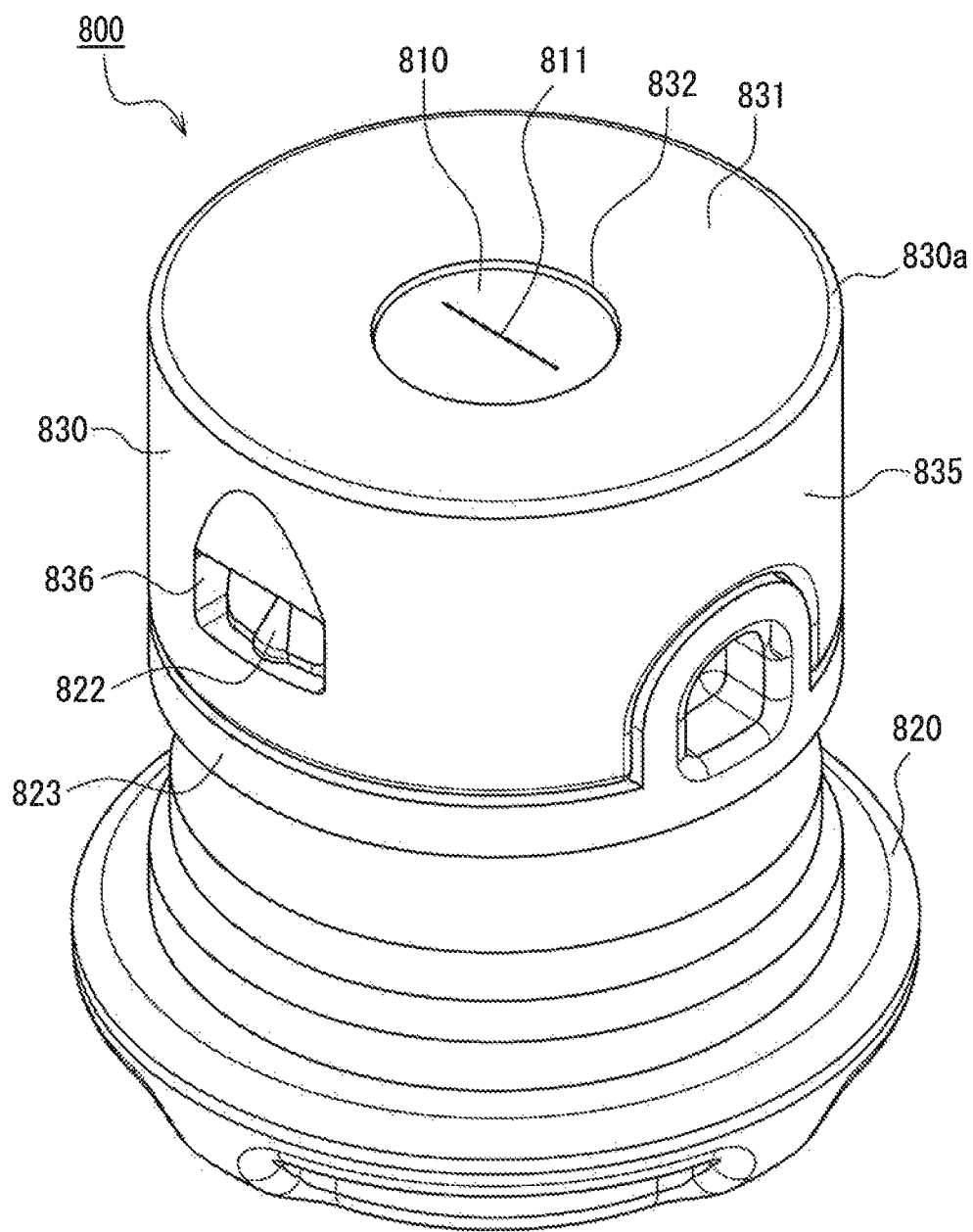
FIG. 9A is a perspective view of a female connector to be connected to the male connector.
Figure 9B:
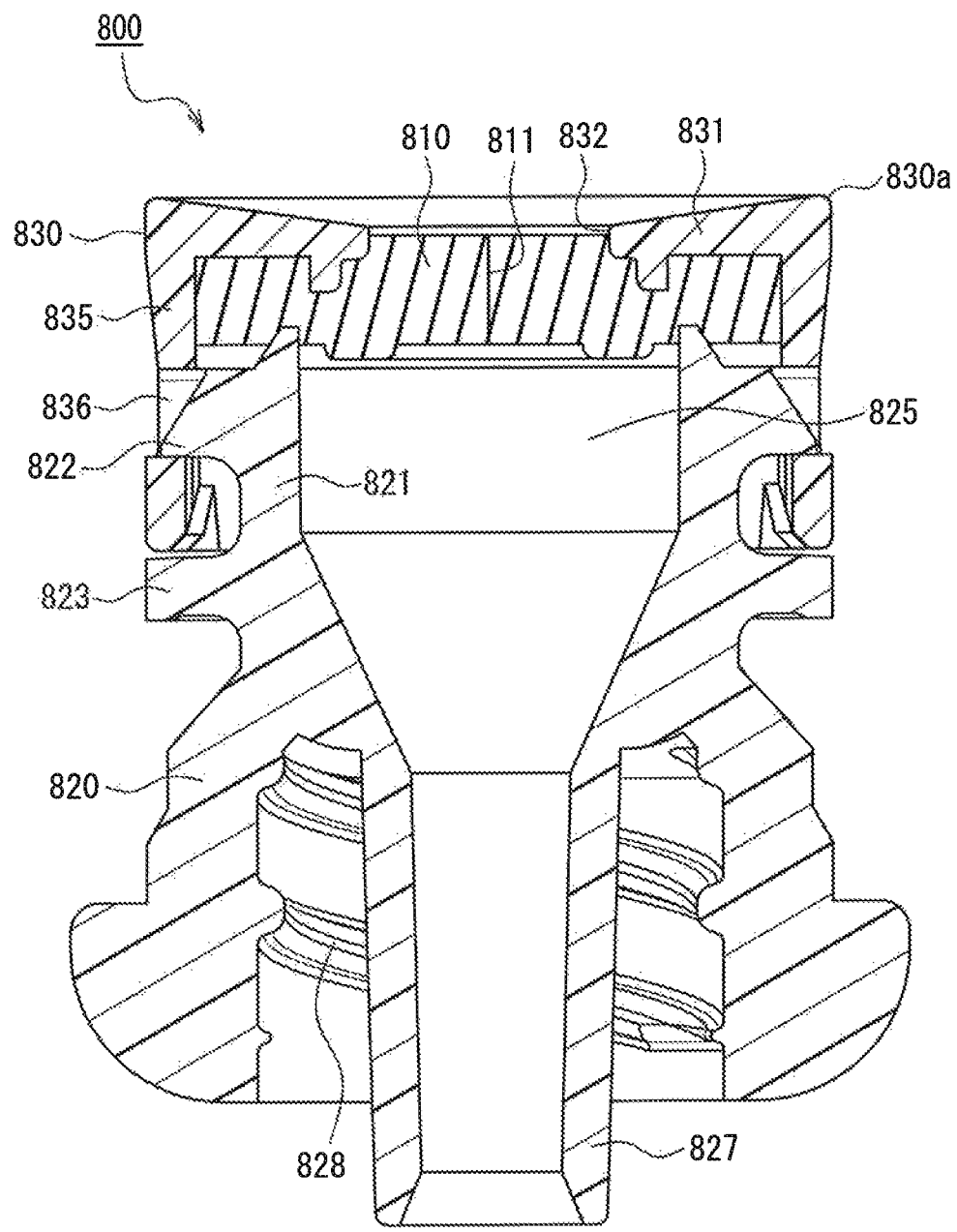
FIG. 9B is a cross-sectional view of the female connector.

The male connector 1 is used by being connected to a female connector. FIGS. 9A and 9B show an example of the female connector. FIG. 9A is a perspective view of the female connector 800, and FIG. 9B is a cross-sectional view of the female connector 800.

The female connector 800 includes a disk-like partition member (hereinafter referred to as "septum") 810 as well as a mount 820 and a cap 830 that sandwich and fix the septum 810 in the vertical direction.

A straight line-shaped slit (cut portion) 811 penetrating the septum 810 in the vertical direction is formed at the center of the septum 810. The material for the septum 810 is not limited, but a soft material having rubber elasticity is preferable, and for example, isoprene rubber, silicone rubber, butyl rubber, a thermoplastic elastomer, and the like can be used.

The mount 820 includes, in the upper portion thereof, a seat 821 having a substantially cylindrical shape. The outer circumferential surface of the seat 821 is a cylindrical surface. A pair of engagement claws 822 and an annular projection 823 protrude outward form the outer circumferential surface of the seat 821. The annular projection 823 is slightly spaced downward from the engagement claws 822.

A male luer 827 that is in communication with a cavity 825 of the seat 221 and a female thread 828 that is coaxial with the male luer 827 are provided below the seat 821. The outer circumferential surface of the male luer 827 is a male tapered surface (conical surface) whose external diameter gradually decreases toward the leading end (i.e., the external diameter decreases as the distance from the seat 821 increases).

The cap 830 includes a top plate 831 having a disk shape, and a peripheral wall 835 extending downward from the outer circumferential end edge of the top plate 831 and having a cylindrical shape. A circular opening (through hole) 832 is formed at the center of the top plate 831. A pair of engagement holes 836 are formed in the peripheral wall 835. The engagement holes 836 are through holes that penetrate the peripheral wall 835 in the radial direction.

As shown in FIG. 9B, the septum 810 is placed on the upper end of the seat 821, and the septum 810 is covered with the cap 830 from above. The engagement claws 822 formed on the seat 821 are fitted in the respective engagement holes 836 formed in the cap 830, and thus the cap 830 is engaged with the engagement claws 822. As a result, the cap 830 is fixed to the mount 820 (see FIG. 9A). The septum 810 is sandwiched between the upper end of the seat 821 and the top plate 831 of the cap 830 in the thickness direction (i.e., vertical direction). The slit 811 of the septum 810 is exposed in the opening 832 that is formed in the top plate 831. The annular projection 823 formed on the mount 820 is located below and adjacent to the peripheral wall 835 of the cap 830. A top surface of the annular projection 823 constitutes a cylindrical surface that is substantially the same as the outer circumferential surface of the peripheral wall 835.

The female connector 800 including the septum 810 in which the slit 811 is formed is generally called a needleless port (see, e.g., Patent Document 6).

5. Connection and Disconnection of Male Connector and Female Connector, and Method for Using the Same The male connector 1 and the female connector 800 constitute a coupling portion of an extracorporeal circuit. The male connector 1 and the female connector 800 can be connected to each other in the following manner.

Figure 10:
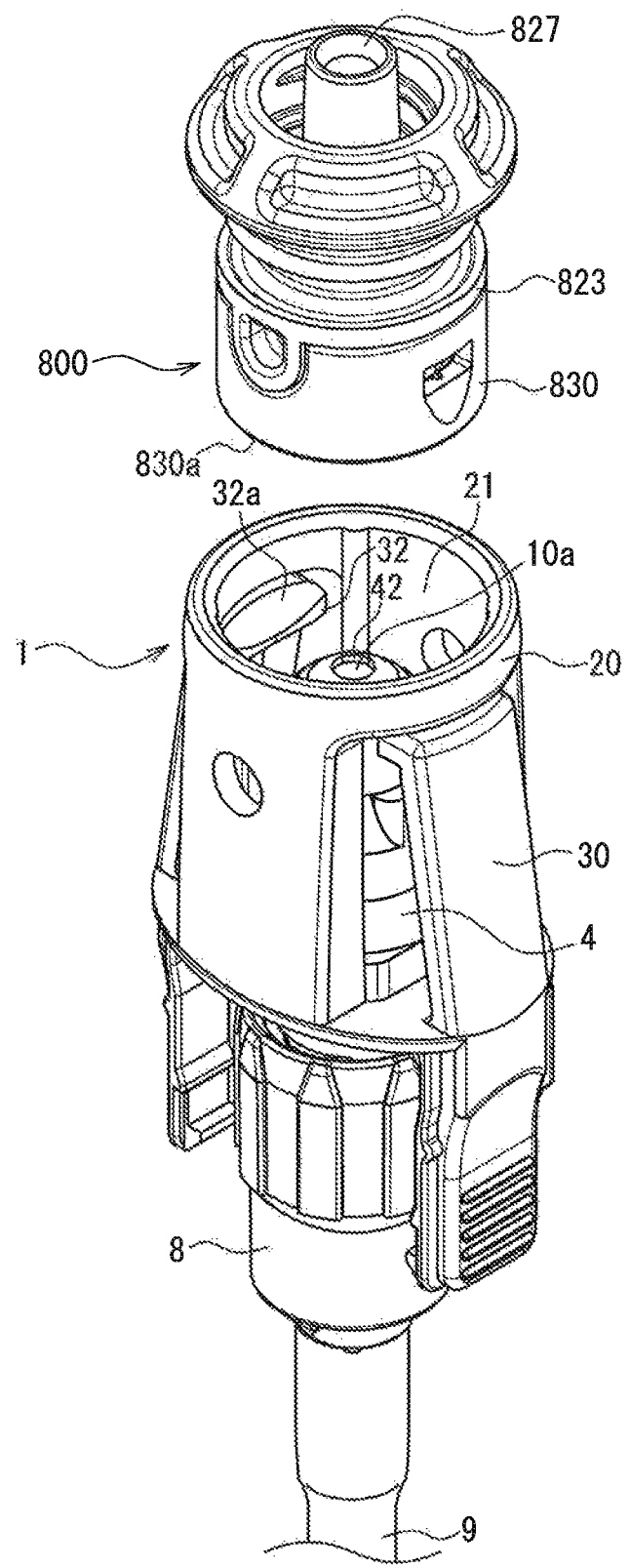
FIG. 10 is a perspective view showing the male connector and the female connector immediately before they are connected.

First, as shown in FIG. 10, the male connector 1 and the female connector 800 are located opposite to each other. Although not shown in the drawings, a flexible tube is connected to the male luer 827 of the female connector 800 directly or indirectly via a certain member.

From the state shown in FIG. 10, the cap 830 of the female connector 800 is inserted into the hood 20 of the male connector 1, and is pushed inward.

An outer end edge 830a (see FIGS. 9A and 9B) of the top plate 831 of the cap 830 abuts against the inclined surfaces 32a (see FIGS. 2E, 2F, 4A, and 4B) of the claws 32 of the levers 30. When the female connector 800 is pushed further into the hood 20, the end edge 830a elastically displaces (swings) the levers 30 so that the claws 32 move away from the male luer 10.

In parallel with this, the leading end 10a (see FIG. 4A) of the male luer 10 abuts against the septum 810 (see FIG. 9A) that is exposed in the opening 832 of the cap 830, and subsequently advances into the slit 811 of the septum 810. Almost simultaneously, the head portion 41 of the cover 4 abuts against the septum 810 or the top plate 831 of the cap 830. As the male luer 10 advances further into the septum 810, the cover 4 is compressed in the vertical direction, and the outer circumferential wall 45 is deformed so that its vertical dimension is reduced.

Figure 11A:
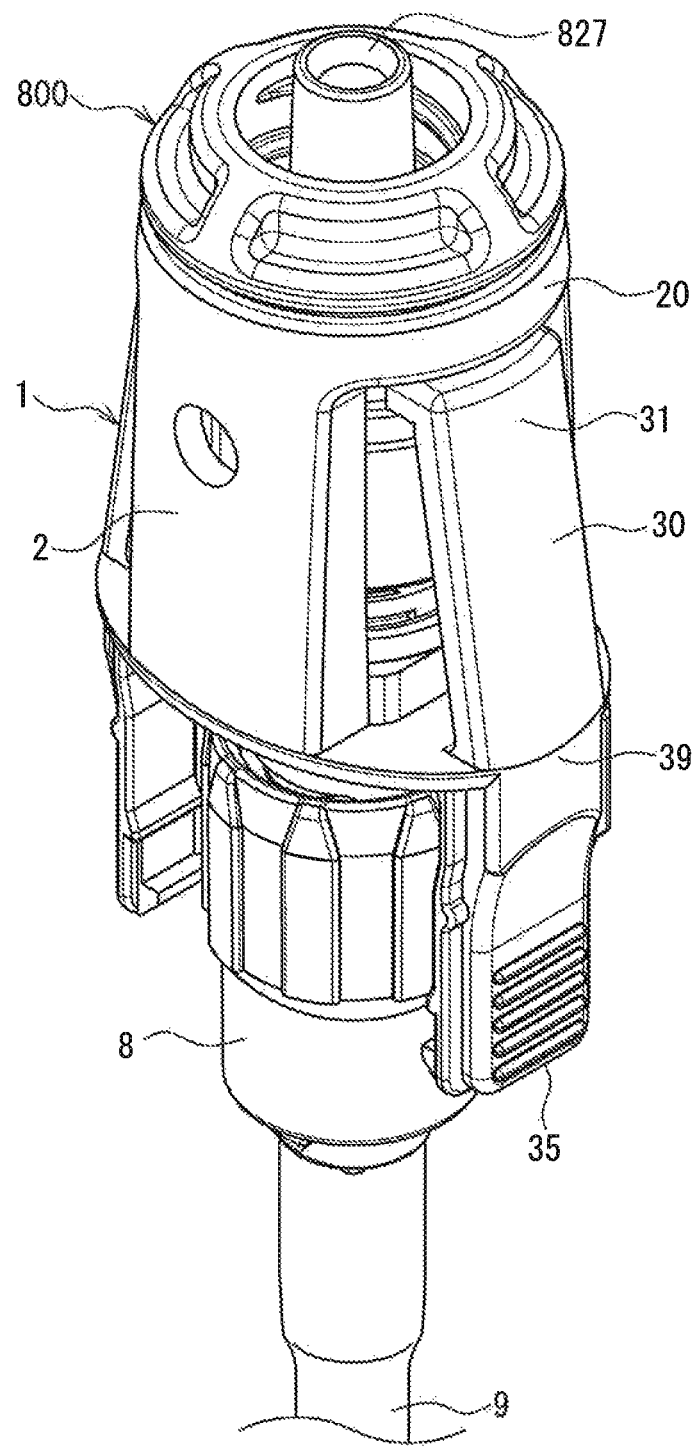
FIG. 11A is a perspective view showing a state in which the male connector and the female connector are connected to each other.

The claws 32 of the levers 30 slide sequentially on the peripheral wall 835 of the cap 830 and the annular projection 823. After the claws 32 have passed the annular projection 823, the base 15 of the connector main body 2 elastically recovers, and the claws 32 are engaged with the annular projection 823 (i.e., the locked state). Thus, the connection between the male connector 1 and the female connector 800 is completed. FIG. 11A is a perspective view showing this state. FIG. 11B is a cross-sectional view of the state.

Figure 11B:
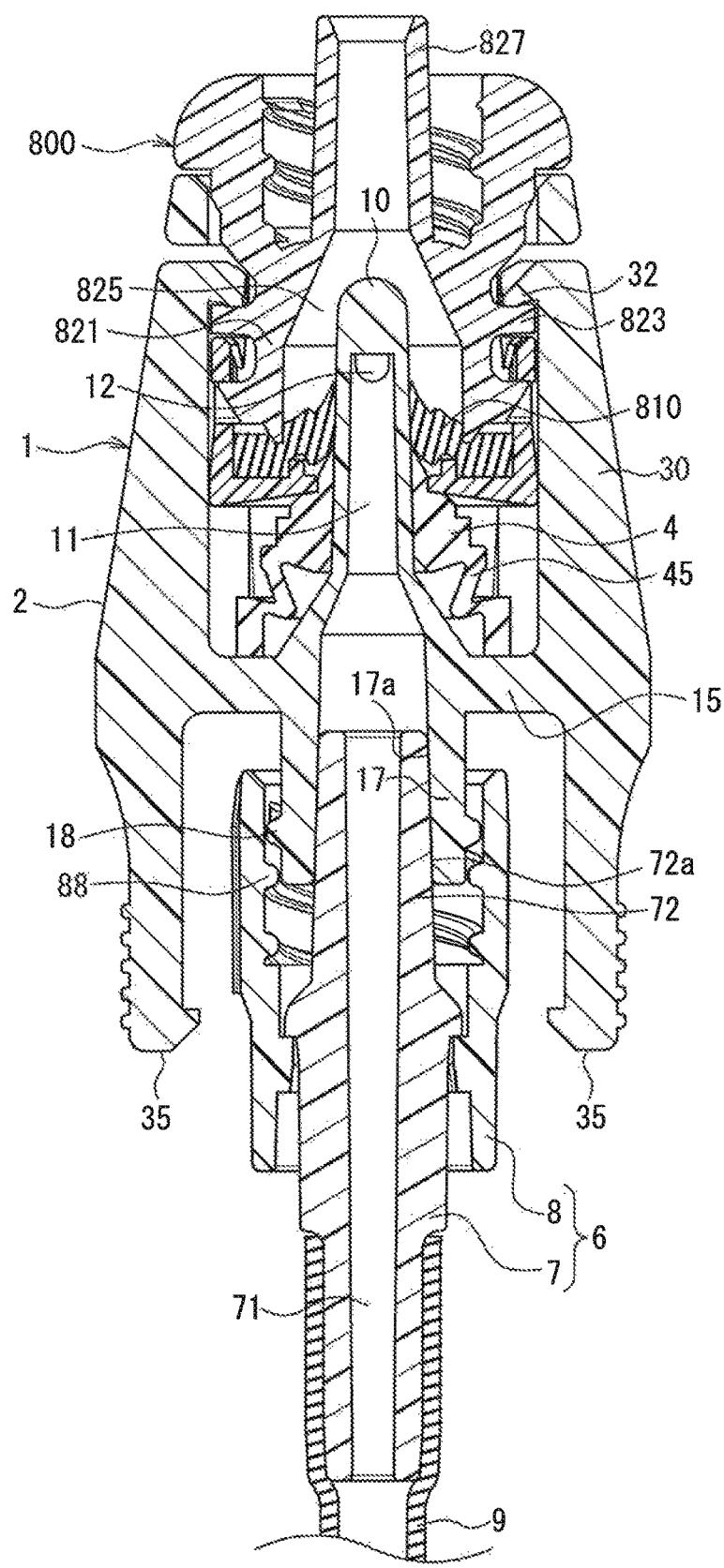
FIG. 11B is a cross-sectional view showing a state in which the male connector and the female connector are connected to each other.

As shown in FIG. 11B, the male luer 10 penetrates the slit 811 (see FIGS. 9A and 9B) of the septum 810, and thus the septum 810 is deformed toward the cavity 825 of the seat 821. The openings of the lateral holes 12 of the male luer 10 are exposed in the cavity 825 of the seat 821. Therefore, the flow channel 11 of the male luer 10 and the cavity 825 of the seat 821 are in communication with each other. In this state, a liquid is allowed to flow from the tube 9 to the flow channel 71 of the luer main body 7, the flow channel 11 of the male luer 10, the cavity 825 of the seat 821, and the male luer 827, or in the reverse direction.

The cover 4 receives the compressive force in the vertical direction. In particular, the outer circumferential wall 45 of the cover 4 is deformed so that its vertical dimension is reduced.

The male connector 1 and the female connector 800 can be disconnected from each other in the following manner. A force F (see FIG. 2F) is applied to a pair of operating portions 35 in the direction in which they come close to each other, so that the levers 30 are pivoted to release the engagement of the claws 32 with the annular projection 823. In this state, when the male connector 1 and the female connector 800 are pulled apart from each other, the male connector 1 and the female connector 800 can be disconnected from each other (see FIG. 10). The septum 810 elastically recovers immediately after the removal of the male luer 10, and thus the slit 811 is closed. The cover 4 expands and returns to the initial state due to its elastic recovery force, and the inner circumferential surface of the head portion 42 closes the openings of the lateral holes 12 of the male luer 10 (see FIGS. 4B, 4C, and 8B). The levers 30 elastically return to the initial state upon release of the external force applied to the operating portions 35.

The extracorporeal circuit for circulating blood includes a blood removal line and a reinfusion line. The blood removal line is used to remove blood from the vein of a patient, and the reinfusion line is used to return blood back to the vein of the patient. For example, in the extracorporeal circuit for hemodialysis, blood is transferred from a patient to a dialyzer via the blood removal line, and then blood is returned from the dialyzer to the patient via the reinfusion line. The blood removal line and the reinfusion line each have a coupling portion including the male connector 1 and the female connector 800, as described above. For example, in both the blood removal line and the reinfusion line, the opposite end of the tube 9 (see FIGS. 1 and 11A) to the male connector 1 may be connected to the vein of the patient. The male luer 827 (see FIG. 11A) of the female connector 800 may be connected to the dialyzer via a tube (not shown). A pump for circulating blood may be provided on the tube 9 that constitutes, e.g., the blood removal line.

As described above, when the male connector 1 and the female connector 800 are connected to each other (see FIGS. 11A and 11B), the flow channel 11 of the male luer 10 and the cavity 825 of the seat 821 are in communication with each other. Therefore, blood can flow through the male connector 1 and the female connector 800.

The claws 32 of the male connector 1 are engaged with the female connector 800 while the male connector 1 and the female connector 800 are being connected to each other. Therefore, even if an external force is applied, e.g., in the direction in which the male connector 1 and the female connector 800 are disconnected from each other during blood circulation, the male connector 1 and the female connector 800 will not be unintentionally disconnected from each other.

When the male connector 1 and the female connector 800 are disconnected from each other, the cover 4 of the male connector 1 immediately returns to the initial state and closes the lateral holes 12 of the male luer 10. Moreover, the septum 810 of the female connector 800 immediately returns to the initial state, so that the slit 811 is closed. Thus, even if the male connector 1 and the female connector 800 are unintentionally disconnected from each other during blood circulation, there is a low probability that blood will leak from the male connector 1 and the female connector 800.

As described above, a priming operation needs to be performed before circulating blood in the extracorporeal circuit. The priming operation introduces a priming fluid into the extracorporeal circuit and discharges air in the extracorporeal circuit to the outside. The priming operation is performed before connecting the male connector 1 to the female connector 800. As can easily be seen from FIG. 8B, when the male connector 1 is not connected to the female connector 800 (i.e., the initial state), the cover 4 closes the lateral holes 12 of the male luer 10 of the male connector 1. Therefore, in this state, the priming fluid cannot be introduced into the tube 9, the flow channel 71 of the luer main body 7, and the flow channel 11 of the male luer 10. If the male connector 1 and the screw lock connector 6 are disconnected from each other, the priming fluid can be introduced into the tube 9 and the flow channel 71 of the luer main body 7, but still cannot be introduced into the flow channel 11 of the male luer 10.

The adapter of the present invention is attached to the male connector 1 to facilitate the introduction of the priming fluid into the male connector 1. Hereinafter, the adapter of the present invention will be described.

Embodiment 1

1. Configuration of Adapter

Figure 12A:
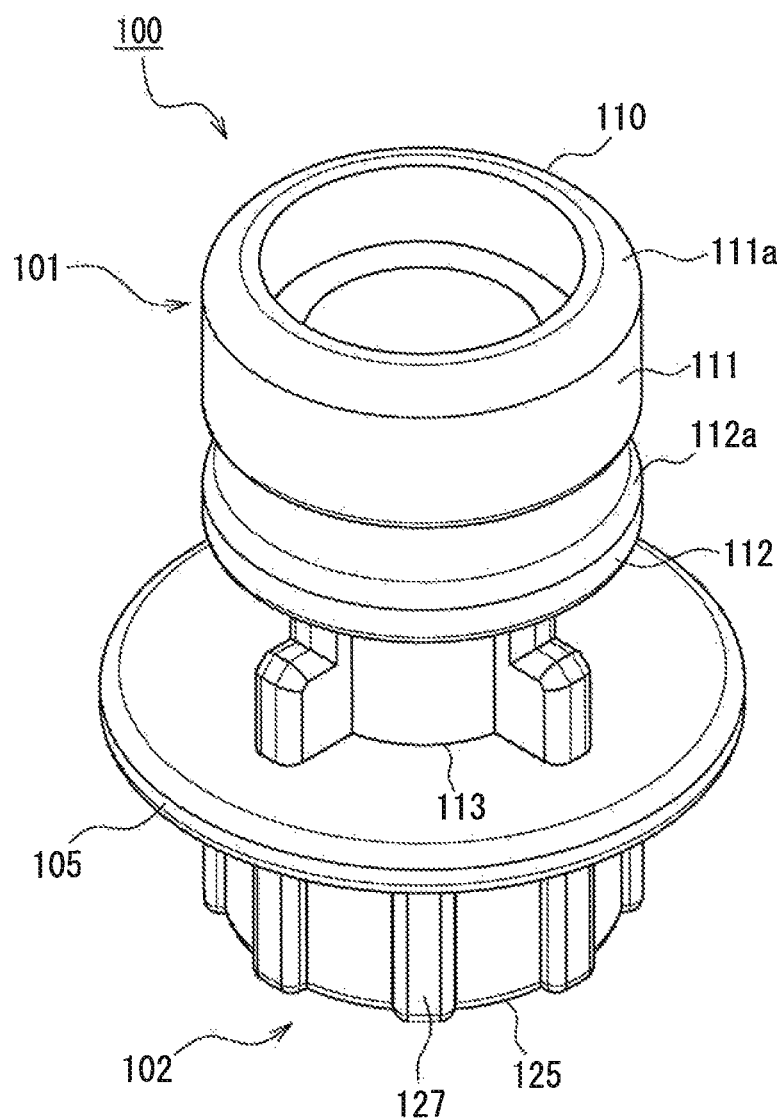
FIG. 12A is a perspective view of an adapter according to Embodiment 1 of the present invention when viewed from a first end portion of the adapter.
Figure 12B:
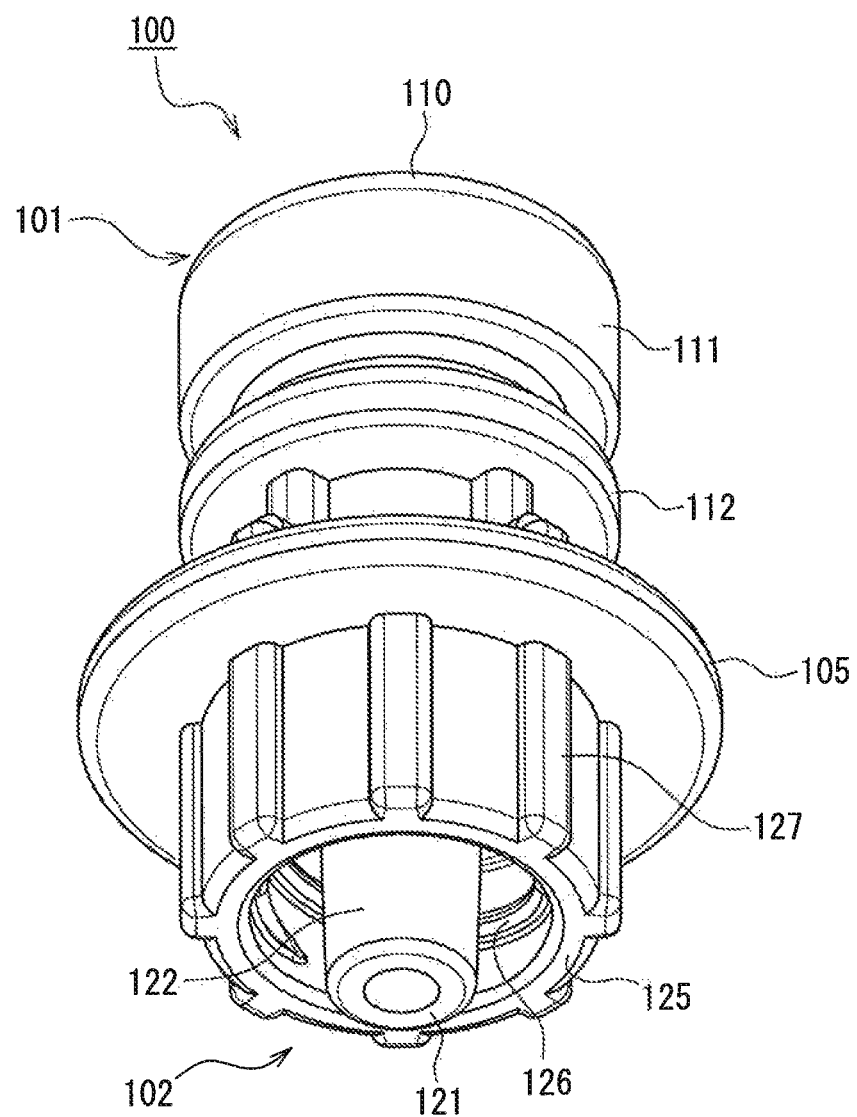
FIG. 12B is a perspective view of the adapter according to Embodiment 1 of the present invention when viewed from a second end portion of the adapter.
Figure 12C:
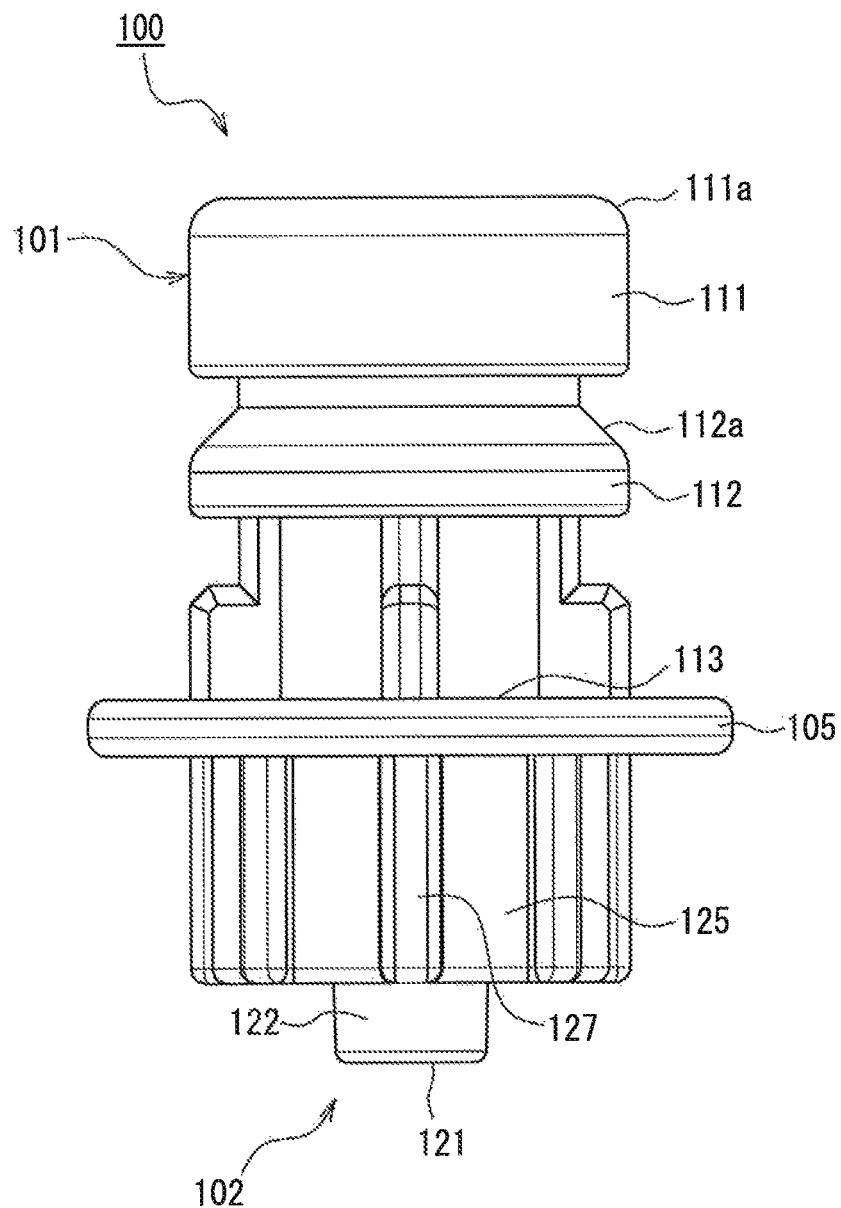
FIG. 12C is a side view of the adapter according to Embodiment 1 of the present invention.
Figure 12D:
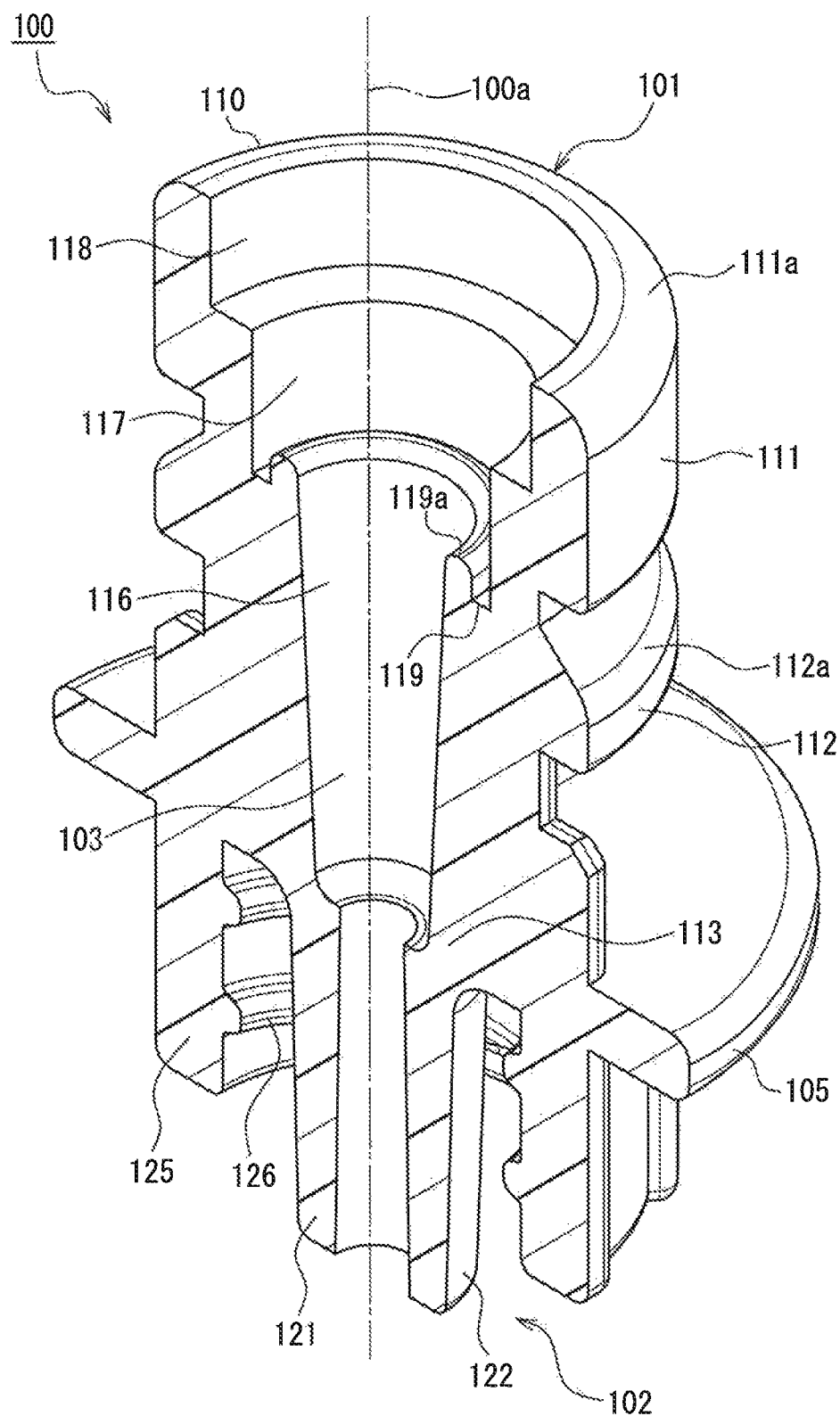
FIG. 12D is a cross-sectional perspective view of the adapter according to Embodiment 1 of the present invention.

FIG. 12A is a perspective view of an adapter 100 according to Embodiment 1 of the present invention when viewed from a first end portion 101 of the adapter 100. FIG. 12B is a perspective view of the adapter 100 when viewed from a second end portion 102 of the adapter 100. FIG. 12C is a side view of the adapter 100. FIG. 12D is a cross-sectional perspective view of the adapter 100. In FIG. 12D, an alternate long and short dash line 100a represents a central axis of the adapter 100 joining the first end portion 101 and the second end portion 102. For the sake of convenience of the following description, the direction that is orthogonal to the central axis 100a is referred to as a "radial direction" or a "diameter direction", and the direction of rotation about the central axis 100a is referred to as a "circumferential direction". With respect to the radial direction, the side nearer the central axis 100a is referred to as the "inner side", and the side further from the central axis 100a is referred to as the "outer side".

As shown in FIG. 12D, the adapter 100 has a through hole (flow channel) 103 that penetrates the adapter 100 along the central axis 100a. The through hole 103 is open in both the first end portion 101 and the second end portion 102 of the adapter 100, and allows the first end portion 101 to be in communication with the second end portion 102. As will be described later, when the priming operation is performed on the male connector 1 with the adapter 100 attached to the male connector 1, a priming fluid flows through the through hole 103.

The first end portion 101 includes a hollow tubular portion 110 that is coaxial with the central axis 100a. The through hole 103 penetrates the tubular portion 110. A first projection 111 and a second projection 112 are provided on the outer circumferential surface of the tubular portion 110. A large diameter portion 105 is provided on a base end 113 of the tubular portion 110.

Both the first projection 111 and the second projection 112 are annular projections that continuously extend in the circumferential direction. The first projection 111 is located on the leading end side of the tubular portion 110. The second projection 112 is located on the base end 113 side (i.e., on the side facing the large diameter portion 105) of the tubular portion 110 with respect to the first projection 111. The first projection 111 is spaced apart from the second projection 112, and an annular groove (recessed portion) continuously extending in the circumferential direction is formed between the first projection 111 and the second projection 112. Moreover, the second projection 112 is spaced apart from the large diameter portion 105, and an annular groove (recessed portion) continuously extending in the circumferential direction is formed between the second projection 112 and the large diameter portion 105. The outer circumferential surface of the first projection 111 and the outer circumferential surface of the second projection 112 constitute cylindrical surfaces that are coaxial with the central axis 100a and have the same radius. The external diameter of the first projection 111 and the external diameter of the second projection 112 are approximately equal to the external diameter of the female connector 800 (i.e., the external diameter of the peripheral wall 835 of the cap 830 and the external diameter of the annular projection 823, see FIG. 9A) that is connected to the male connector 1 to which the adapter 100 is to be attached.

The outer circumferential surface of the first projection 111 and the outer circumferential surface of the second projection 112 do not have to be cylindrical surfaces. For example, the cross-sectional shape of each of the first projection 111 and the second projection 112 in the cross section containing the central axis 100a may be in the form of a triangle, arc, or the like. In this case, however, the first projection 111 and the second projection 112 are preferably annular projections that continuously extend in the circumferential direction. Thus, the claws 32 can be engaged with the first projection 111 and the second projection 112 regardless of the position of the adapter 100 in the direction of rotation relative to the male connector 1, as will be described later.

The second projection 112 has a tapered surface 112a on the end edge thereof facing the first projection 111. The tapered surface 112a is a conical surface whose external diameter gradually decreases toward the first projection 111.

The large diameter portion 105 protrudes outward in the radial direction compared to the first projection 111 and the second projection 112. The external diameter of the large diameter portion 105 is preferably equal to or slightly larger than the external diameter of the hood 20 of the male connector 1 at the leading end 20a (see FIG. 2A). In this embodiment, the large diameter portion 105 has a substantially disk shape (so-called flange shape), but the present invention is not limited thereto. For example, a substantially elliptical shape may be divided in the circumferential direction by one or more notches formed along the radial direction. In this embodiment, the large diameter portion 105 is circular when viewed along the central axis 100a. The shape of the large diameter portion 105 may be other than this, e.g., an approximate ellipse, a triangle, a rectangle, or a hexagon. Moreover, the large diameter portion 105 may be in the form of one or more projections (e.g., plate-shaped projections, rod-shaped projections, or dome-shaped projections) that protrude from the base end 113 in the radial direction.

As shown in FIG. 12D, the inner circumferential surface of the tubular portion 110 defines the through hole 103 and includes a first region 116, a second region 117, and a third region 118 that are arranged in the direction from the base end 113 to the leading end of the tubular portion 110. The first region 116, the second region 117, and the third region 118 are coaxial with the central axis 100a, and the internal diameter increases in the indicated order. The internal diameter of the second region 117 is larger than the external diameter of the head portion 41 (see FIG. 3A) of the cover 4. The internal diameter of the first region 116 is smaller than the external diameter of the heat portion 41 of the cover 4.

In this embodiment, the inner circumferential surface of the first region 116 is a tapered surface (conical surface) whose internal diameter gradually decreases toward the base end 113. The inner circumferential surfaces of the second region 117 and the third region 118 are cylindrical surfaces. However, the present invention is not limited thereto. For example, the inner circumferential surface of the first region 116 may be a cylindrical surface, and one or both of the second region 117 and the third region 118 may have an inner circumferential surface that is a tapered surface (conical surface) whose internal diameter gradually decreases toward the base end 113. The inner circumferential surface of the tubular portion 110 may include another region with an internal diameter that is different from those of the first region 116, the second region 117, and the third region 118. Alternatively, one or both of the second region 117 and the third region 118 may be omitted.

A shoulder portion 119 is formed between the first region 116 and the second region 117. The shoulder portion 119 is based on the difference in the internal diameter between the first region 116 and the second region 117. The shoulder portion 119 is a plane perpendicular to the central axis 100a. An annular rib 119a continuously extends in the circumferential direction and protrudes from the shoulder portion 119 toward the leading end of the tubular portion 110. The annular rib 119a is a cylindrical projection that is formed along the inner circumferential end edge of the shoulder portion 119 and is coaxial with the central axis 100a. The annular rib 119a is spaced apart from the inner circumferential surface of the second region 117 in the radial direction. The internal diameter of the annular rib 119a is larger than the external diameter of the male luer 10, smaller than the external diameter of the head portion 41 (see FIG. 3A) of the cover 4, and approximately equal to or slightly larger than the external diameter of the protrusion 44 that protrudes from the head portion 41.

The second end portion 102 of the adapter 100 includes a male luer 121 having a tubular shape and an outer cylinder 125 that surrounds the male luer 121. An outer circumferential surface 122 of the male luer 121 is a tapered surface (so-called male tapered surface) whose external diameter gradually decreases toward the leading end. The through hole 103 penetrates the male luer 121. A female thread (screw structure) 126 is formed on the inner circumferential surface of the outer cylinder 125 that faces the male luer 121. A plurality of ribs 127 extending parallel to the central axis 100a are provided on the outer circumferential surface of the outer cylinder 125. The male luer 121 and the female thread 125 may comply with a lock connector defined by ISO594-2.

It is preferable that the adapter 1002 is made of a hard material. Specifically, a resin material such as polyacetal, polycarbonate, polystyrene, polyamide, polypropylene, or rigid polyvinyl chloride may be used. The adapter 100 can be integrally produced as a single component through injection molding or the like using such a resin material.

In this embodiment, the outer cylinder 125 is provided on the surface of the large diameter portion 105 that is on the same side as the second end portion 102. However, the outer cylinder 125 may be spaced apart from the large diameter portion 105 in the direction of the central axis 100a. In this case, the male luer 121 is also spaced apart from the base end 113 of the tubular portion 110 in the direction of the central axis 100a. The base end 113 of the tubular portion 110 and the male luer 121 are coupled with a hollow member in which the through hole 103 is provided.

2. Method for Using Adapter 2.1 Connection of Adapter to Male Connector at First Position The adapter 100 is connected to the male connector 1 before performing the priming operation on the male connector 100. This will be described below.

Figure 13:
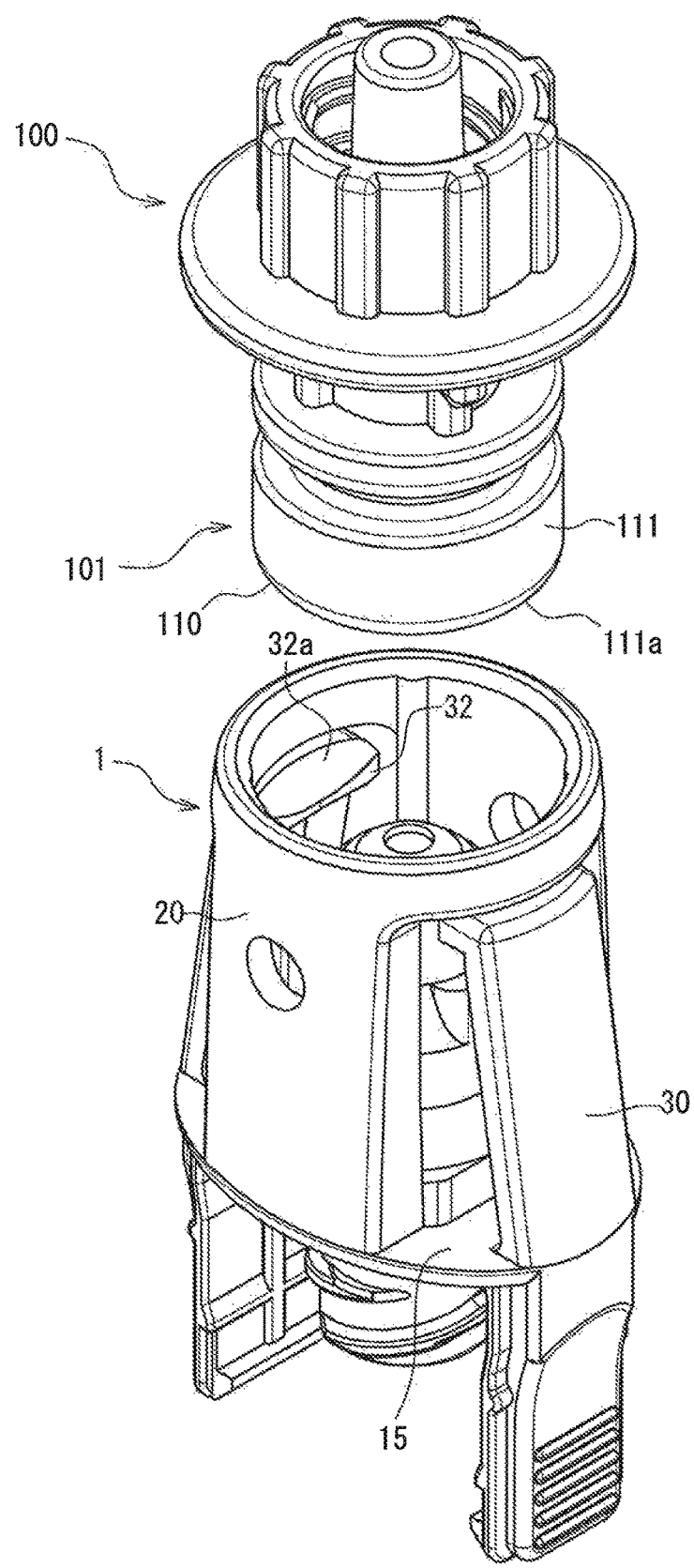
FIG. 13 is a perspective view of the adapter according to Embodiment 1 of the present invention immediately before it is connected to the male connector.

First, as shown in FIG. 13, the first end portion 101 (the tubular portion 110) of the adapter 100 is located opposite to the male connector 1. The screw lock connector 6 and the tube 9 have not been connected to the male connector 1 at this stage.

From the state shown in FIG. 13, the first end portion 101 is connected to the male connector 1. Specifically, the tubular portion 110 of the adapter 100 is inserted into the hood 20 of the male connector 1, and is pushed inward. An end edge 111a (see FIG. 12A) at the leading end of the first projection 111 of the adapter 100 abuts against the inclined surfaces 32a (see FIGS. 2E, 2F, 4A, and 4B) of the claws 32 of the levers 30. When the adapter 100 is pushed further into the hood 20, the end edge 111a elastically displaces (swings) the levers 30 so that the claws 32 move away from the male luer 10. Subsequently, when the adapter 100 is pushed further into the hood 20, the claws 32 slide on the first projection 111 of the adapter 100. After the claws 32 have passed the first projection 111, the base 15 of the connector main body 2 elastically recovers, and the claws 32 are fitted in the annular groove that is formed between the first projection 111 and the second projection 112 of the adapter 100 and continuously extends in the circumferential direction.

Figure 14A:
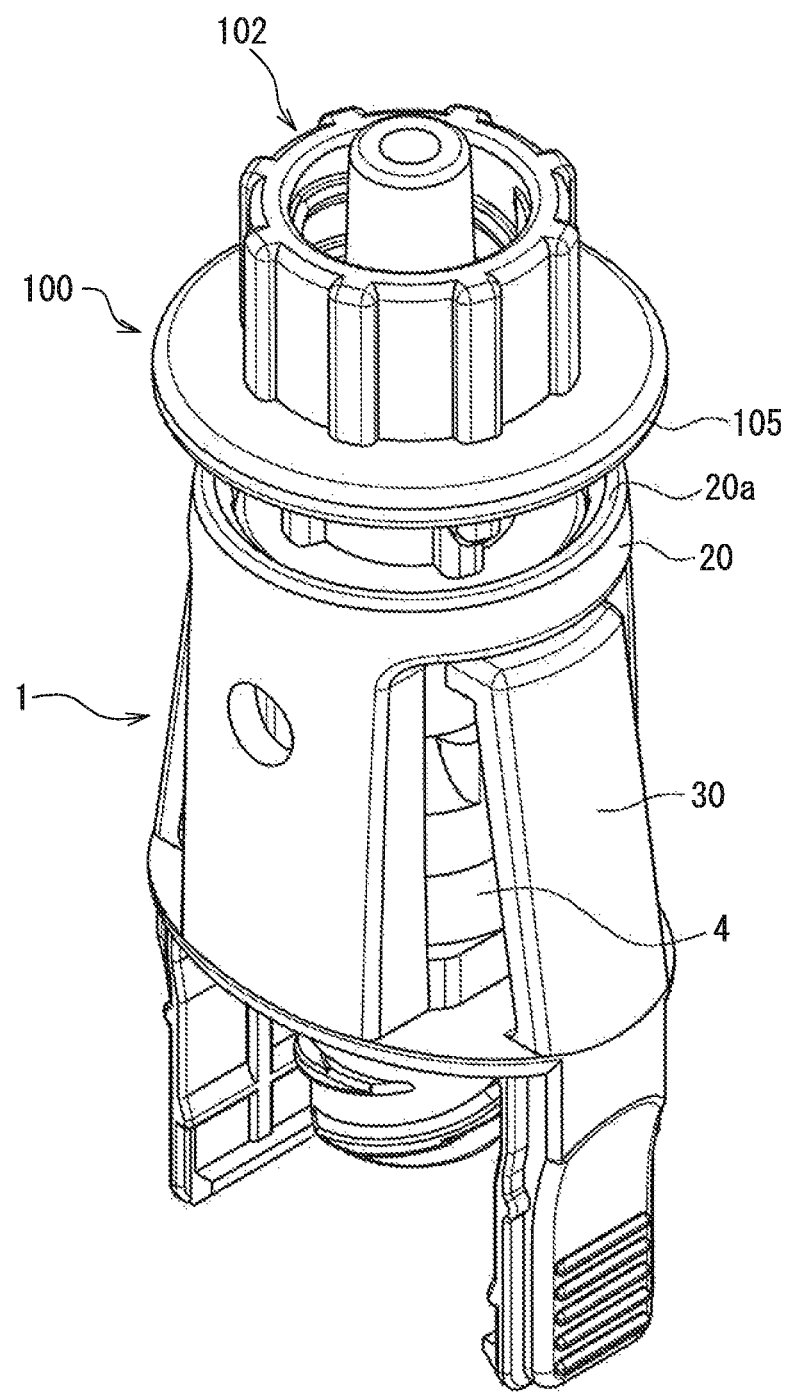
FIG. 14A is a perspective view of the adapter according to Embodiment 1 of the present invention when it is attached to the male connector at the first position.
Figure 14B:
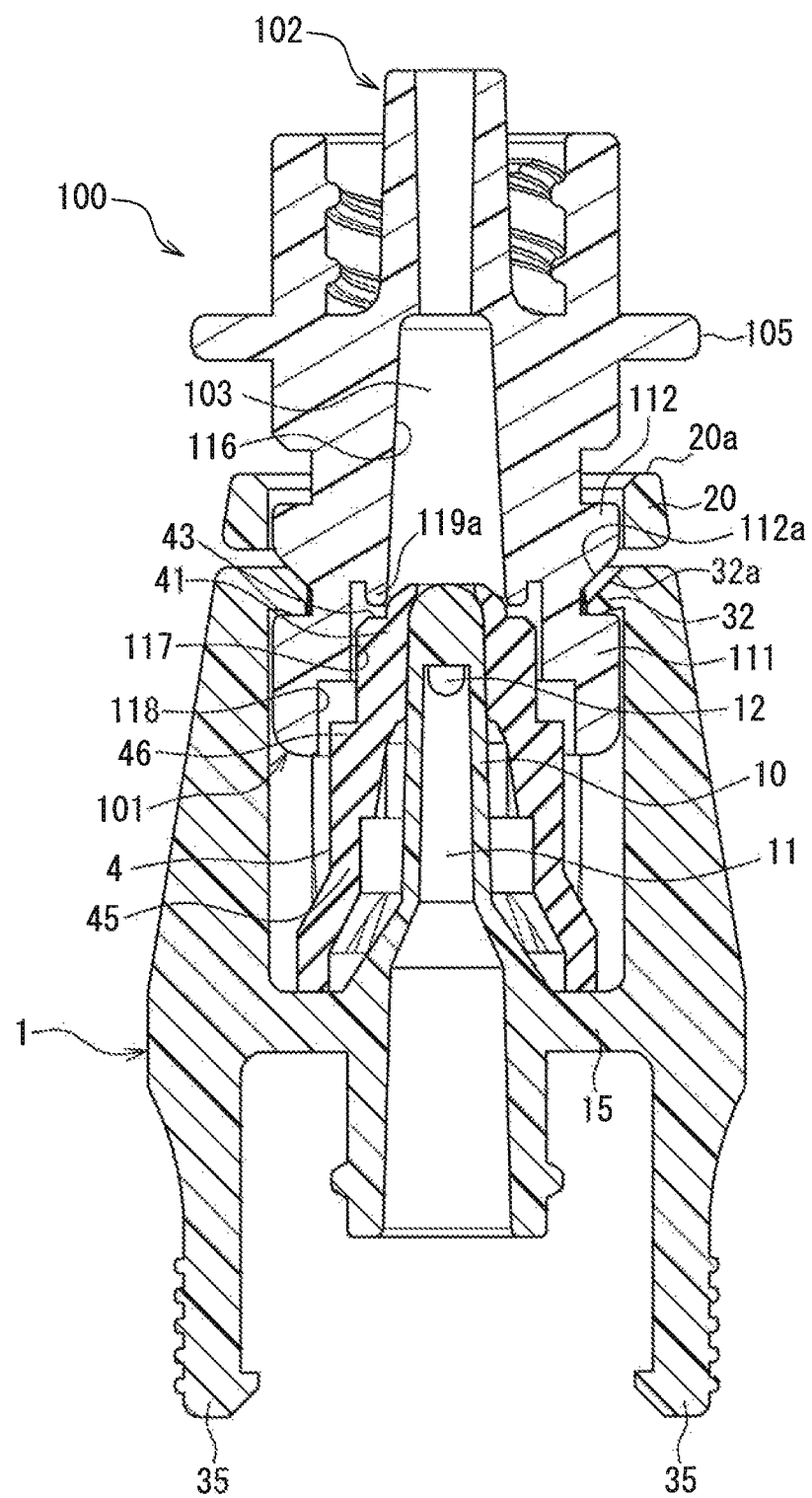
FIG. 14B is a cross-sectional view of the adapter and the male connector shown in FIG. 14A
Figure 14C:
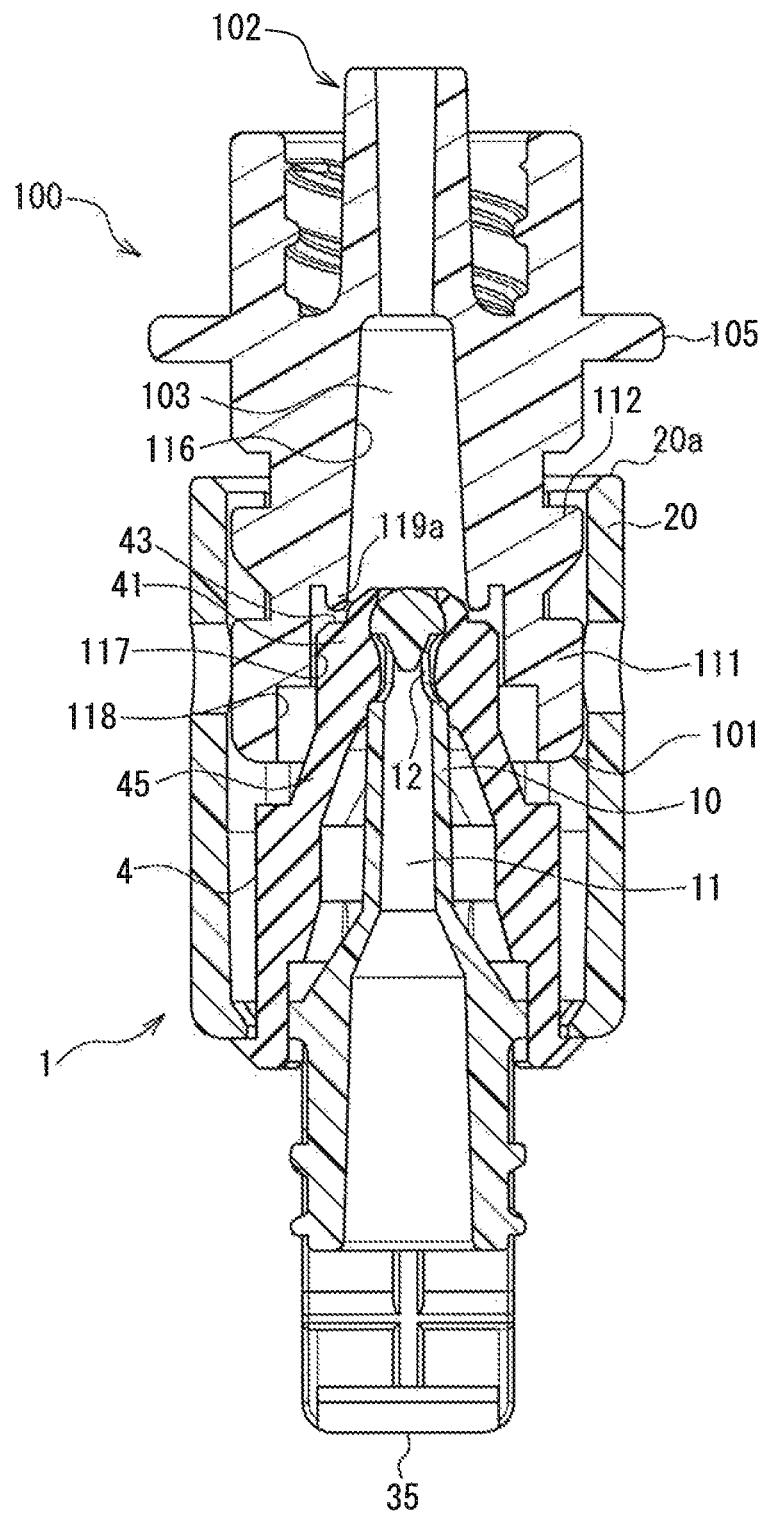
FIG. 14C is another cross-sectional view of the adapter and the male connector shown in FIG. 14A

FIG. 14A is a perspective view showing this state. FIGS. 14B and 14C are cross-sectional views of the state. The cross section in FIG. 14B is the same as that in FIG. 4B. The cross section in FIG. 14C is the same as that in FIG. 4C.

As shown in FIG. 14B, the claws 32 of the male connector 1 are engaged with the first projection 111 of the adapter 100. Therefore, the male connector 1 and the adapter 100 cannot be disconnected from each other only by pulling them in opposite directions. However, when a force F (see FIG. 2F) is applied to a pair of operating portions 35 in the direction in which they come close to each other, the engagement of the claws 32 with the first projection 111 is released, and the adapter 100 can be disconnected from the male connector 1. In the present invention, the position of the adapter 100 relative to the male connector 1 in which the adapter 100 is connected to the male connector 1 with the claws 32 being engaged with the first projection 111 is referred to as a "first position".

As shown in FIGS. 14B and 14C, the head portion 41 of the cover 4 is inserted into the second region 117 of the adapter 100. The annular upper surface 43 of the head portion 41 is spaced apart from the annular rib 119a in the vertical direction and faces the annular rib 119a. As is best shown in FIG. 14B, the rib-shaped projections 46 that protrude from the outer circumferential surface of the outer circumferential wall 45 of the cover 4 are housed in the third region 118 of the adapter 100. The cover 4 is spaced apart from or merely in contact with the adapter 100. Therefore, the adapter 100 exerts substantially no force on the cover 4. The shape of the cover 4 is substantially the same as that in the initial state (see FIGS. 4A to 4C). The openings of the lateral holes 12 of the male luer 10 are closed off by the inner circumferential surface of the through hole 42 of the cover 4. The flow channel 11 of the male luer 10 is sealed with the head portion 41 of the cover 4. Thus, the flow channel 11 of the male luer 10 is not in communication with the through hole 103 of the adapter 100.

The large diameter portion 105 is spaced apart from the leading end 20a of the hood 20 in the vertical direction.

The male connector 1 and the adapter 100 are sterilized and packaged in a state in which the adapter 100 is connected to the male connector 1 at the first position (see FIGS. 14A to 14C). The sterilization and packaging processes may be carried out by manufacturers and distributors of the male connector 1. The male connector 1 provided with the adapter 100, which have been sterilized and packaged, are delivered and stored in medical institutions such as hospitals. The sterilization and packaging processes are not particularly limited, and may be the same as those generally performed on the conventional male connector.

When the adapter 100 is in the first position, the cover 4 is not substantially deformed and remains its initial shape. Therefore, even if the male connector 1 to which the adapter 100 is connected at the first position is stored for a long period of time, the elastic recovery force of the outer circumferential wall 45 of the cover 4 will not be reduced.

When the adapter 100 is in the first position, the claws 32 are engaged with the first projection 111. Therefore, even if the male connector 1 is subjected to vibration, an external force, or the like during transport, there is a low probability that the male connector 1 and the adapter 100 will be disconnected from each other.

2.2 Preparation for Priming

When an extracorporeal circuit is formed in medical institutions, the package containing the male connector 1 and the adapter 100 is torn open, and the male connector 1 (see FIGS. 14A to 14C) to which the adapter 100 is connected at the first position is taken out.

Figure 15:
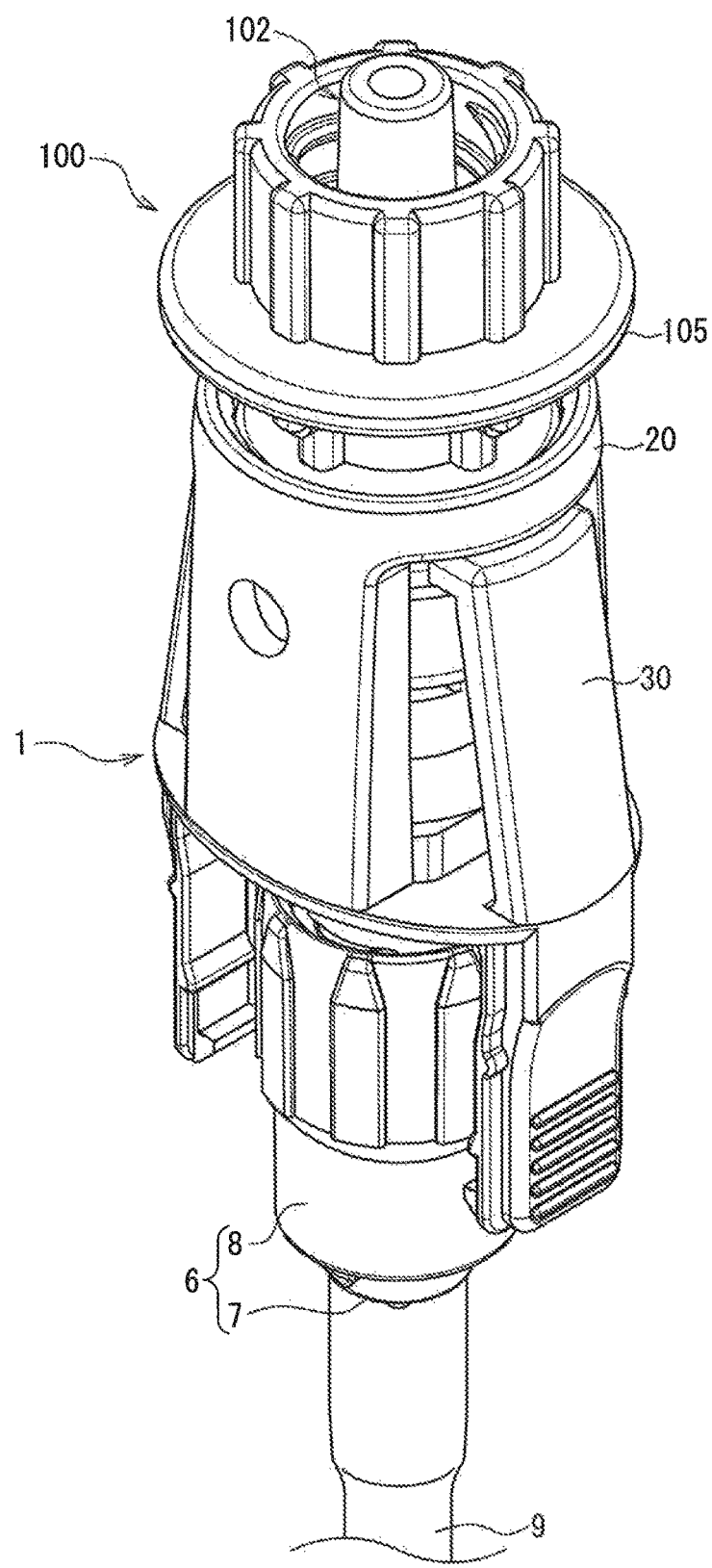
FIG. 15 is a perspective view showing a state in which a tube constituting an extracorporeal circuit is connected to the male connector to which the adapter according to Embodiment 1 of the present invention is connected at the first position.

The screw lock connector 6 (see FIGS. 7A and 7B) is attached to the distal end of the soft tube 9 that constitutes each of the blood removal line and the reinfusion line in the extracorporeal circuit. As shown in FIG. 15, the male connector 1 is connected to the screw lock connector 6. The adapter 100 is still in the first position relative to the male connector 1.

Next, the adapter 100 is pushed toward the male connector 1. As shown in FIG. 14B, when the adapter 100 is in the first position, the tapered surface 112a (see FIG. 12A) provided on the second projection 112 of the adapter 100 faces the inclined surfaces 32a (see FIGS. 2E, 2F, 4A, and 4B) of the claws 32 of the levers 30. When the adapter 100 is pushed into the hood 20, the tapered surface 112a elastically displaces (swings) the levers 30 so that the claws 32 move away from the male luer 10. Subsequently, when the adapter 100 is pushed further into the hood 20, the claws 32 slide on the second projection 112 of the adapter 100. After the claws 32 have passed the second projection 112, the base 15 of the connector main body 2 elastically recovers, and the claws 32 are fitted in the annular groove that is formed between the second projection 112 and the large diameter portion 105 of the adapter 100 and continuously extends in the circumferential direction.

Figure 16A:
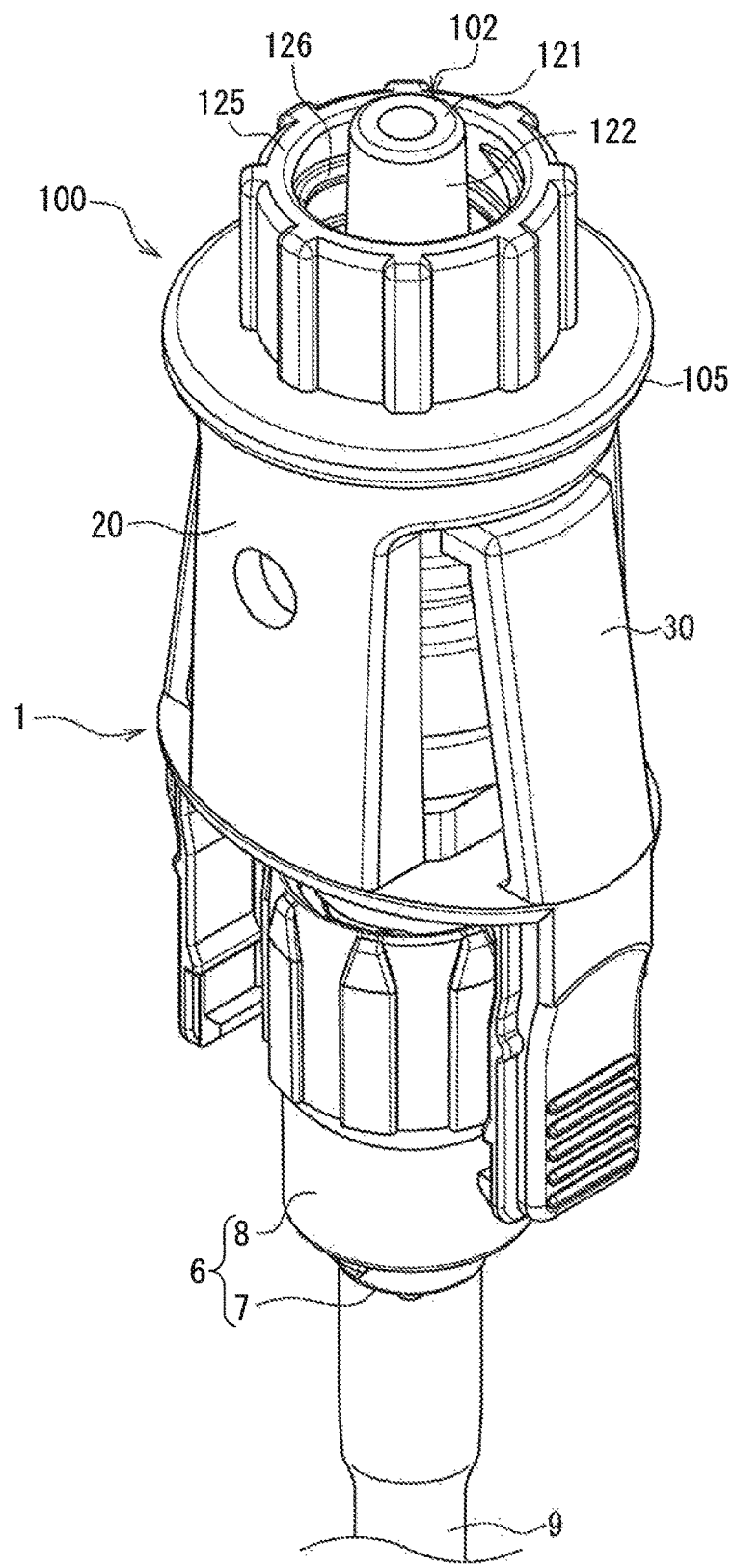
FIG. 16A is a perspective view showing a state in which the adapter according to Embodiment 1 of the present invention is attached to the male connector at the second position while the tube constituting an extracorporeal circuit is being connected to the male connector.
Figure 16B:
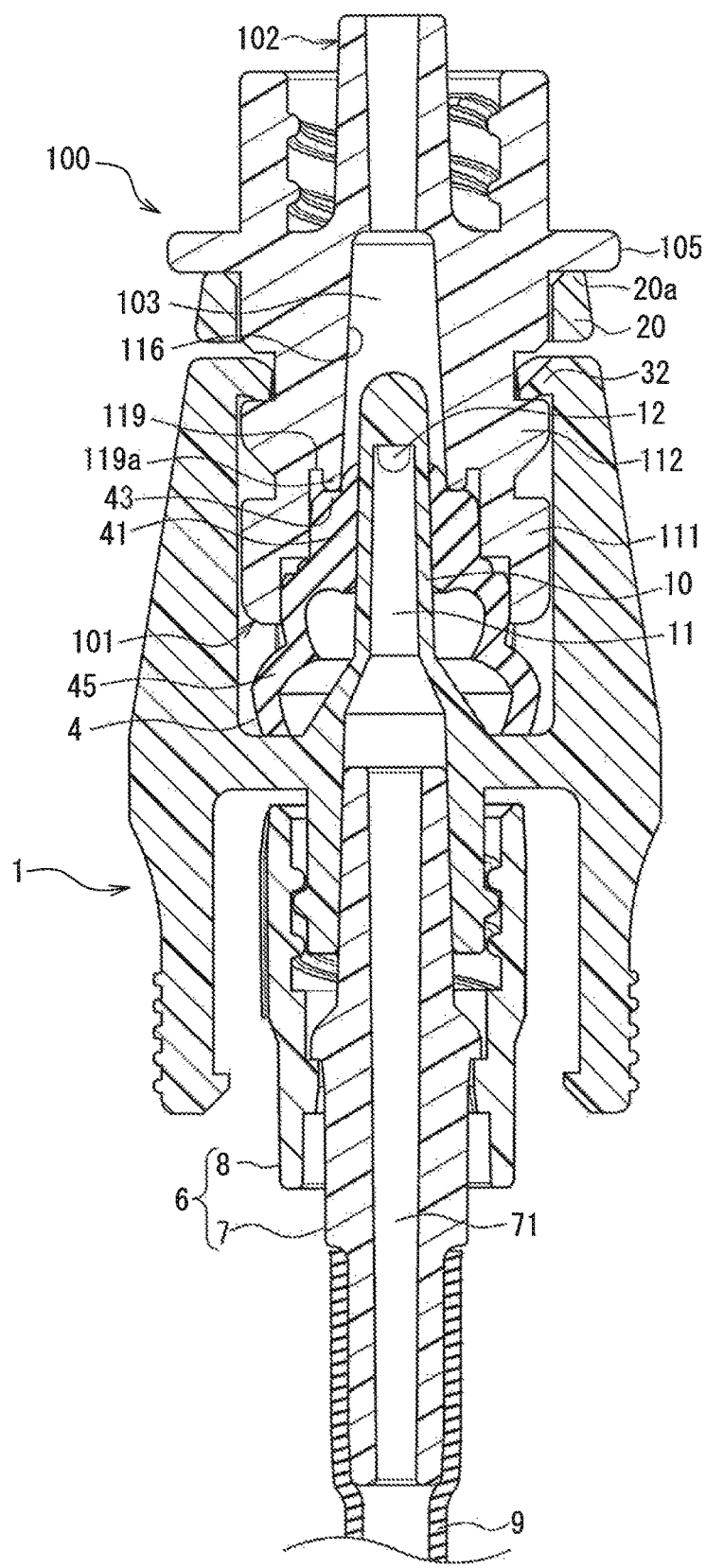
FIG. 16B is a cross-sectional view of the adapter and the male connector shown in FIG. 16A
Figure 16C:
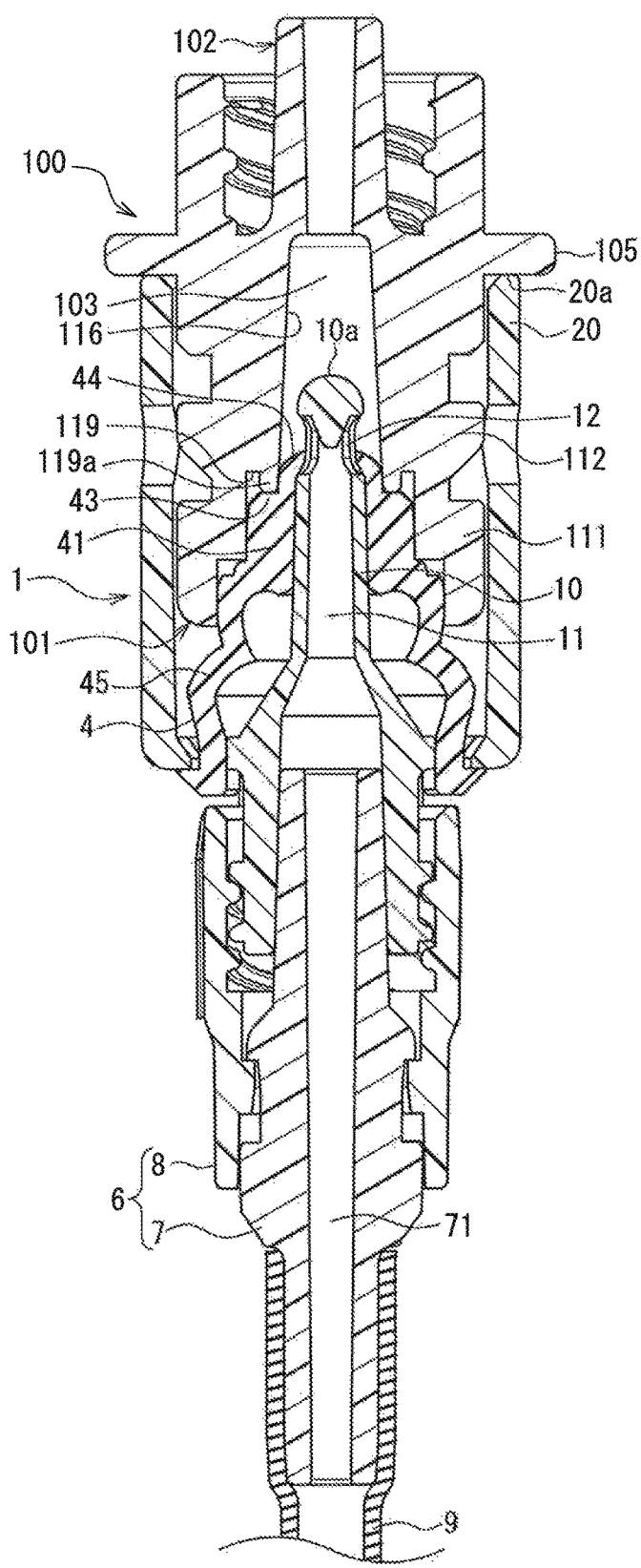
FIG. 16C is another cross-sectional view of the adapter and the male connector shown in FIG. 16A

FIG. 16A is a perspective view showing this state. FIGS. 16B and 16C are cross-sectional views of the state. The cross section in FIG. 16B is the same as that in FIGS. 4B and 14B. The cross section in FIG. 16C is the same as that in FIGS. 4C and 14C.

As shown in FIG. 16B, the claws 32 of the male connector 1 are engaged with the second projection 112 of the adapter 100. Therefore, similarly to the state in which the adapter 100 is in the first position, the male connector 1 and the adapter 100 cannot be disconnected from each other only by pulling them in opposite directions. In the present invention, the position of the adapter 100 relative to the male connector 1 in which the adapter 100 is connected to the male connector 1 with the claws 32 being engaged with the second projection 112 is referred to as a "second position".

As described above, the tapered surface 112a is formed on the end edge of the second projection 112 that faces the first projection 111. Therefore, an operator is required to simply push the adapter 100 into the male connector 1, so that the state of engagement of the claws 32 with the first projection 111 (see FIGS. 14A to 14C) can easily be shifted to the state of engagement of the claws 32 with the second projection 112 (see FIGS. 16A to 16C).

As shown in FIG. 16C, the protrusion 44 of the head portion 41 of the cover 4 is fitted in the first region 116 of the adapter 100. The annular rib 119a that protrudes from the shoulder portion 119 of the adapter 100 abuts against the upper surface 43 of the head portion 41. The annular rib 119a presses the upper surface 43 downward. Consequently, the outer circumferential wall 45 of the cover 40 is elastically and compressively deformed in the vertical direction.

The male luer 1 penetrates the head portion 41 and is inserted into the first region 116 while the head portion 41 of the cover 4 is abutting against the annular rib 119a. The leading end 10a of the male luer 10 protrudes over the head portion 41, and the lateral holes 12 of the male luer 10 are exposed in the first region 116. Thus, the flow channel 11 of the male luer 10 is in communication with the through hole 103 of the adapter 100.

The annular rib 119a of the adapter 100 and the upper surface 43 of the head portion 41 of the cover 4 are pressed against each other in the vertical direction to form a liquid-tight seal between them. The contact area between the leading end of the annular rib 119a and the upper surface 43 of the head portion 41 is very small, so that the sealing between them can be improved.

As shown in FIGS. 16B and 16C, the first projection 111 and the second projection 112 of the adapter 100 are inserted into the hood 20 of the male connector 1. The large diameter portion 105 protrudes outside the hood 20 in the radial direction, and abuts against the leading end 20a of the hood 20 in the vertical direction. Therefore, the large diameter portion 105 prevents the adapter 100 from being further inserted into the hood 20 to a depth deeper than the second position. This is advantageous in preventing damage to the cover 4 due to excessive deformation caused by the adapter 100.

2.3 Priming

Since the adapter 100 has been moved to the second position (see FIGS. 16A to 16C), the lateral holes 12 of the male luer 10 are open. Therefore, a priming fluid can be introduced into the male connector 1. The method for introducing the priming fluid may be selected as desired.

The priming operation in Embodiment 1 preferably uses a drain connector 150 shown in FIGS. 17A and 17B. FIG. 17A is a perspective view of the drain connector 150. FIG. 17B is a cross-sectional view of the drain connector 150.

The drain connector 150 includes a tubular portion 151 having a hollow cylindrical shape. As shown in FIG. 17A, an arm 155 and a handle 157 protrude from the outer circumferential surface of the tubular portion 151. The arm 155 has a cantilever structure with one end (fixed end) being fixed to the tubular portion 151. The arm 155 is bent in a substantially "L" shape so that the arm 155 and the tubular portion 151 can form a substantially triangle. The other end (free end) 155a of the arm 155 is close to the tubular portion 151. The handle 157 has a substantially "U" shape, and both ends are fixed to the tubular portion 151. Male threads 153a, 153b are provided on both ends of the tubular portion 151, respectively.

As shown in FIG. 17B, the tubular portion 151 has a through hole (flow channel) 152 that connects one end to the other. Portions of the inner circumferential surface of the through hole 152 that are near both ends of the tubular portion 151 constitute tapered surfaces (so-called female tapered surfaces) 154a, 154b whose internal diameters gradually increase toward the respective ends of the tubular portion 151.

The first male thread 153a and the first female tapered surface 154a that are provided on one end of the tubular portion 151 and the second male thread 153b and the second female tapered surface 154b that are provided on the other end of the tubular portion 151 are both fitted to the female thread 126 and the outer circumferential surface (male tapered surface) 122 of the male luer 121 of the adapter 100. For example, the male threads 153a, 153b and the female tapered surfaces 154a, 154b may comply with a lock connector defined by ISO594-2.

Hereinafter, two typical priming methods using the drain connector 150 will be described.

[First Priming Method]

Figure 18A:
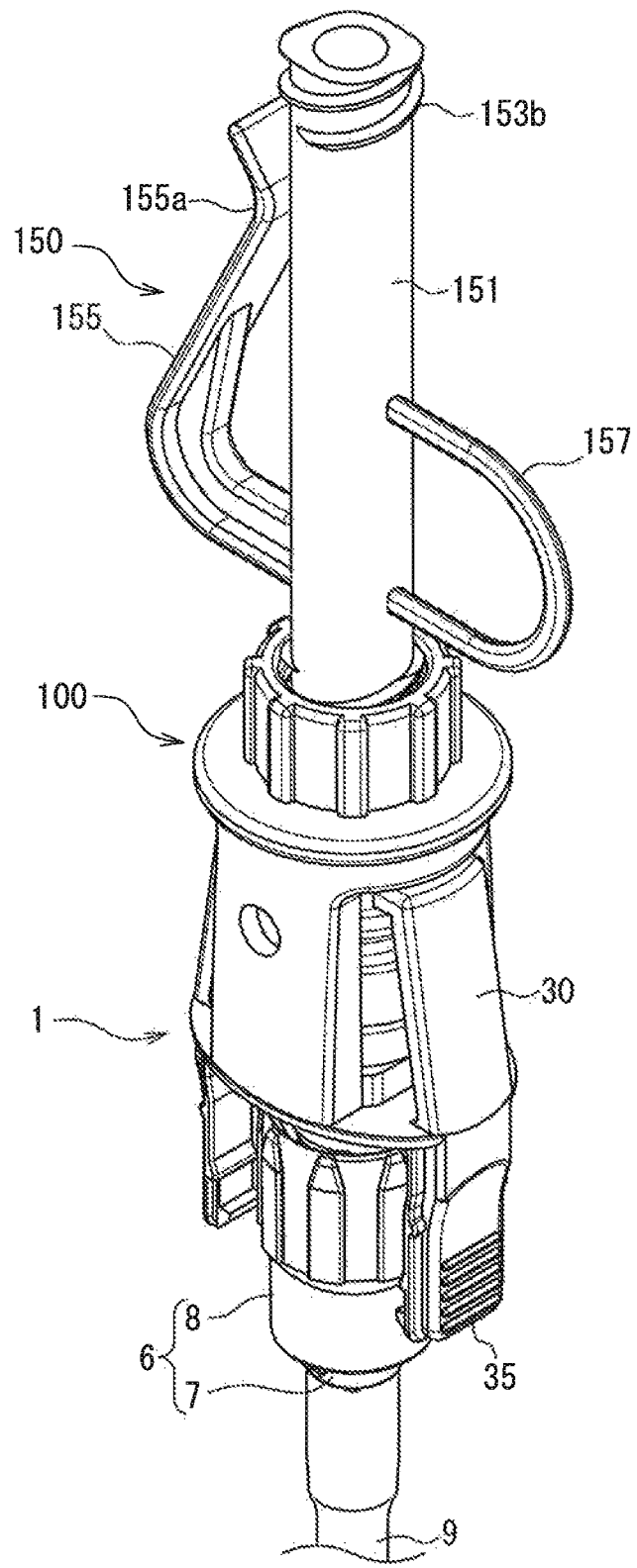
FIG. 18A is a perspective view for explaining a first priming method for the male connector using the adapter according to Embodiment 1 of the present invention.
Figure 18B:
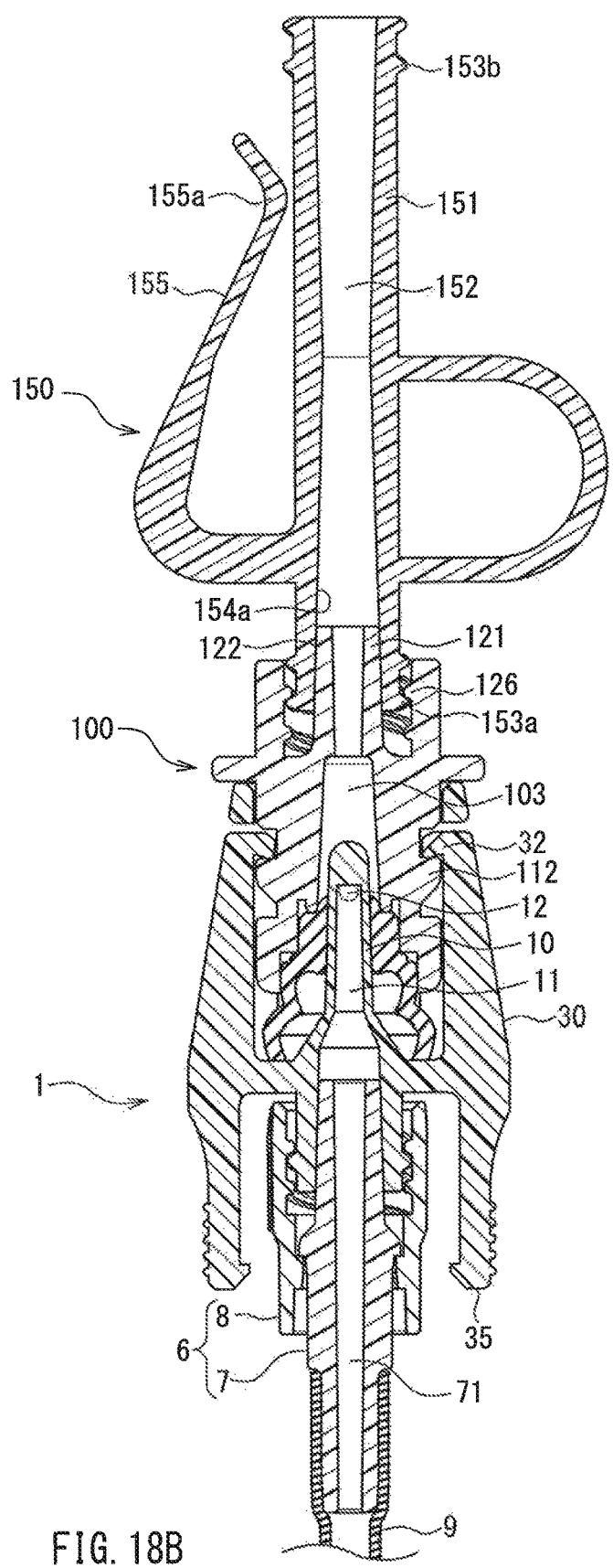
FIG. 18B is a cross-sectional view of FIG. 18A

FIGS. 18A and 18B are a perspective view and a cross-sectional view for explaining a first priming method, respectively. As shown in FIGS. 18A and 18B, the drain connector 150 (see FIGS. 17A and 17B) is attached to the adapter 100 (see FIGS. 16A to 16C) that is connected to the male connector 1 at the second position. Specifically, the male luer 121 of the adapter 100 is inserted into the through hole 152 of the drain connector 150, and the male thread 153a of the drain connector 150 is screwed into the female thread 126 of the adapter 100. The female tapered surface 154a of the drain connector 150 and the male tapered surface of the outer circumferential surface 122 of the male luer 121 have the same diameter and taper angle. Therefore, the male luer 121 and the tubular portion 151 of the drain connector 150 are connected to each other in a liquid-tight manner.

The drain connector 150 is fixed to a container for collecting a priming fluid with the end of the drain connector 150 that is not connected to the adapter 100 (i.e., the end on which the male thread 153b is formed) facing downward. For example, the container has an opening that is open upward, and the upper end of the wall of the container surrounding the opening may be sandwiched between the free end 155a of the arm 155 and the tubular portion 151, so that the drain connector 150 can be attached to the wall of the container. In this state, a priming fluid is introduced from the tube 9. The priming fluid flows through the tube 9, the flow channel 71 of the luer main body 7, the flow channel 11 of the male luer 10, the through hole 103 of the adapter 100, and the through hole 152 of the drain connector 150 in sequence, and then enters the container. When the priming fluid flows into these members, air that has been present in the members is discharged through the drain connector 150 to the outside. As described above, since a liquid-tight seal is formed between the annular rib 119a of the adapter 100 and the upper surface 43 of the cover 4 (see FIG. 16C), the priming fluid will not leak between them.

After a series of members from the tube 9 to the drain connector 150 are filled with the priming fluid, the tube 9 is squeezed by, e.g., a clamp (not shown) to close the flow channel. Then, a force F (see FIG. 2F) is applied to a pair of operating portions 35 of the male connector 1 in the direction in which they come close to each other, so that the levers 30 are pivoted to release the engagement of the claws 32 with the second projection 112. In this state, when the male connector 1 and the adapter 100 are pulled apart from each other, the adapter 100 to which the drain connector 150 is attached can be disconnected from the male connector 1. Once the adapter 100 is removed, the cover 4 immediately expands and returns to the initial state (see FIG. 8B) due to its elastic recovery force, and the inner circumferential surface of the head portion 42 closes the openings of the lateral holes 12 of the male luer 10. Therefore, the priming fluid filled in the flow channel 11 and the lateral holes 12 of the male luer 10 will not leak to the outside. The levers 30 elastically return to the initial state upon release of the external force applied to the operating portions 35.

Consequently, the priming operation is finished. The above priming operation is performed on each of the blood removal line and the reinfusion line in the extracorporeal circuit.

Thereafter, as described above, the male connector 1 is connected to the female connector 800 (see FIGS. 11A and 11B) to form an extracorporeal circuit. Another priming operation for the female connector 800 and the tube connected thereto has been completed.

As described above, the priming fluid can be introduced into the male connector 1 while the adapter 100 is being connected to the male connector 1 at the second position.

The adapter 100 can be connected to the male connector 1 at two positions, i.e., the first position and the second position. The adapter 100 has been connected to the male connector 1 at the first position and sterilized before they are delivered to medical institutions such as hospitals. In medical institutions, the adapter 100 in the first position is pushed into the male connector 1 and shifted to the second position immediately before performing the priming operation. The priming operation is made possible only by pushing the adapter 100 into the male connector 1. It is not necessary to attach the adapter 100 to the male connector 1. Thus, the operation is very simple. Moreover, the adapter 100 does not have to be previously prepared and stored separately from the male connector 1.

Since the adapter 100 has previously been connected to the male connector 1 at the first position, there is a very low probability that bacteria will enter the flow channel 11 of the male luer 10 because of the attachment of the adapter 100 to the male connector 1.

Therefore, the use of the adapter 100 can easily and hygienically introduce the priming fluid into the male luer 10 of the lever lock male connector 1 having the cover 4.

When the adapter 100 is connected to the male connector 1 at the first position, the cover 4 is not substantially deformed and remains in the initial state. Therefore, even if the male connector 1 to which the adapter 100 is connected at the first position is allowed to stand for a long period of time, the elastic recovery force of the outer circumferential wall 45 of the cover 4 will not be reduced. This is advantageous in ensuring the function of the cover 4 that immediately returns to the initial state and closes the flow channel of the male luer 10 even if the male connector 1 is unintentionally disconnected from the female connector 800 during extracorporeal circulation.

By utilizing the drain connector 150 connected to the second end portion 102 of the adapter 100, the adapter 100 and the male connector 1 can be stably fixed to the container into which the priming fluid is to be discharged.

In the first priming method, the adapter 100 is connected to one end of the drain connector 150 on which the male thread 153a is provided. The adapter 100 may also be connected to the other end of the drain connector 150 on which the male thread 153b is provided. The priming fluid is also allowed to flow from the male luer 121 of the adapter 100 without using the drain connector 150.

[Second Priming Method]

Figure 19:
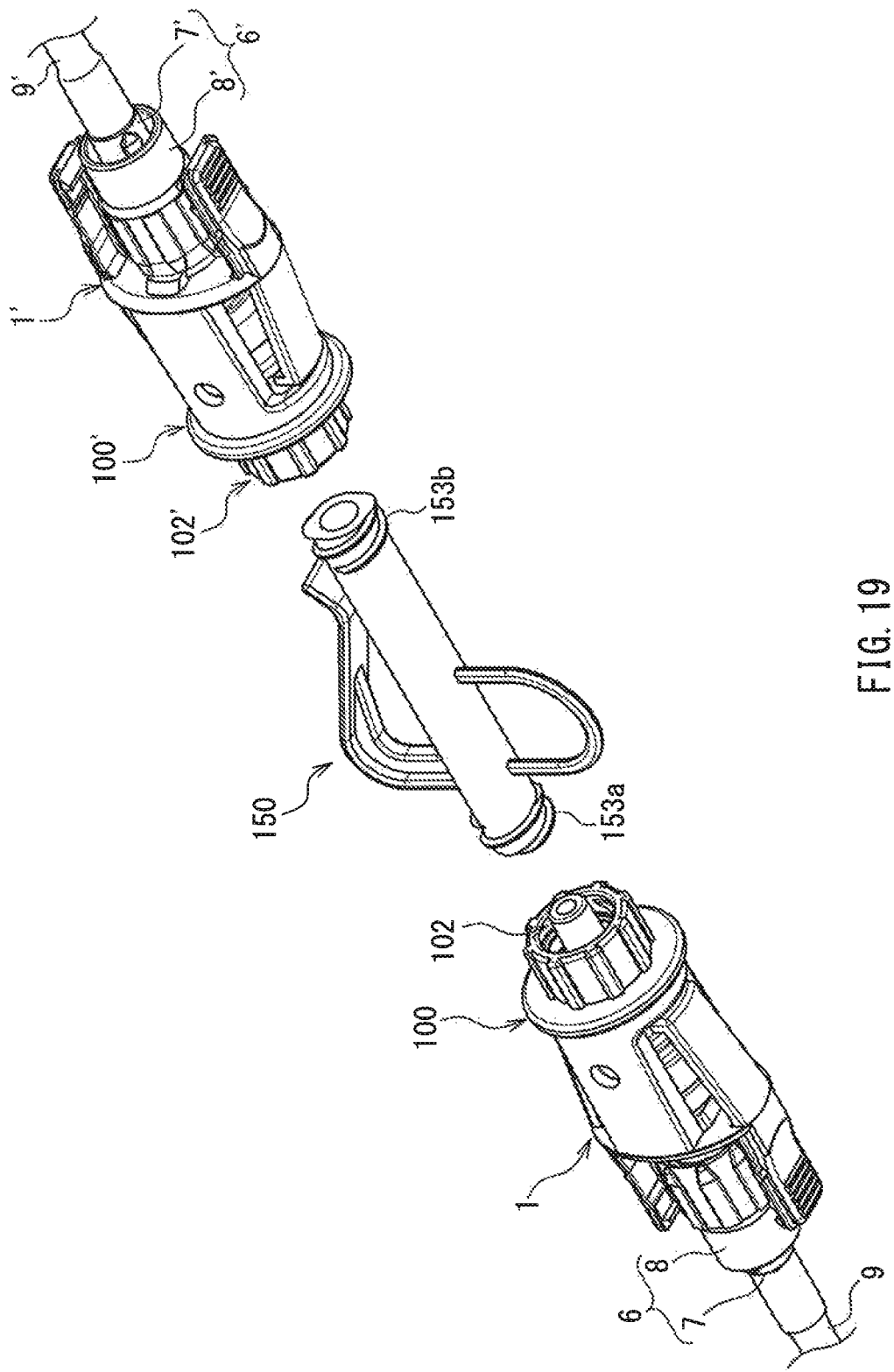
FIG. 19 is a perspective view showing a state immediately before performing a second priming method for the male connectors using the adapters according to Embodiment 1 of the present invention.

FIG. 19 is a perspective view showing a state immediately before performing a second priming method. In the second priming method, two sets of the male connector 1 to which the adapter 100 is connected at the second position, as shown in FIGS. 16A to 16C, are prepared. The following description refers to the drawings in which the members that are located on both sides of the drain connector 150 are distinguished by marking the members that are on the same side as the male thread 153b with an apostrophe ('). The members marked with an apostrophe (') are the same as those denoted by the same reference numerals without an apostrophe (').

For example, the male connector 1 and the tube 9 connected to the male connector 1 may constitute the blood removal line in the extracorporeal circuit. On the other hand, the male connector 1' and the tube 9' connected to the male connector 1' may constitute the reinfusion line in the extracorporeal circuit.

Figure 20A:
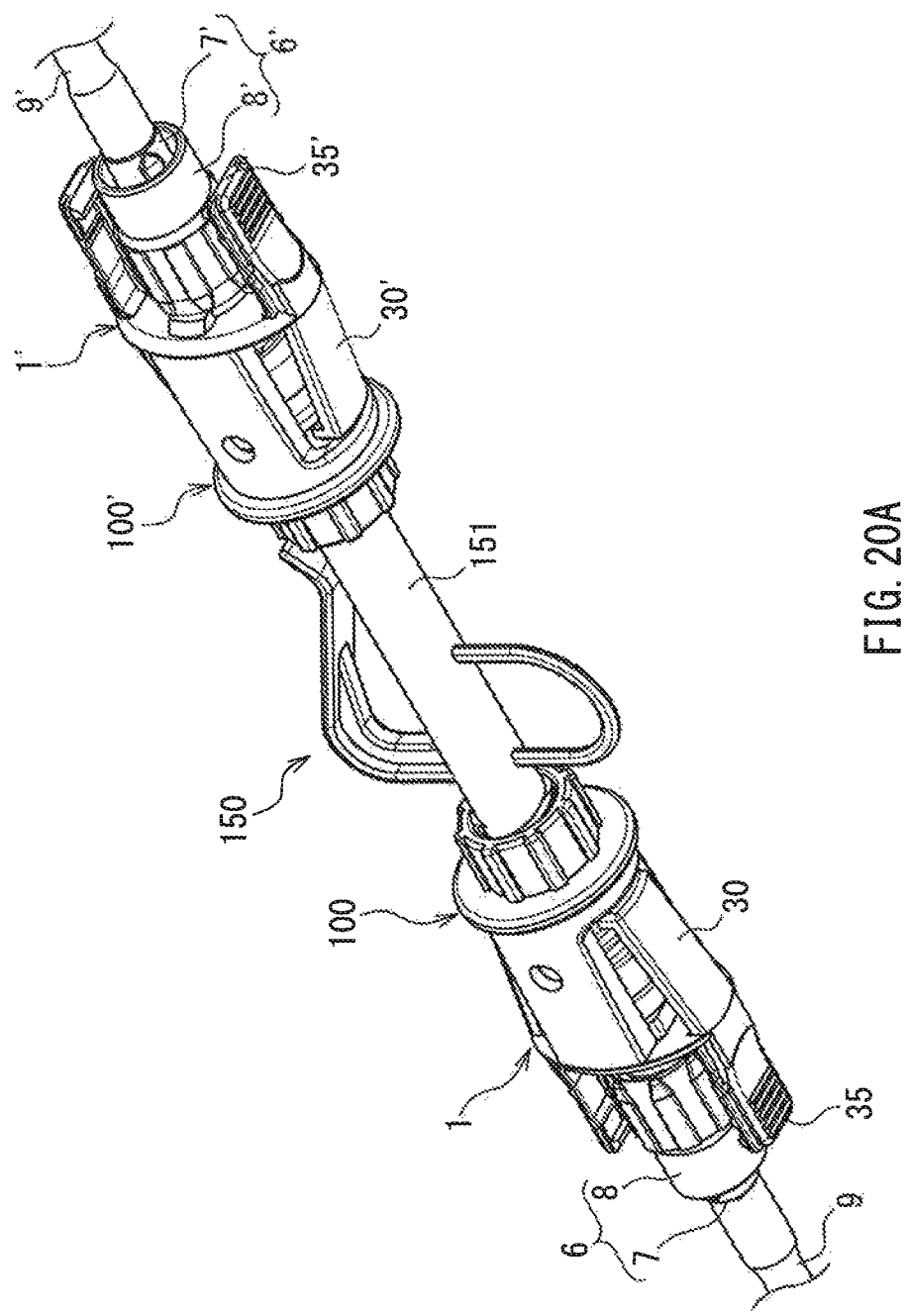
FIG. 20A is a perspective view for explaining the second priming method for the male connectors using the adapters according to Embodiment 2 of the present invention.
Figure 20B:
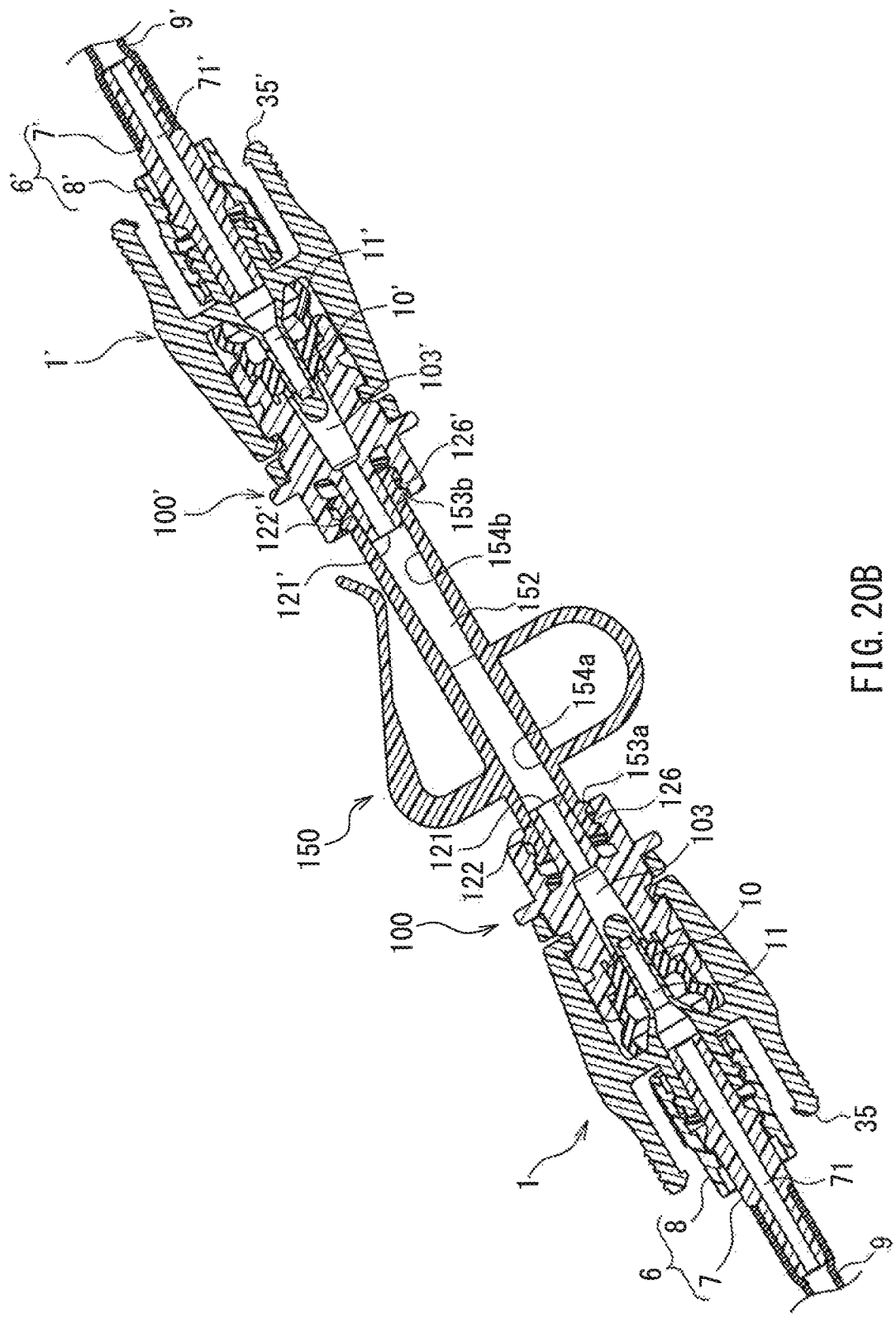
FIG. 20B is a cross-sectional view of FIG. 20A

Next, as shown in FIG. 20A the adapter 100 connected to the male connector 1 is connected to one end of the drain connector 150 having the male thread 153a, and the adapter 100' connected to the male connector 1' is connected to the other end of the drain connector 150 having the male thread 153b. FIG. 20B is a cross-sectional view of FIG. 20A The male thread 153a and the female tapered surface 154a of the drain connector 150 are fitted to the female thread 126 and the male tapered surface 122 of the adapter 100. The male thread 153b and the female tapered surface 154b of the drain connector 150 are fitted to the female thread 126' and the male tapered surface 122' of the adapter 100'. Therefore, the male luer 121, the drain connector 150, and the male luer 121' are connected to one another in a liquid-tight manner.

In this state, a priming fluid is introduced from the tube 9. The priming fluid flows through the tube 9, the flow channel 71 of the luer main body 7, the flow channel 11 of the male luer 10, the through hole 103 of the adapter 100, the through hole 152 of the drain connector 150, the through hole 103' of the adapter 100', the flow channel 11' of the male luer 10', the flow channel 71' of the luer main body 7', and the tube 9' in sequence, and then exits from the distal end (not shown) of the tube 9' to the outside. When the priming fluid flows into these members, air that has been present in the members is discharged through the distal end of the tube 9' to the outside.

After a series of members from the tube 9 at one end to the tube 9' at the other end are filled with the priming fluid, the tubes 9, 9' are squeezed by, e.g., clamps (not shown) to close their respective flow channels. Then, a force F (see FIG. 2F) is applied to a pair of operating portions 35 of the male connector 1 in the direction in which they come close to each other, so that the levers 30 are pivoted to release the engagement (see FIG. 16B) of the claws 32 with the second projection 112. In this state, when the male connector 1 and the adapter 100 are pulled apart from each other, the adapter 100 to which the drain connector 150 is attached can be disconnected from the male connector 1. Once the adapter 100 is removed, the cover 4 immediately expands and returns to the initial state (see FIG. 8B) due to its elastic recovery force, and the inner circumferential surface of the head portion 42 closes the openings of the lateral holes 12 of the male luer 10. Therefore, the priming fluid filled in the flow channel 11 and the lateral holes 12 of the male luer 10 will not leak to the outside. The levers 30 elastically return to the initial state upon release of the external force applied to the operating portions 35. The adapter 100' is disconnected from the male connector 1' in the same manner as described above.

Consequently, the priming operation is finished.

Thereafter, as described above, the male connectors 1, 1' are connected to different female connectors 800 (see FIGS. 11A and 11B) to form extracorporeal circuits, respectively. Another priming operation for the female connectors 800 and the tubes connected thereto has been completed.

Similarly to the first priming method, the second priming method also uses the adapter 100 and can easily and hygienically introduce the priming fluid into the male luer 10 of the lever lock male connector 1 having the cover 4. Even if the male connector 1 to which the adapter 100 is connected at the first position is allowed to stand for a long period of time, the elastic recovery force of the outer circumferential wall 45 of the cover 4 will not be reduced. This can ensure the function of the cover 4.

Further, in the second priming method, the male connector 1 and the male connector 1' are in communication with each other via the drain connector 150. Thus, the priming fluid can be simultaneously introduced into, e.g., the male connector 1 for the blood removal line and the male connector 1' for the reinfusion line. Accordingly, the priming operation can be efficiently performed.

In the first and second priming methods, the drain connector 150 is connected to the adapter 100 (100') after the adapter 100 (100') has been shifted from the first position to the second position. However, the present invention is not limited thereto, and the drain connector 150 may be connected to the adapter 100 (100') that is in the first position (see FIG. 15), and then the adapter 100 (100') may be shifted to the second position.

Embodiment 2

1. Configuration of Adapter

Figure 21A:
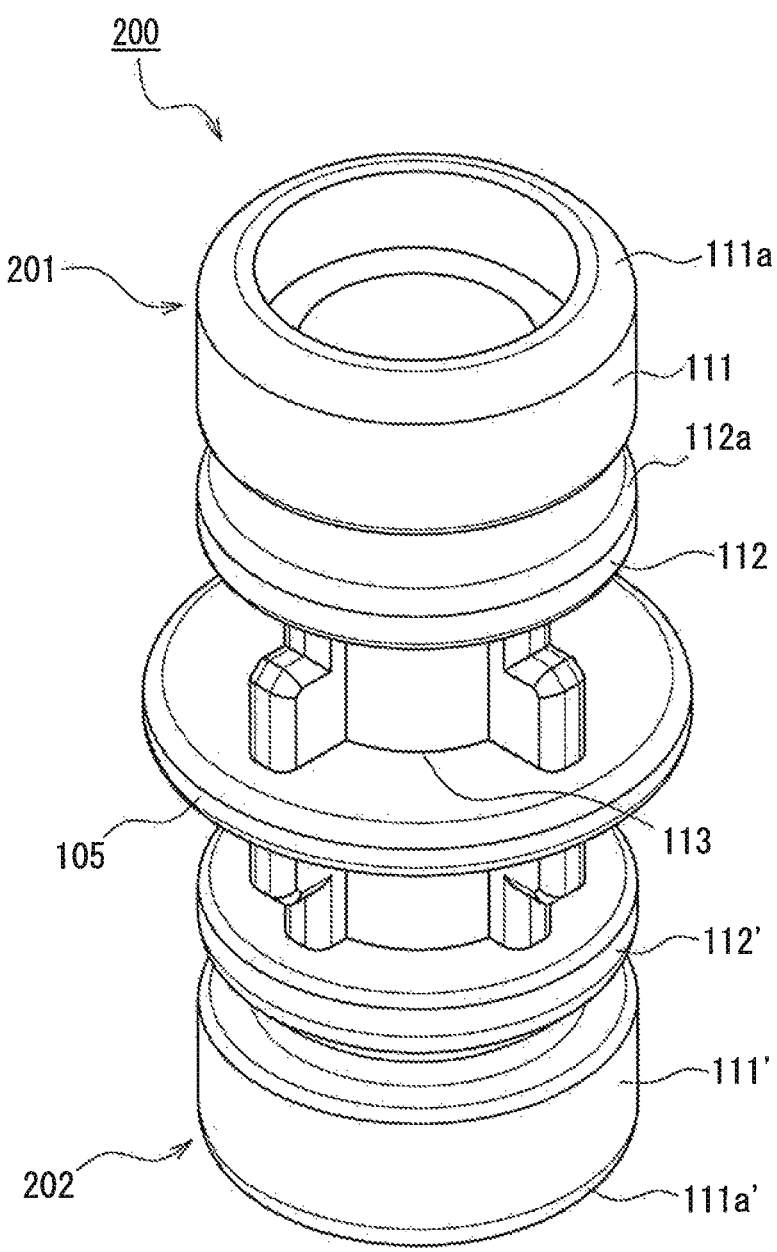
FIG. 21A is a perspective view of an adapter according to Embodiment 2 of the present invention.
Figure 21B:
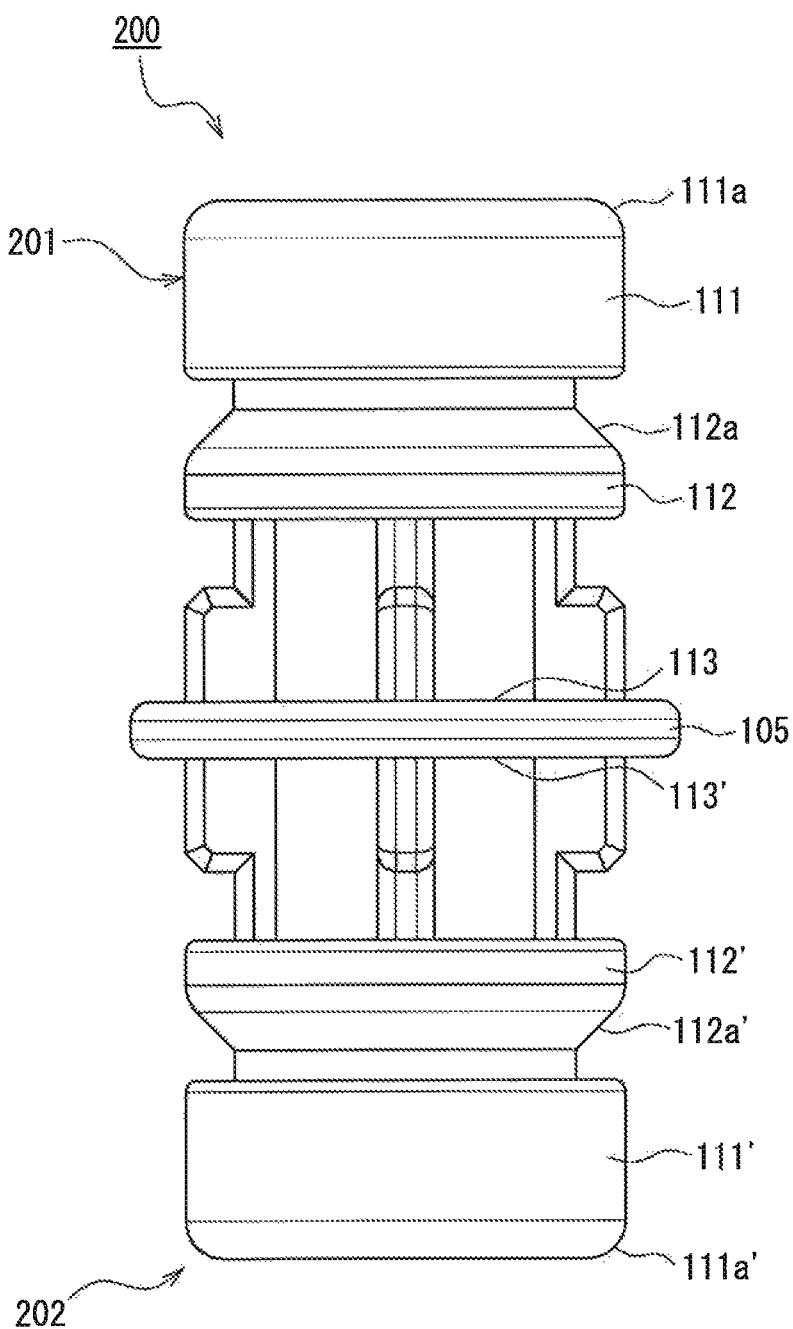
FIG. 21B is a side view of the adapter according to Embodiment 2 of the present invention.
Figure 21C:
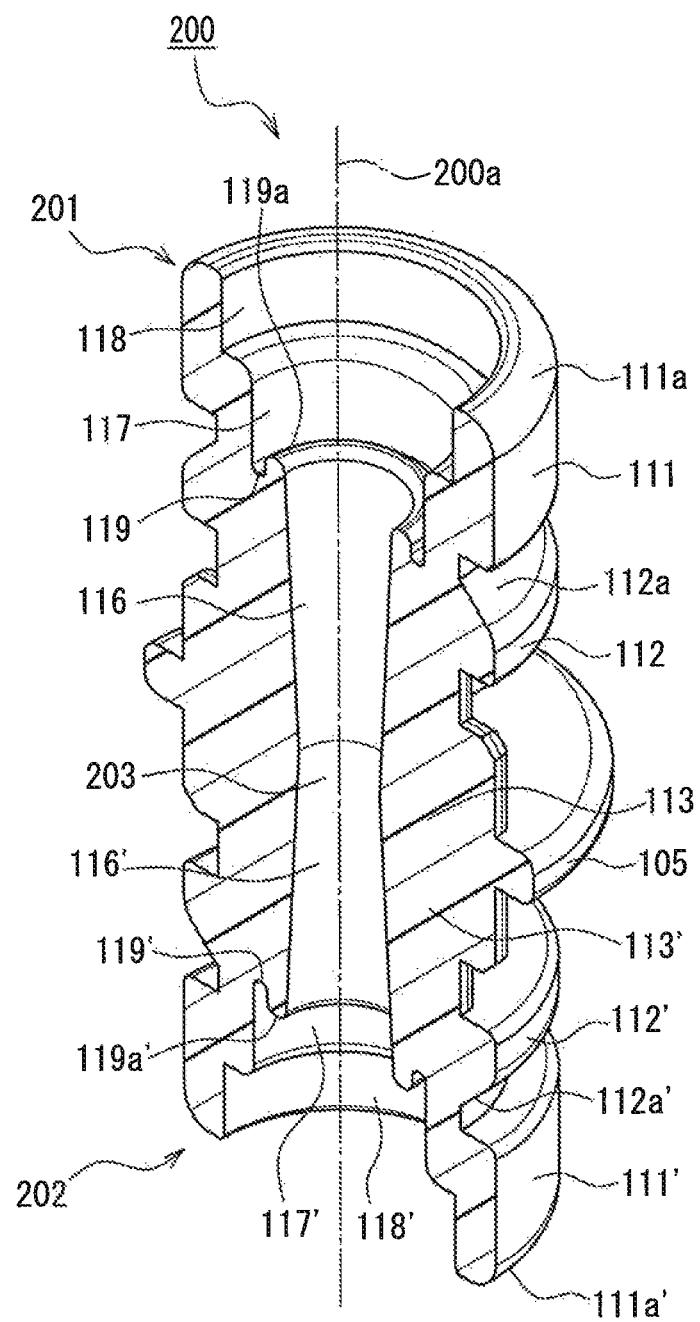
FIG. 21C is a cross-sectional perspective view of the adapter according to Embodiment 2 of the present invention.

FIG. 21A is a perspective view of an adapter 200 according to Embodiment 2 of the present invention. FIG. 21B is a side view of the adapter 200. FIG. 21C is a cross-sectional perspective view of the adapter 200. In FIG. 21C, an alternate long and short dash line 200a represents a central axis of the adapter 200 joining a first end portion 201 and a second end portion 202. For the sake of convenience of the following description, the direction that is orthogonal to the central axis 200a is referred to as a "radial direction" or a "diameter direction", and the direction of rotation about the central axis 200a is referred to as a "circumferential direction". With respect to the radial direction, the side nearer the central axis 200a is referred to as the "inner side", and the side further from the central axis 200a is referred to as the "outer side".

As shown in FIG. 21C, similarly to the adapter 100 in Embodiment 1, the adapter 200 has a through hole (flow channel) 203 that penetrates the adapter 200 along the central axis 200a. The through hole 203 is open in both the first end portion 201 and the second end portion 202 of the adapter 200, and allows the first end portion 201 to be in communication with the second end portion 202.

The adapter 200 in Embodiment 2 is obtained by modifying the adapter 100 (FIGS. 12A to 12D) in Embodiment 1 so that the configuration provided on the second end portion 102 side with respect to the large diameter portion 105 is made the same as that provided on the first end portion 101 side with respect to the large diameter portion 105. In other words, the first end portion 201 and the second end portion 202 of the adapter 200 in Embodiment 2 have the same configuration as that of the first end portion 101 of the adapter 100 in Embodiment 1. The adapter 200 is symmetrical with respect to the large diameter portion 105 in the center. In the adapter 200 in Embodiment 2, the same components as those of the adapter 100 in Embodiment 1 are denoted by the same reference numerals, and a detailed description about them will not be repeated. However, in order to distinguish between the components on the first end portion 201 side and the components on the second end portion 202 side with respect to the large diameter portion 105, the components on the second end portion 202 side are marked with an apostrophe ('). The components marked with an apostrophe (') are the same as those denoted by the same reference numerals without an apostrophe (').

The adapter 200 can be integrally produced as a single component through injection molding or the like using the same material as that of the adapter 100 in Embodiment 1.

Figure 22:
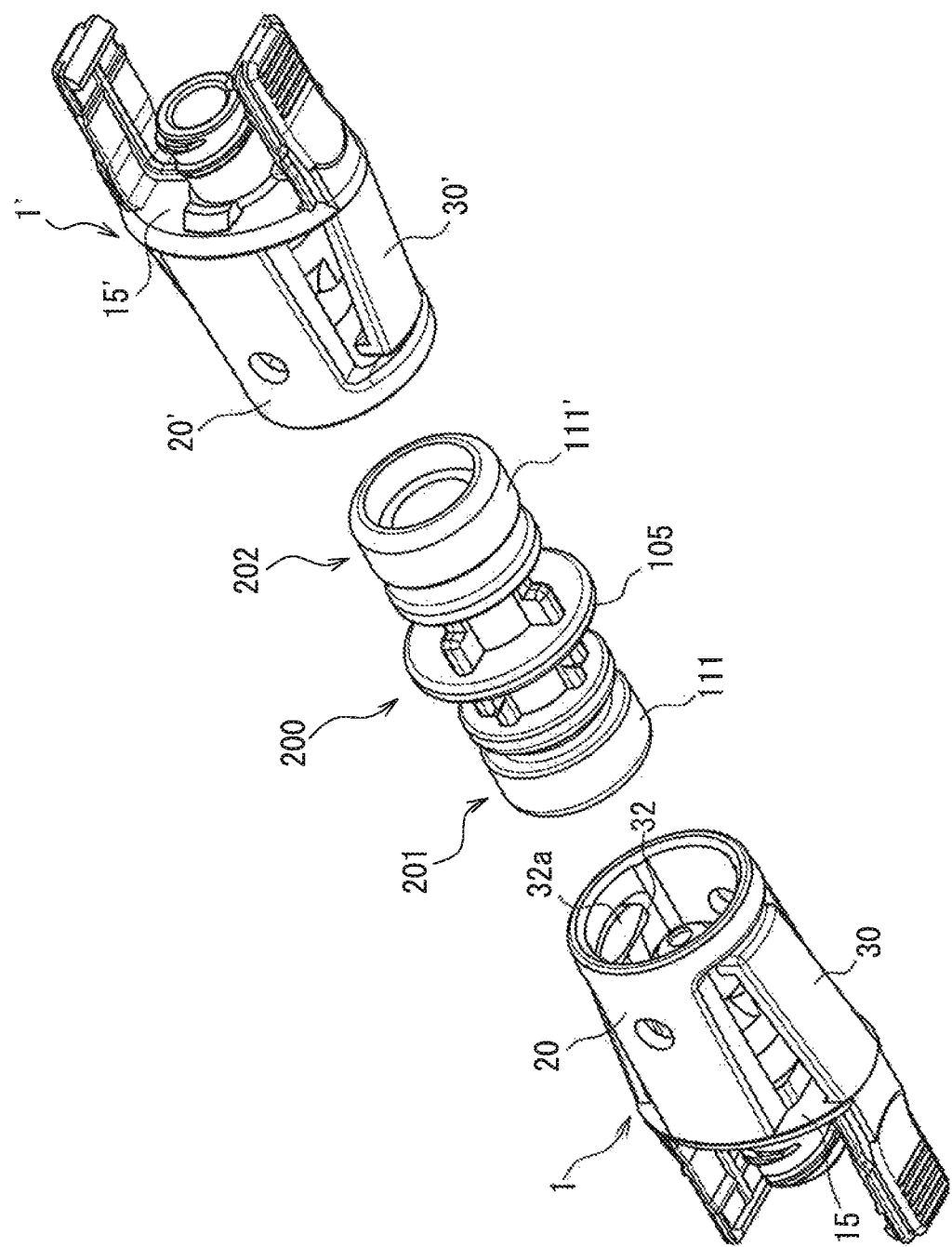
FIG. 22 is a perspective view of the adapter according to Embodiment 2 of the present invention immediately before it is connected to male connectors.

2. Method for Using Adapter 2.1 Connection of Adapter to Male Connector at First Position In this embodiment, male connectors 1 are connected to both end portions 201, 202 of the adapter 200. FIG. 22 is a perspective view showing a state immediately before connecting the male connectors 1. The following description refers to the drawings in which the members that are located on both sides of the adapter 200 are distinguished by marking the members that are on the same side as the second end portion 202 with an apostrophe ('). The members marked with an apostrophe (') are the same as those denoted by the same reference numerals without an apostrophe ('). As shown in FIG. 22, the screw lock connector 6 and the tube 9 are not connected to the male connectors 1, 1' at this stage.

Figure 23A:
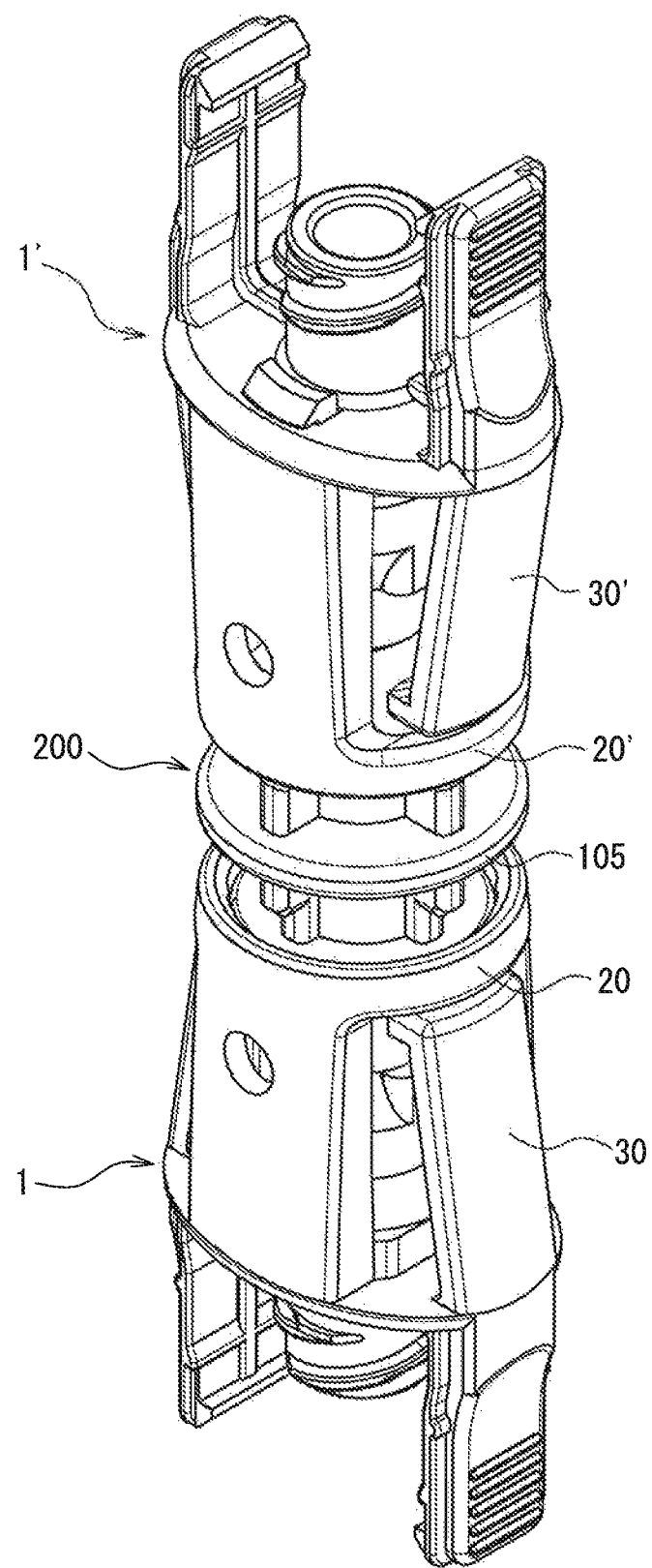
FIG. 23A is a perspective view of the adapter according to Embodiment 2 of the present invention when it is attached to the male connectors at the first position.
Figure 23B:
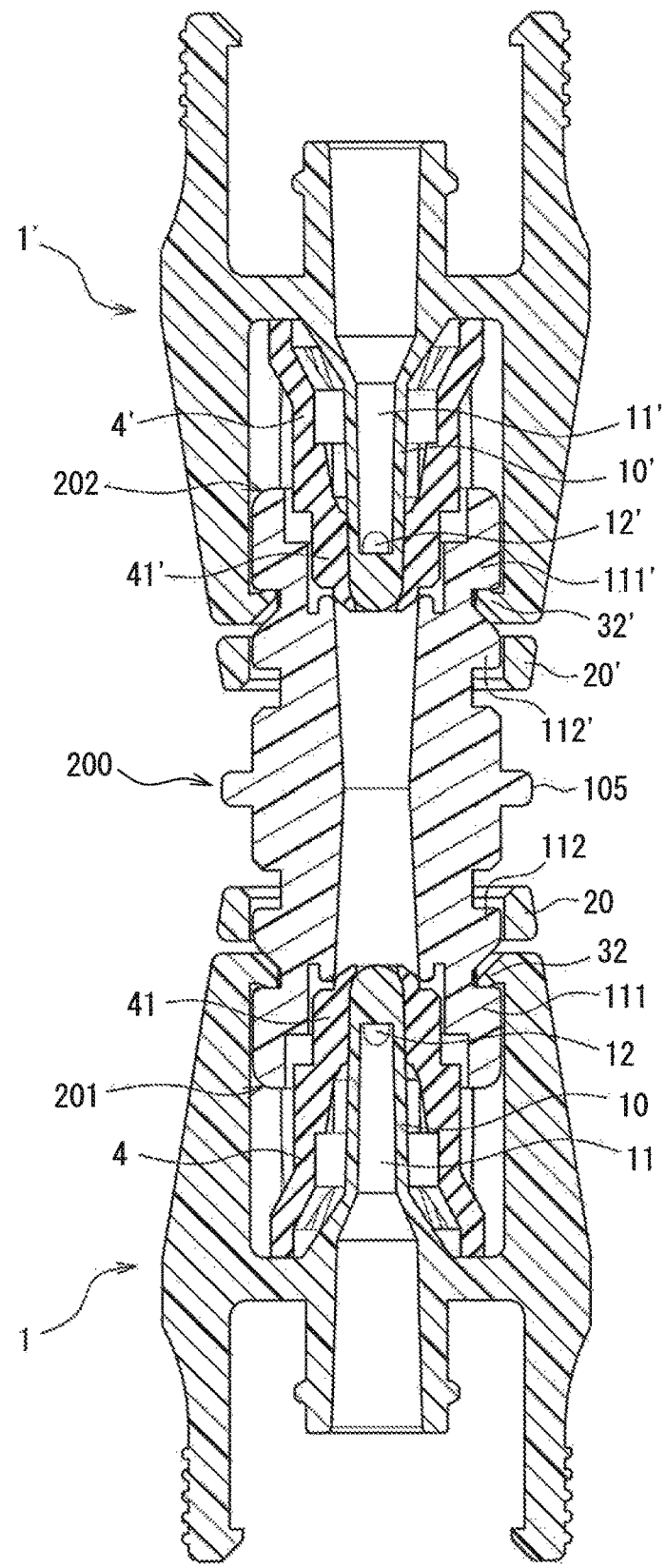
FIG. 23B is a cross-sectional view of the adapter and the male connectors shown in FIG. 23A.
Figure 23C:
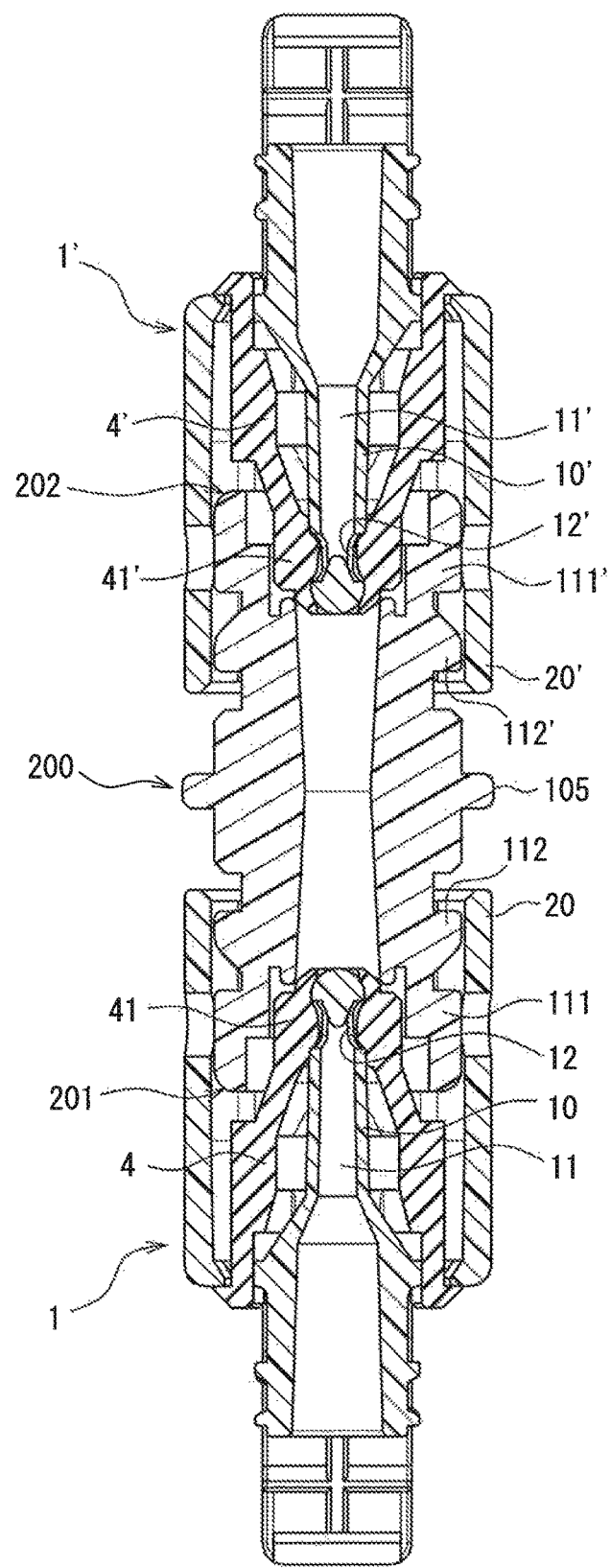
FIG. 23C is another cross-sectional view of the adapter and the male connectors shown in FIG. 23A.

From the state shown in FIG. 22, similarly to Embodiment 1, the first end portion 201 is connected to the male connector 1 and the second end portion 202 is connected to the male connector 1'. FIG. 23A is a perspective view showing the connected state. FIGS. 23B and 23C are cross-sectional views of FIG. 23A The cross section in FIG. 23B is the same as that in FIG. 4B. The cross section in FIG. 23C is the same as that in FIG. 4C. Both the state of connection between the first end portion 201 and the male connector 1 and the state of connection between the second end portion 201 and the male connector 1', as shown in FIGS. 23A to 23C, are the same as the state of connection between the first end portion 101 and the male connector 1 at the first position in Embodiment 1 (FIGS. 14A to 14C). Specifically, the claws 32, 32' of the male connectors 1, 1' are engaged with the first projections 111, 111' of the adapter 200, respectively. The flow channels 11, 11' of the male luers 10, 10' are sealed with the head portions 41, 41' of the covers 4, 4'.

The male connectors 1, 1' and the adapter 200 are sterilized and packaged in a state in which the male connectors 1, 1' are connected to both ends of the adapter 200 at the first position (see FIGS. 23A to 23C). The sterilization and packaging processes may be carried out by manufacturers and distributors of the male connectors 1, 1'. The male connectors 1, 1' coupled together via the adapter 200, which have been sterilized and packaged, are delivered and stored in medical institutions such as hospitals.

The same explanation given for the connection of the adapter 100 to the male connector 1 at the first position in Embodiment 1 can also be applied to Embodiment 2.

2.2 Priming

When an extracorporeal circuit is formed in medical institutions, the packaging containing the male connectors 1, 1' and the adapter 200 is torn open, and the male connectors 1, 1' (see FIGS. 23A to 23C) to which the adapter 200 is connected at the first position is taken out.

Figure 24:
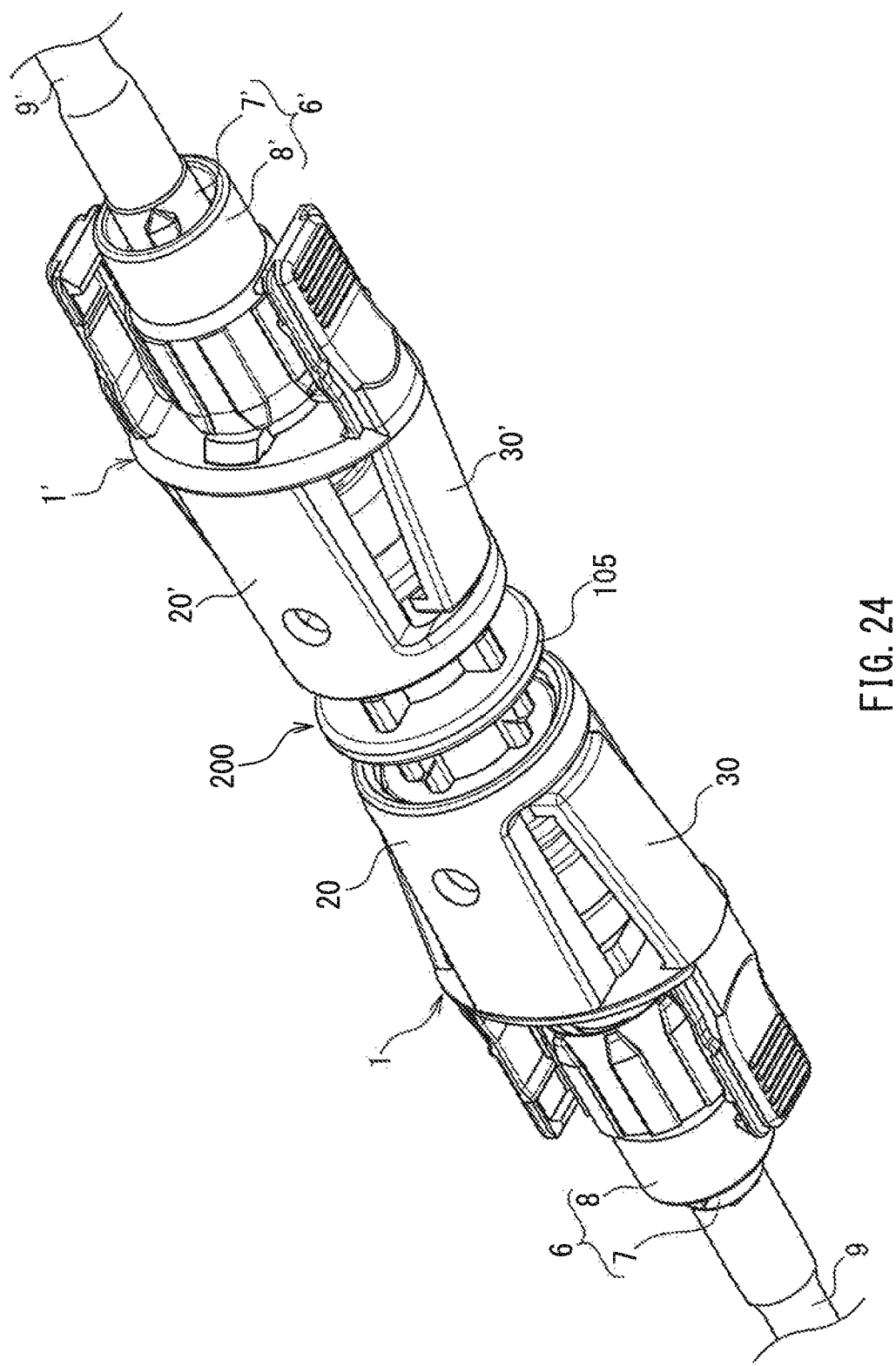
FIG. 24 is a perspective view showing a state in which a tube constituting an extracorporeal circuit is connected to each of the male connectors to which the adapter according to Embodiment 2 of the present invention is connected at the first position.

As shown in FIG. 24, the screw lock connectors 6, 6' attached to the distal ends of the tubs 9, 9' are connected to the male connectors 1, 1', respectively. For example, the tube 9 may constitute the blood removal line and the tube 9' may constitute the reinfusion line in the extracorporeal circuit. The adapter 200 is still in the first position relative to the male connectors 1, 1'.

Next, the adapter 200 is pushed toward the male connectors 1, 1'. Specifically, while holding the male connector 1 and the male connector 1', forces are applied to them in directions facing each other. Then, the levers 30 are displaced (swung) in the same manner as described in Embodiment 1, so that the claws 32, 32' are fitted in the respective annular grooves that are formed between the second projections 112, 112' and the large diameter portion 105 of the adapter 200 and continuously extend in the circumferential direction.

Figure 25A:
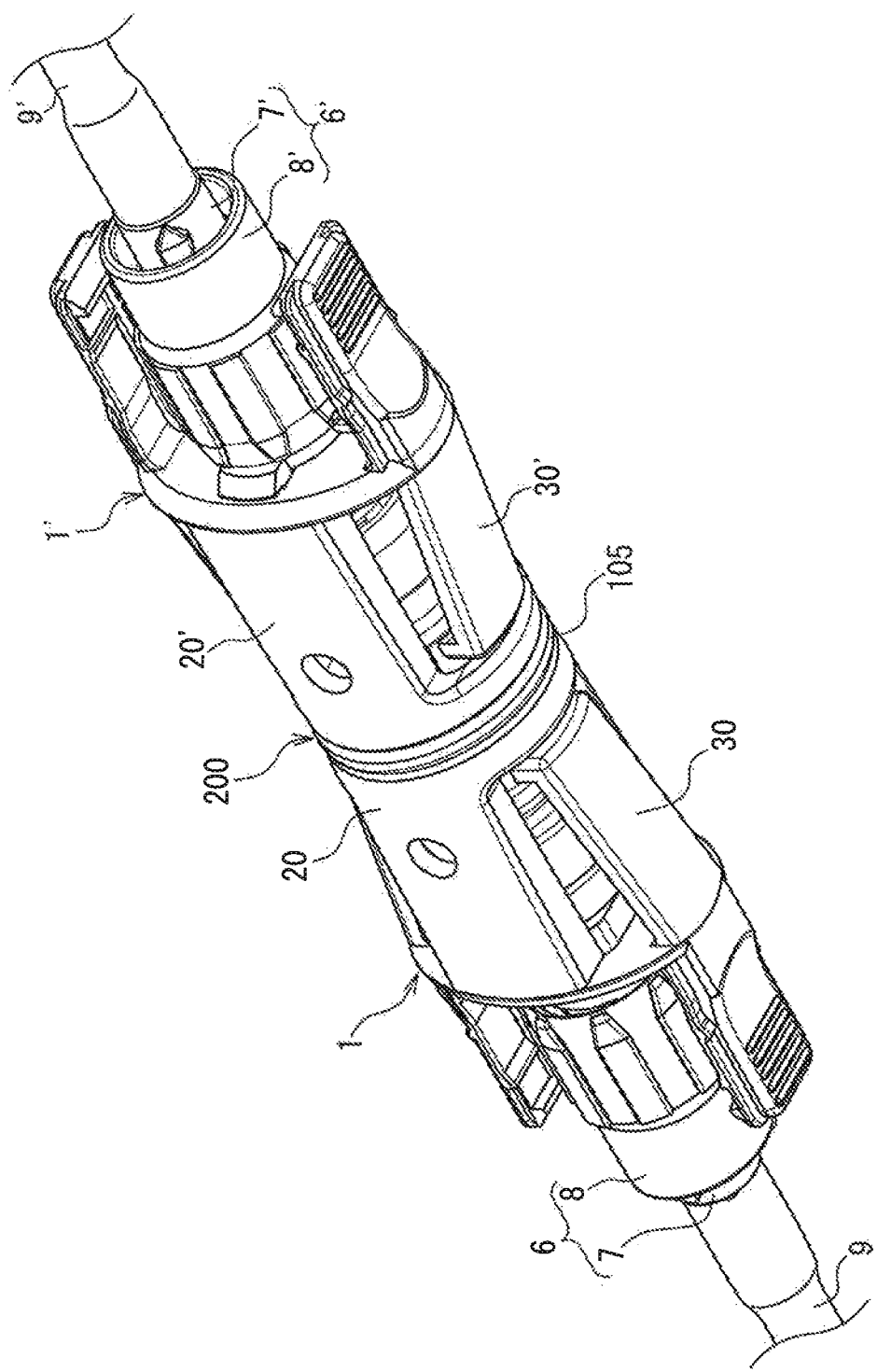
FIG. 25A is a perspective view showing a state in which the adapter according to Embodiment 2 of the present invention is attached to the male connectors at the second position while the tube constituting an extracorporeal circuit is being connected to each of the male connectors.
Figure 25B:
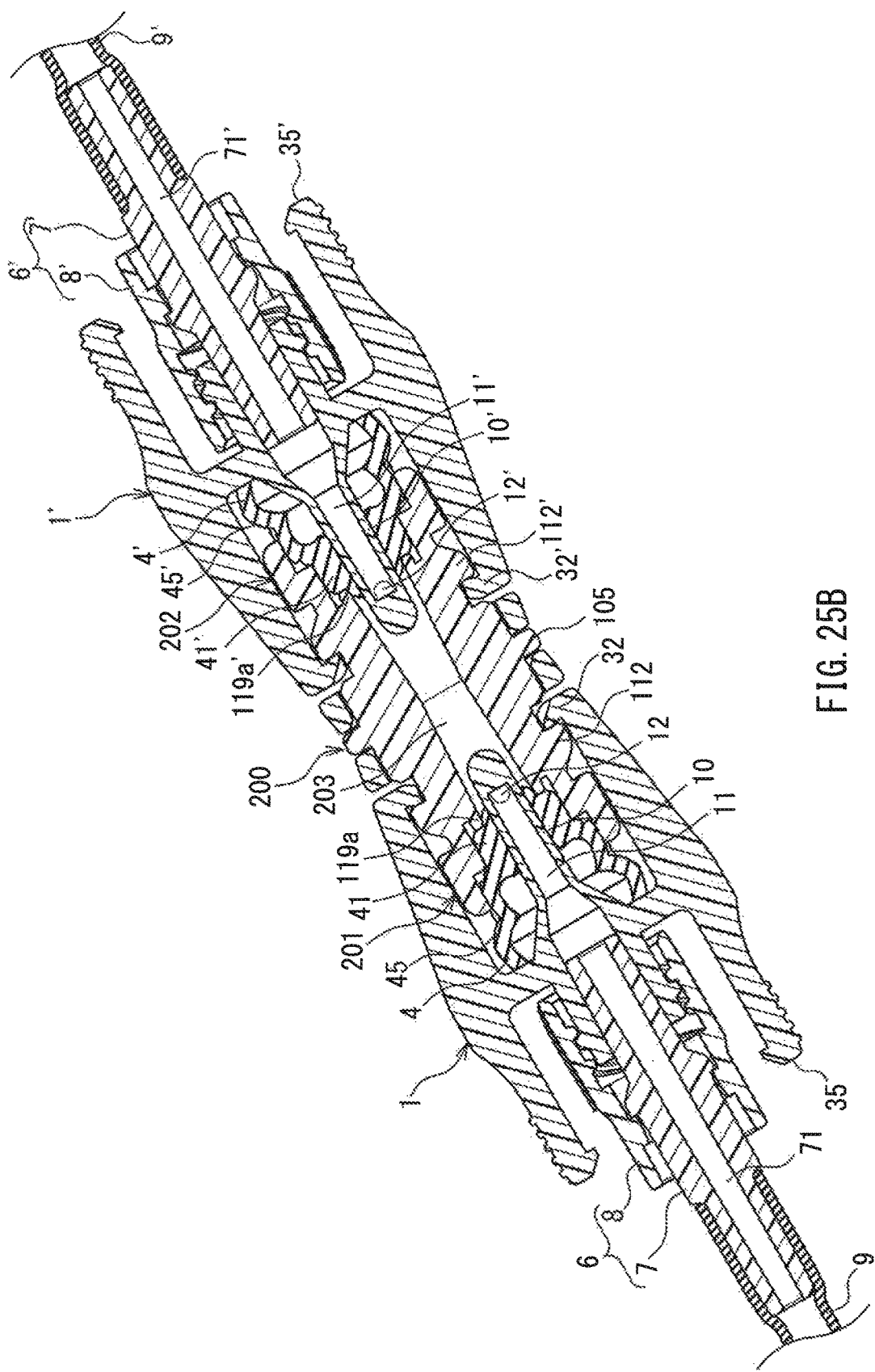
FIG. 25B is a cross-sectional view of the adapter and the male connectors shown in FIG. 25A.
Figure 25C:
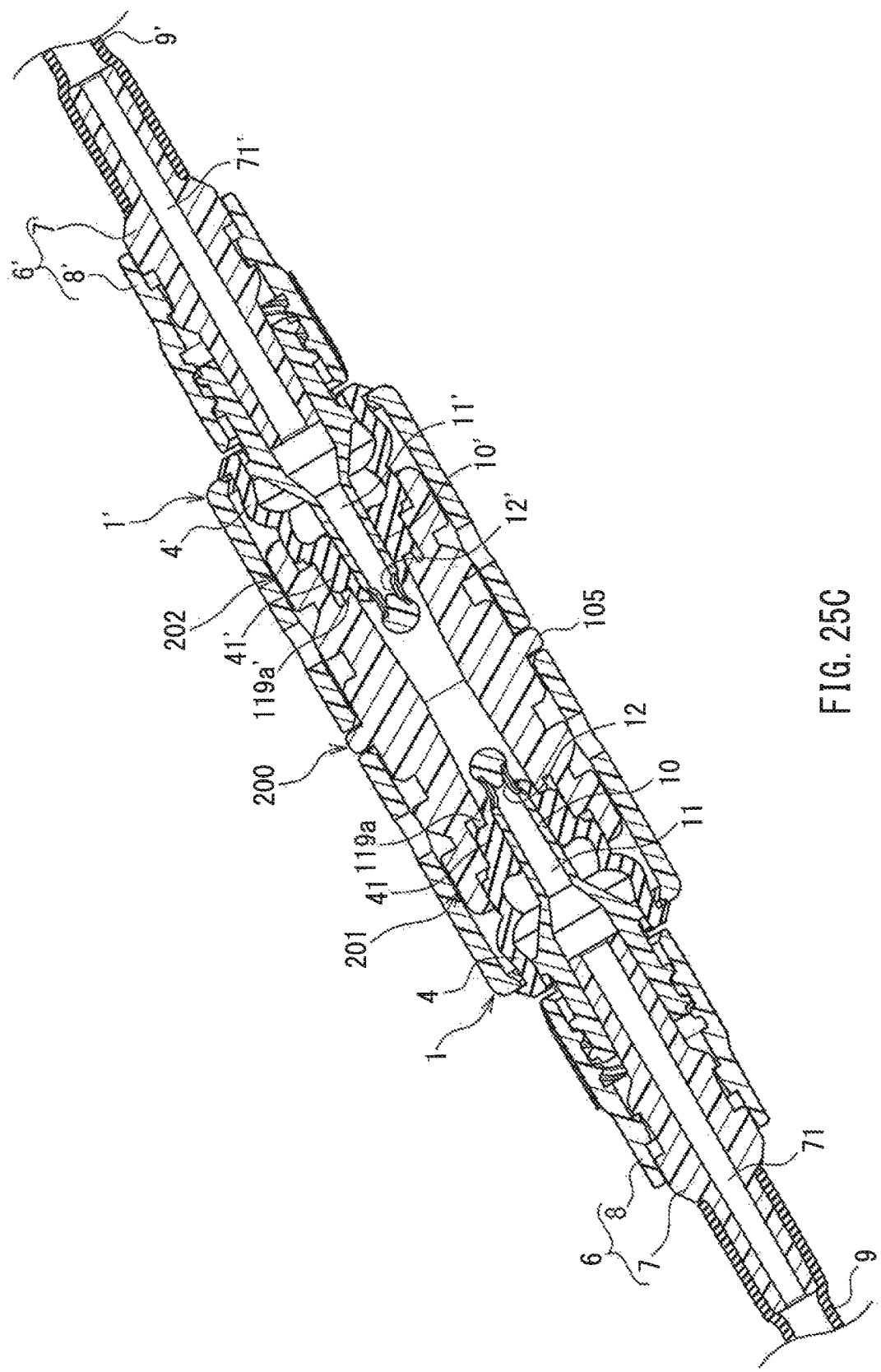
FIG. 25C is another cross-sectional view of the adapter and the male connectors shown in FIG. 25A.

FIG. 25A is a perspective view showing this state. FIGS. 25B and 25C are cross-sectional views of the state. The cross section in FIG. 25B is the same as that in FIGS. 4B and 23B. The cross section in FIG. 25C is the same as that in FIGS. 4C and 23C. The state of connection between the first end portion 201 and the male connector 1 and the state of connection between the second end portion 202 and the male connector 1', as shown in FIGS. 25A to 25C, are the same as the state of connection between the first end portion 101 and the male connector 1 at the second position in Embodiment 1 (FIGS. 16A to 16C). Specifically, the claws 32, 32' of the male connectors 1, 1' are engaged with the second projections 112, 112' of the adapter 200, respectively. The outer circumferential walls 45, 45' of the covers 40, 40' are elastically and compressively deformed in the vertical direction. The flow channels 11, 11' of the male luers 10, 10' are in communication with the through hole 203 of the adapter 200. Liquid-tight seals are formed between the annular ribs 119a, 119a' of the adapter 200 and the upper surfaces of the head portions 41, 41' of the covers 4, 4', respectively.

The same explanation given for the connection of the adapter 100 to the male connector 1 at the second position in Embodiment 1 can also be applied to Embodiment 2.

Since the adapter 200 has been moved to the second position (see FIGS. 25A to 25C), the lateral holes 12, 12' of the male luers 10, 10' are open. Therefore, a priming fluid can be introduced into the male connectors 1, 1'.

The priming operation can be performed in the same manner as the second priming method in Embodiment 1. In the state shown in FIGS. 25A to 25C, a priming fluid is introduced from the tube 9. The priming fluid flows through the tube 9, the flow channel 71 of the luer main body 7, the flow channel 11 of the male luer 10, the through hole 203 of the adapter 200, the flow channel 11' of the male luer 10', the flow channel 71' of the luer main body 7', and the tube 9' in sequence, and then exits from the distal end (not shown) of the tube 9' to the outside. When the priming fluid flows into these members, air that has been present in the members is discharged through the distal end of the tube 9' to the outside.

After a series of members from the tube 9 at one end to the tube 9' at the other end are filled with the priming fluid, the tubes 9, 9' are squeezed by, e.g., clamps (not shown) to close their respective flow channels. Then, each of the male connectors 1, 1' is disconnected from the adapter 200 in the same manner as Embodiment 1. Once the adapter 200 is removed, the covers 4, 4' immediately expand and return to the initial state (see FIG. 8B) due to their elastic recovery forces, thereby closing the openings of the lateral holes 12, 12' of the male luers 10, 10'. Therefore, the priming fluid will not leak from the male luers 10, 10' to the outside.

Consequently, the priming operation is finished.

Thereafter, similarly to Embodiment 1, the male connectors 1, 1' are connected to different female connectors 800 (see FIGS. 11A and 11B) to form extracorporeal circuits, respectively. Another priming operation for the female connectors 800 and the tubes connected thereto has been completed.

Similarly to Embodiment 1, Embodiment 2 also uses the adapter 200 and can easily and hygienically introduce the priming fluid into the male luers 10, 10' of the lever lock male connector 1, 1' having the covers 4, 4'. Even if the male connectors 1, 1' to which the adapter 200 is connected at the first position are allowed to stand for a long period of time, the elastic recovery forces of the outer circumferential walls 45, 45' of the covers 4, 4' will not be reduced. This can ensure the function of the covers 4, 4'.

Further, the male connector 1 and the male connector 1' are in communication with each other via the adapter 200. Thus, the priming fluid can be simultaneously introduced into, e.g., the male connector 1 for the blood removal line and the male connector 1' for the reinfusion line. Accordingly, the priming operation can be efficiently performed. The second priming method in Embodiment 1 requires two adapters 100, 100' and the drain connector 150, and further requires an operation for connecting the adapters 100, 100' and the drain connector 150. In contrast, Embodiment 2 uses only a single component, i.e., the adapter 200 to simultaneously introduce the priming fluid into two male connectors 1, 1' by a simple operation procedure.

In Embodiment 2, the male connectors 1, 1' are connected to both ends of the adapter 200. However, the present invention is not limited thereto, and the priming operation may be performed on the male connector 1 in the same manner as the first priming method in Embodiment 1 by connecting the male connector 1 to the first end portion 201 of the adapter 200 while the male connector 1' is not connected to the second end portion 202.

In the adapter 200 in Embodiment 2, the base end 113 of the tubular portion 110 of the first end portion 201 coincides with the base end 113' of the tubular portion 110' of the second end portion 202, and the first end portion 201 and the second end portion 202 share the single large diameter portion 105. However, the present invention is not limited thereto, and the based end 113 of the tubular portion 110 may be spaced apart from the base end 113' of the tubular portion 110' in the direction of the central axis 200a. In this case, the base end 113 and the base end 113' are coupled with a hollow member in which the through hole 203 is provided. The large diameter portions (a first large diameter portion and a second large diameter portion) 105 are provided at the respective positions of the base end 113 and the base end 113'. The first end portion 201 including the first large diameter portion 105 is configured symmetrically to the second end portion 202 including the second large diameter portion 105.

It should be understood that Embodiments 1, 2 are given by way of example only. The present invention is not limited to Embodiments 1, 2, and modifications can be made thereto as appropriate.

It is possible to freely change how the liquid-tight seal is formed between the cover 4 and each of the tubular portions 110 of the adapters 100, 200 when the adapters 100, 200 are in the second position.

For example, the annular rib 119a (119') that protrudes from the shoulder portion 119 (119') of the adapters 100, 200 may be omitted. In this case, the shoulder portion 119 (119') directly abuts against the head portion 41 of the cover 4 when the adapters 100, 200 are in the second position, and thus a liquid-tight seal can be formed between them.

The head portion 41 of the cover 4 does not need to have the upper surface 43 that is parallel to the horizontal direction. Even if the surface of the head portion 41 that faces upward is, e.g., a spherical surface or a circular conical surface, a liquid-tight seal can be formed between such a surface and the tubular portion 110.

In the above embodiments, when the adapters 100, 200 are connected to the male connector 1 at the first position and the second position, the head portion 41 of the cover 4 is inserted into the second region 117 and the third region 118 of the tubular portion 110. However, the second region 117 and the third region 118 may be omitted. In this case, a liquid-tight seal is formed between the leading end of the tubular portion 110 and the head portion 41 of the cover 4 when the adapters 100, 200 are in the second position.

The large diameter portion 150 of the adapters 100, 200 may be omitted.

The tapered surface 112a of the second projection 112 of the adapters 100, 200 may be omitted. Even in the absence of the tapered surface 112a, when the claws 32 include the inclined surfaces 32a, the adapters 100, 200 can be moved from the first portion to the second position only by pushing the adapters 100, 200 into the male connector 1.

The female thread 126 formed on the inner circumferential surface of the outer cylinder 125 of the adapter 100 may be omitted. Moreover, the outer cylinder 125 may be omitted. If the second end portion 102 includes only the male luer 121, the male tapered surface 122 of the male luer 121 can be connected to the female tapered surfaces 154a, 154b of the drain connector 150 in a liquid-tight manner.

The configuration of the male connector 1 is not limited to the above embodiments. The adapter of the present invention can be applied to any lever lock male connector including a lever with a claw to be engaged with a female connector.

For example, the hood 20 of the male connector may have a cylindrical shape whose internal and external diameters are constant with respect to the direction of the central axis 2a, as described in Patent Document 1. The number of levers 30 having the claws 32 is not limited to two, and may be, e.g., one, as described in Patent Documents 2, 3.

The flow channel 11 of the male luer 10 may be open upward at the leading end 10a of the male luer 10, as described in Patent Document 1.

The through hole 42 formed in the head portion 41 of the cover 4 does not have to be open so that the leading end 10a of the male luer 10 is exposed in the initial state. For example, the through hole 42 may be a slit (cut portion) which looks like a minus sign ("-"), as described in Patent Documents 4, 5. In this case, the slit of the through hole 42 is closed when the male luer 10 does not penetrate the through hole 42 in the initial state.

The outer circumferential wall 45 of the cover 4 may have any shape that can be elastically and compressively deformed in the longitudinal direction of the male luer 10. For example, the outer circumferential wall 45 may be in the form of bellows, as described in Patent Document 4.

In the above embodiments, the male connector is used for the extracorporeal circuit of blood. However, the present invention is not limited thereto. The male connector to which the adapter of the present invention is connected may be a male connector that constitutes a device other than the extracorporeal circuit, e.g., an infusion set used to perform infusion.

INDUSTRIAL APPLICABILITY

While there is no particular limitation on the field of use of the present invention, the present invention can be used as desired in the field of medicine where a priming fluid needs to be introduced into a lever lock male connector having a cover. In particular, the present invention can be preferably used in the field of, e.g., extracorporeal blood circulation or infusion where some liquid (blood, infusion solution, etc.) needs to be injected into a blood vessel of a patient.

LIST OF REFERENCE NUMERALS

1 Male connector
2 Connector main body
10 Male luer (male member)
11 Flow channel of male luer
20 Hood
30 Lever (lock lever)
32 Claw
4 Cover
41 Head portion
45 Outer circumferential wall
100, 200 Adapter
101, 201 First end portion
102, 202 Second end portion
103, 203 Through hole of adapter
105 Large diameter portion
110, 110' Tubular portion
111, 111' First projection
112, 112' Second projection
112a Tapered surface
113, 113' Base end of tubular portion 119a Annular rib
121 Male luer of adapter
122 Outer circumferential surface (male tapered surface) of male luer
125 Outer cylinder
126 Female thread (screw structure)

The invention claimed is:

1. An adapter that is attachable to and detachable from a male connector,
   the male connector comprising a rod-shaped male member that has a flow channel, a lock lever that is located opposite to the male member, a claw that protrudes from the lock lever toward the male member, and a cover that houses the male member,
   wherein the lock lever is elastically swingable so that the claw moves away from the male member,
   the cover includes an outer circumferential wall that is elastically and compressively deformable in a longitudinal direction of the male member, and a head portion that is provided at one end of the outer circumferential wall, and
   the cover is configured such that a leading end of the male member protrudes from the head portion when the outer circumferential wall is compressively deformed,
   the adapter comprising a first end portion and a second end portion,
   wherein the adapter has a through hole that penetrates the adapter and allows the first end portion to be in communication with the second end portion,
   the first end portion includes a hollow tubular portion in which the through hole is provided,
   a first projection and a second projection are provided on an outer circumferential surface of the tubular portion, and the second projection is located on a base end side of the tubular portion with respect to the first projection,
   the adapter can be connected to the male connector at a first position where the claw of the male connector is engaged with the first projection and at a second position where the claw of the male connector is engaged with the second projection,
   when the adapter is connected to the male connector at the first position, the flow channel of the male member is sealed with the cover, and
   when the adapter is connected to the male connector at the second position, the adapter compressively deforms the outer circumferential wall of the cover so that the flow channel of the male member is in communication with the through hole of the adapter.

2. The adapter according to claim 1, wherein when the adapter is connected to the male connector at the second position, a liquid-tight seal is formed between the tubular portion and the cover.

3. The adapter according to claim 2, wherein the tubular portion includes an annular rib that surrounds the through hole, and
   the liquid-tight seal is formed by abutting of a leading end of the annular rib against the head portion of the cover.

4. The adapter according to claim 1, wherein when the adapter is connected to the male connector at the first position, the outer circumferential wall of the cover is not substantially compressively deformed.

5. The adapter according to claim 1, further comprising a large diameter portion on a base end of the tubular portion,
   wherein the large diameter portion protrudes in a radial direction compared to the first projection and the second projection.

6. The adapter according to claim 5, wherein the male connector further comprises a tubular hood that surrounds the male member, and
   when the adapter is connected to the male connector at the second position, the large diameter portion abuts against a leading end of the hood.

7. The adapter according to claim 1, wherein the first projection and the second projection are annular projections that continuously extend in a circumferential direction.

8. The adapter according to claim 1, wherein the second projection has a tapered surface on an end edge thereof facing the first projection, and an external diameter of the tapered surface gradually decreases toward the first projection.

9. The adapter according to claim 1, wherein the second end portion includes a male luer in which the through hole is provided, and
   an outer circumferential surface of the male luer is a tapered surface whose external diameter gradually decreases toward a leading end.

10. The adapter according to claim 1, wherein the second end portion of the adapter is configured symmetrically to the first end portion.

11. A male connector provided with an adapter, comprising:
    the male connector and the adapter according to claim 1.

12. The male connector provided with the adapter according to claim 11, wherein the male connector provided with the adapter are sterilized and packaged in a state in which the adapter is connected to the male connector at the first position.

* * * * *